United States Patent
Yeomans et al.

(10) Patent No.: US 9,629,894 B2
(45) Date of Patent: Apr. 25, 2017

(54) MAGNESIUM-CONTAINING OXYTOCIN FORMULATIONS AND METHODS OF USE

(71) Applicant: Trigemina, Inc., Moraga, CA (US)

(72) Inventors: David C. Yeomans, Sunnyvale, CA (US); Dean Carson, Palo Alto, CA (US); Ramachandran Thirucote, Atherton, CA (US)

(73) Assignee: TRIGEMINA, INC., Moraga, CA (US)

( * ) Notice: Subject to any disclaimer, the term of this patent is extended or adjusted under 35 U.S.C. 154(b) by 0 days.

(21) Appl. No.: 14/990,529

(22) Filed: Jan. 7, 2016

(65) Prior Publication Data

US 2016/0193282 A1 Jul. 7, 2016

Related U.S. Application Data

(60) Provisional application No. 62/100,862, filed on Jan. 7, 2015.

(51) Int. Cl.

| | | |
|---|---|---|
| *A61K 33/06* | (2006.01) | |
| *A61K 38/11* | (2006.01) | |
| *A61K 9/00* | (2006.01) | |
| *A61M 15/08* | (2006.01) | |
| *A61K 45/06* | (2006.01) | |
| *A61K 47/12* | (2006.01) | |
| *A61K 47/02* | (2006.01) | |

(52) U.S. Cl.
CPC ............ *A61K 38/11* (2013.01); *A61K 9/0043* (2013.01); *A61K 33/06* (2013.01); *A61K 45/06* (2013.01); *A61K 47/12* (2013.01); *A61M 15/08* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 1,936,364 A | 11/1933 | Pasternack et al. | |
| 2,260,004 A | 10/1941 | Davenport et al. | |
| 2,938,891 A | 5/1960 | Velluz et al. | |
| 3,076,797 A | 2/1963 | Velluz et al. | |
| 4,213,968 A | 7/1980 | Kastin et al. | |
| 4,464,378 A | 8/1984 | Hussain | |
| 4,486,441 A | 12/1984 | Fozard et al. | |
| 4,885,287 A | 12/1989 | Hussain et al. | |
| 5,482,931 A | 1/1996 | Harris et al. | |
| 5,603,943 A | 2/1997 | Yanagawa | |
| 5,624,898 A | 4/1997 | Frey, II | |
| 5,656,721 A | 8/1997 | Albert et al. | |
| 5,766,633 A | 6/1998 | Milstein et al. | |
| 5,859,048 A | 1/1999 | Oohashi et al. | |
| 5,889,110 A | 3/1999 | Hutchinson | |
| 5,914,129 A * | 6/1999 | Mauskop ............ | A61K 45/06 424/464 |
| 5,988,449 A | 11/1999 | Fuchs et al. | |
| 6,034,175 A | 3/2000 | Hutchinson | |
| 6,054,462 A | 4/2000 | Francois et al. | |
| 6,090,368 A | 7/2000 | Zia et al. | |
| 6,139,861 A | 10/2000 | Friedman | |
| 6,143,278 A | 11/2000 | Elkhoury | |
| 6,166,039 A | 12/2000 | Yaksh | |
| 6,180,603 B1 | 1/2001 | Frey, II | |
| 6,262,021 B1 | 7/2001 | Uvnas-Moberg et al. | |
| 6,313,093 B1 | 11/2001 | Frey, II | |
| 6,342,478 B1 | 1/2002 | Frey, II | |
| 6,407,061 B1 | 6/2002 | Frey, II | |
| 6,413,499 B1 | 7/2002 | Clay | |
| 6,677,346 B1 | 1/2004 | Achari et al. | |
| 6,815,424 B2 | 11/2004 | Vickery et al. | |
| 6,825,203 B2 | 11/2004 | Pasternak et al. | |
| 6,881,423 B2 | 4/2005 | Dohi et al. | |
| 6,949,509 B2 | 9/2005 | Woodrow | |
| 6,991,785 B2 | 1/2006 | Frey, II | |
| 7,273,618 B2 | 9/2007 | Frey, II et al. | |
| 7,452,868 B2 | 11/2008 | Kuzma et al. | |
| 7,714,105 B2 | 5/2010 | Moberg | |
| 7,784,460 B2 | 8/2010 | Djupesland et al. | |
| 7,854,227 B2 | 12/2010 | Djupesland | |
| 8,198,240 B2 * | 6/2012 | Yeomans ............. | A61K 9/0043 514/11.6 |
| 8,202,838 B2 | 6/2012 | Yeomans et al. | |
| 8,211,405 B2 | 7/2012 | Mueller-Waltz et al. | |
| 8,246,935 B2 | 8/2012 | Mueller-Waltz et al. | |

(Continued)

FOREIGN PATENT DOCUMENTS

| | | |
|---|---|---|
| AU | 2006282799 B2 | 3/2007 |
| DE | 43 12 913 A1 | 10/1994 |

(Continued)

OTHER PUBLICATIONS

Aboufatima, R. et al. (Apr. 8, 2004). "No Tolerance to the Antinociceptive Action of Calcitonin in Rats and Mice," *Neurosci. Lett.* 359(1-2):5-8.

Abouleish, E. (Nov.-Dec. 1976). "Postpartum Hypertension and Convulsion After Oxytocic Drugs," *Anesth. Analg.* 55(6):813-815.

Ågren, G. et al. (Sep. 29, 1997). "Olfactory Cues from an Oxytocin-Injected Male Rat Can Induce Anti-Nociception in its Cagemates," *Neuroreport* 8(14):3073-3076.

Agu, R.U. et al. (2004). "Metabolism and Absorption Enhancement of Methionine Enkephalin in Human Nasal Epithelium," *Peptides* 25:563-569.

(Continued)

*Primary Examiner* — Maury Audet

(74) *Attorney, Agent, or Firm* — Morrison & Foerster LLP

(57) ABSTRACT

Disclosed are magnesium-containing oxytocin peptide formulations or compositions comprising an oxytocin peptide and a magnesium salt that produces synergistic analgesia when used in treating pain. Also disclosed are methods for the treatment of pain (such as migraine headache) comprising co-administration of an oxytocin peptide and a magnesium salt.

24 Claims, 10 Drawing Sheets

(56) References Cited

U.S. PATENT DOCUMENTS

| | | |
|---|---|---|
| 8,252,745 B2 | 8/2012 | Yeomans et al. |
| 8,258,096 B2 | 9/2012 | Yeomans et al. |
| 8,414,867 B2 | 4/2013 | Mueller-Walz et al. |
| 9,034,821 B2 | 5/2015 | Uvnäs-Moberg et al. |
| 2001/0043915 A1 | 11/2001 | Frey, II |
| 2001/0055607 A1 | 12/2001 | Levin |
| 2002/0028786 A1 | 3/2002 | Frey, II et al. |
| 2002/0072498 A1 | 6/2002 | Frey, II |
| 2002/0082215 A1 | 6/2002 | Frey, II |
| 2002/0141971 A1 | 10/2002 | Frey, II |
| 2002/0169102 A1 | 11/2002 | Frey, II |
| 2003/0072793 A1 | 4/2003 | Frey, II et al. |
| 2003/0077300 A1 | 4/2003 | Wermeling |
| 2003/0104085 A1 | 6/2003 | Yeomans |
| 2003/0119892 A1 | 6/2003 | Caldwell et al. |
| 2003/0165434 A1 | 9/2003 | Reinhard et al. |
| 2003/0185872 A1 | 10/2003 | Kochinke |
| 2003/0215398 A1 | 11/2003 | Frey, II |
| 2003/0223981 A1 | 12/2003 | Mochly-Rosen et al. |
| 2003/0229025 A1 | 12/2003 | Xiao et al. |
| 2004/0105889 A1 | 6/2004 | Ryde et al. |
| 2004/0120896 A1 | 6/2004 | Dugger, III |
| 2004/0204366 A1 | 10/2004 | Pasternak et al. |
| 2004/0258757 A1 | 12/2004 | Bosch et al. |
| 2005/0142072 A1 | 6/2005 | Birch et al. |
| 2005/0153885 A1 | 7/2005 | Yun et al. |
| 2005/0272642 A1 | 12/2005 | Frey, II et al. |
| 2006/0009413 A1 | 1/2006 | Frey, II et al. |
| 2006/0009414 A1 | 1/2006 | Frey, II et al. |
| 2006/0014716 A1 | 1/2006 | Frey, II et al. |
| 2006/0030542 A1 | 2/2006 | Frey, II et al. |
| 2006/0039995 A1 | 2/2006 | Frey, II et al. |
| 2006/0135437 A1 | 6/2006 | Stoehr et al. |
| 2006/0142181 A1* | 6/2006 | Miller ............. A61K 47/48238 514/1.2 |
| 2006/0159626 A1 | 7/2006 | Frey, II |
| 2006/0188496 A1 | 8/2006 | Bentz et al. |
| 2006/0216317 A1 | 9/2006 | Reinhard et al. |
| 2006/0252685 A1 | 11/2006 | Gould |
| 2007/0004743 A1 | 1/2007 | Xiao et al. |
| 2007/0054843 A1 | 3/2007 | Yeomans et al. |
| 2007/0071690 A1 | 3/2007 | Mueller-Walz et al. |
| 2007/0093420 A1 | 4/2007 | Yeomans et al. |
| 2009/0317377 A1 | 12/2009 | Yeomans et al. |
| 2010/0035854 A1 | 2/2010 | Mueller-Walz et al. |
| 2010/0080797 A1 | 4/2010 | Yeomans et al. |
| 2011/0237508 A1 | 9/2011 | Amorij |
| 2012/0244196 A1 | 9/2012 | Okubo et al. |
| 2012/0322736 A1 | 12/2012 | Yeomans et al. |

FOREIGN PATENT DOCUMENTS

| | | |
|---|---|---|
| EP | 0 122 036 | 2/1989 |
| EP | 1 077 070 A2 | 2/2001 |
| EP | 0 681 833 B1 | 6/2001 |
| EP | 0 696 208 B1 | 8/2001 |
| EP | 0 710 122 B1 | 12/2001 |
| EP | 1 466 610 A1 | 10/2004 |
| EP | 1 468 690 A1 | 10/2004 |
| EP | 1 239 845 B1 | 3/2005 |
| EP | 1 025 840 B1 | 6/2005 |
| EP | 1 689 360 A1 | 8/2006 |
| EP | 1 409 518 B1 | 12/2007 |
| EP | 1 121 935 B1 | 8/2008 |
| EP | 1 928 484 B1 | 11/2008 |
| EP | 2 161 030 A1 | 3/2010 |
| EP | 2 326 341 A2 | 6/2011 |
| EP | 2 696 882 B1 | 3/2015 |
| EP | 2 489 348 B1 | 11/2016 |
| JP | 2001-2589 A | 1/2001 |
| JP | 2001-89359 A | 4/2001 |
| JP | 2001-527537 A | 12/2001 |
| JP | 2005-500258 A | 1/2005 |
| JP | 2009-506071 A | 2/2009 |
| JP | 2009-506076 A | 2/2009 |
| WO | WO-86/06959 A1 | 12/1986 |
| WO | WO-91/07947 A1 | 6/1991 |
| WO | WO-93/15737 A1 | 8/1993 |
| WO | WO-93/17037 A1 | 9/1993 |
| WO | WO-94/21286 A1 | 9/1994 |
| WO | WO-94/23767 A1 | 10/1994 |
| WO | WO-95/01185 A1 | 1/1995 |
| WO | WO-98/42275 A1 | 10/1998 |
| WO | WO-98/43660 A1 | 10/1998 |
| WO | WO-00/33813 A1 | 6/2000 |
| WO | WO-00/33814 A2 | 6/2000 |
| WO | WO-00/33814 A3 | 6/2000 |
| WO | WO-01/26642 A2 | 4/2001 |
| WO | WO-01/41732 A1 | 6/2001 |
| WO | WO-01/43775 A2 | 6/2001 |
| WO | WO-02/076388 A2 | 10/2002 |
| WO | WO-02/076388 A3 | 10/2002 |
| WO | WO-02/082074 A1 | 10/2002 |
| WO | WO-02/086105 A1 | 10/2002 |
| WO | WO-02/102832 A1 | 12/2002 |
| WO | WO-03/072056 A1 | 9/2003 |
| WO | WO-03/093816 A2 | 11/2003 |
| WO | WO-03/093816 A3 | 11/2003 |
| WO | WO-2004/019875 A2 | 3/2004 |
| WO | WO-2004/019875 A3 | 3/2004 |
| WO | WO-2004/043428 A2 | 5/2004 |
| WO | WO-2004/043428 A3 | 5/2004 |
| WO | WO-2004/062563 A2 | 7/2004 |
| WO | WO-2004/062563 A3 | 7/2004 |
| WO | WO-2004/093897 A1 | 11/2004 |
| WO | WO-2005/046636 A1 | 5/2005 |
| WO | WO-2005/115370 A2 | 12/2005 |
| WO | WO-2005/115370 A3 | 12/2005 |
| WO | WO-2006/020727 A2 | 2/2006 |
| WO | WO-2006/091332 A2 | 8/2006 |
| WO | WO-2006/091332 A3 | 8/2006 |
| WO | WO-2007/025249 A2 | 3/2007 |
| WO | WO-2007/025249 A3 | 3/2007 |
| WO | WO-2007/025286 A2 | 3/2007 |
| WO | WO-2007/025286 A3 | 3/2007 |
| WO | WO-2010/030180 A2 | 3/2010 |
| WO | WO-2011/040597 A1 | 4/2011 |
| WO | WO-2011/120071 A1 | 10/2011 |
| WO | WO-2012/042371 A2 | 4/2012 |
| WO | WO-2012/140216 A1 | 10/2012 |

OTHER PUBLICATIONS

Amico, J.A. et al. (Nov. 1983). "A Time-Dependent Peak of Oxytocin Exists in Cerebrospinal Fluid but Not in Plasma of Humans," *J. Clin. Endocrinol. Metab.* 57(5):947-951.

Arletti, R. et al. (Mar. 1993). "Influence of Oxytocin on Nociception and Morphine Antinociception," *Neuropeptides* 24(3):125-129.

Atke et al. "Uterotonic Activity and Myometrial Receptor Affinity of 1-Deamino-1-Carba-2-Tyrosine(O-Methyl)-Oxytocin," Acta Endocrinologica (1987) 115(1):155-60.

Avanti, C. et al. "A New Strategy to Stabilize Oxytocin in Aqueous Solutions: I The Effects of Divalent Metal Ions and Citrate Buffer", The AAPS Journal, (2011), vol. 13, No. 2, pp. 284-290.

Beck, E. et al. (Feb. 15, 2005). "Management of Cluster Headache," *American Family Physician* 71(4):717-724.

Bessette, L. et al. (1998). "A Placebo Controlled Crossover Trial of Subcutaneous Salmon Calcitonin in the Treatment of Patients with Fibromyalgia," *Scand. J. Rheumatol.* 27(2):112-116.

Born, J. et al. (Jun. 2002). "Sniffing Neuropeptides: A Transnasal Approach to the Human Brain," *Nat. Neurosci.* 5(6):514-516.

Braga, P.C. et al. (Mar. 5, 1993). "Antinociceptive Activity of Salmon Calcitonin: Electrophysiological Correlates in a Rat Chronic Pain Model," *Neurosci. Lett.* 151(1):85-88.

Brown, D.C. et al. (1998). "Oxytocin Content of the Cerebrospinal Fluid of Dogs and its Relationship to Pain Induced by Spinal Cord Compression," *Vet. Surg.* 27(6):607-611.

Calvin, W.H. et al. (Apr. 1977). "A Neurophysiological Theory for the Pain Mechanism of Tic Douloureux," *Pain* 3(2):147-154.

(56) References Cited

OTHER PUBLICATIONS

Candeletti, S. et al. (Feb. 1992). "Intracerebroventricular Salmon Calcitonin Reduces Autotomy Behavior in Rats After Dorsal Rhizotomy," *Pain* 48(2):275-278.
Capsoni, S. et al. (2009). "Delivery of NGF to the Brain: Intranasal Versus Ocular Administration in Anti-NGF Transgenic Mice," *Journal of Alzheimer's Disease* 16:371-388.
Carlton, S.M. et al. (Jun. 1, 2001). "Tonic Control of Peripheral Cutaneous Nociceptors by Somatostatin Receptors," *J. Neurosci.* 21(11):4042-4049.
Carlton, S.M. et al. (2004). "Somatostatin Modulates the Transient Receptor Potential Vanilloid 1 (TRPV1) Ion Channel," *Pain* 110(3):616-627.
Carr, D.B. et al. (2004). "Safety and Efficacy of Intranasal Ketamine for the Treatment of Breakthrough Pain in Patients with Chronic Pain: a Randomized, Double-Blind, Placebo-Controlled, Crossover Study," *Pain* 108(1-2):17-27.
Carstens, J.H. Jr. et al. (1991). "Future Horizons for Calcitonin: A U.S. Perspective," *Calcif. Tissue Int.* 49(Suppl. 2):S2-S6.
Chevillard, C. et al. (1984). "Angiotensin-Converting Enzyme in Discrete Forebrain Areas of Spontaneously Hypertensive Rats," *Brain Res.* 309:389-392.
Condés-Lara, M. et al. (Jun. 20, 2003). "Actions of Oxytocin and Interactions with Glutamate on Spontaneous and Evoked Dorsal Spinal Cord Neuronal Activities," *Brain Res.* 976(1):75-81.
Condés-Lara, M. et al. (May 31, 2005). "Oxytocin Actions on Afferent Evoked Spinal Cord Neuronal Activities in Neuropathic but not in Normal Rats," *Brain Res.* 1045(1-2):124-133.
Condés-Lara, M. et al. (Apr. 7, 2006). "Paraventricular Hypothalamic Influences on Spinal Nociceptive Processing," *Brain Res.* 1081(1):126-137.
Copp, D.H. (Jun. 1994). "Calcitonin: Discovery, Development, and Clinical Application," *Clin. Invest. Med.* 17(3):268-277.
Dale, O. et al.(Aug. 2002). "Nasal Administration of Opioids for Pain Management in Adults," *Acta Anaesthesiologica Scandinavica* 46(7):759-770.
De Fraissinette, A. et al. (Oct. 1995). "In vitro Tolerability of Human Nasal Mucosa: Histopathological and Scanning Electron-Microscopic Evaluation of Nasal Forms Containing Sandostatin®," *Cell Biol. Toxicol.* 11(5):295-301.
De Marinis, M. et al. (1990). "Increased Reactivity to a Met-Enkephalin Analogue in the Control of Autonomic Responses in Migraine Patients". *Clin. Neuropharmacol.*13(6):507-521.
Eggers, T.R. et al. (Feb. 1979). "Water Intoxication and Syntocinon Infusion," *Aust. N.Z. J. Obstet. Gynaecol.* 19(1):59-60.
Engstrøm et al. "Oxytocin Receptor Binding and Uterotonic Activity of Carbetocin and Its Metabolites Following Enzymatic Degradation," *Eur. J. Pharmacol.* 1998 355(2-3):203-10.
Epperson, C.N. et al. (1996). "Intranasal Oxytocin in Obsessive-Compulsive Disorder," *Biol. Psychiatry* 40(6):547-549.
Epperson, C.N. et al. (1996). "Intranasal Oxytocin in Trichotillomania," *Biol. Psychiatry* 40(6):559-560.
Ezzat, S. et al. (Nov. 1, 1992). "Octreotide Treatment of Acromegaly. A Randomized, Multicenter Study," *Annals of Internal Medicine* 117(9):711-718.
Fabbri, A. et al. (Sep. 23, 1985). "Calcitonin Receptors in the Rat Mesencephalon Mediate its Analgesic Actions: Autoradiographic and Behavioral Analyses," *Brain Res.* 343(2):205-215.
Fanciullacci, M. et al. (1997). "Responsiveness of the Trigeminovascular System to Nitroglycerine in Cluster Headache Patients," *Brain* 120:283-288.
Fassler, J.E. et al. (1990). "Octreotide Inhibits Increases in Short-Circuit Current Induced in Rat Colon by Vip, Substance P, Serotonin and Aminophylline," *Regulatory Peptides* 29(23):189-197.
Fischer, M.J.M. et al. (Jun. 22, 2005). "The Nonpeptide Calcitonin Gene-Related Peptide Receptor Antagonist BIBN4096BS Lowers the Activity of Neurons with Meningeal Input in the Rat Spinal Trigeminal Nucleus," *The Journal of Neuroscience* 25(25):5877-5883.

Flood, P. et al. (Dec. 2004). "Intranasal Nicotine for Postoperative Pain Treatment," *Anesthesiology* 101(6):1417-1421.
Frey, W.H. II (Jul./Aug. 2002). "Bypassing the Blood-Brain Barrier to Deliver Therapeutic Agents to the Brain and Spinal Cord," *Drug Delivery Technology* 2(5):46-49.
Gabopoulou, Z. et al. (Dec. 2002). "Epidural Calcitonin: Does it Provide Better Postoperative Analgesia? An Analysis of the Haemodynamic, Endocrine, and Nociceptive Responses of Salmon Calcitonin and Opioids in Epidural Anesthesia for Hip Arthroplasty Surgery," *Pain Pract.* 2(4):326-331.
Gaginella, T.S. et al. (Sep. 1990). "Treatment of Endocrine and Nonendocrine Secretory Diarrheal States with Sandostatin®," *Metabolism: Clinical and Experimental* 39(9 Suppl 2):172-175.
Gao, L. et al. (2004). "Involvement of Opioid Receptors in the Oxytocin-Induced Antinociception in the Central Nervous System of Rats," *Regulatory Peptides* 120:53-58.
Gazelius, B. et al. (1981). "Evidence that Substance P is a Mediator of Antidromic Vasodilatation Using Somatostatin as a Release Inhibitor," *Acta Physiologica Scandinavica* 113(2):155-159.
Ge, Y. et al. (Feb. 15, 2002). "Blockade Effect of mu and kappa Opioid Antagonists on the Anti-Nociception Induced by Intra-Periaqueductal Grey Injection of Oxytocin in Rats," *Brain Res.* 927(2):204-207.
Ghai, B. et al. (Oct.-Dec. 2004). "Complex Regional Pain Syndrome: A Review," *J. Postgraduate Medicine* 50(4):300-307.
Gimpl, G. et al. (Apr. 2001). "The Oxytocin Receptor System: Structure, Function and Regulation," *Physiol. Rev.* 81(2):629-683.
Goadsby, P.J. (2005). "New Targets in the Acute Treatment of Headache," *Current Opinion in Neurology* 18(3):283-288.
Goadsby, P.J. (Apr. 2005). "Migraine Pathophysiology," *Headache* 45(Suppl.1):S14-S24.
Gobelet, C. et al. (Sep. 1986). "Calcitonin and Reflex Sympathetic Dystrophy Syndrome," *Clin. Rheumatol.* 5(3):382-388.
Goldstein J. et al. (1998) "Comparison of butorphanol nasal spray and fiorinal with codeine in the treatment of migrane", Headache: The Journal of Head and Face Pain, 38(7):516-522.
Goodlin, R.C. (Dec. 15, 1985). "Is Oxytocin the Culprit?" *Am. J. Obstet Gynecol.* 153(8):928-929.
Gozes, I. (Dec. 2001). "Neuroprotective Peptide Drug Delivery and Development: Potential New Therapeutics," *Trends in Neurosciences* 24(12):700-705.
Granger, P. et al. (1995). "Modulation of the γ-Aminobutyric Acid Type A Receptor by the Antiepileptic Drugs Carbamazepine and Phenytoin," *Molecular Pharmacology* 47:1189-1196.
Guidobono, F. et al. (Mar.-Apr. 1986). "Eel Calcitonin Binding Site Distribution and Antinociceptive Activity in Rats," *Peptides* 7(2):315-322.
Gupta, D.R. et al. (May 1, 1972). "Oxytocin, 'Salting Out,' and Water Intoxication," *JAMA* 220(5):681-683.
Gwak, H.S. et al. (2003). "Analgesic Effects of Intra-Nasal Enkephalins," *J. Pharm. Pharmacol.* 55:1207-1212.
Hackler, L. et al. (1997). "Isolation of Relatively Large Amounts of Endomorphin-1 and Endomorphin-2 From Human Brain Cortex," *Peptides* 18(10):1635-1639.
Haldemann, A.R. et al. (Mar. 1995). "Somatostatin Receptor Scintigraphy in Central Nervous System Tumors: Role of Blood-Brain Barrier Permeability," *J. Nucl. Med.* 36(3):403-410.
Hamamci, N. et al. (Oct.-Nov., 1996). "Calcitonin Treatment in Reflex Sympathetic Dystrophy: A Preliminary Study," *Br. J. Clin. Pract.* 50(7):373-375.
Harris, R.E. (Jun. 1970). "Water Intoxication Secondary to Oxytocin," *VA Med. Mon.* 97(6):357-359.
Hawe et al. Pharmaceut. Res. 26:1679-1688 (2009).
Heinrichs, M. et al. (Oct. 30, 2004). "Selective Amnesic Effects of Oxytocin on Human Memory," *Physiol Behav.* 83(1):31-38.
Helmchen, C. et al. (1995). "Inhibition of Spinal Nociceptive Neurons by Microinjections of Somatostatin into the Nucleus Raphe Magnus and the Midbrain Periaqueductal Gray of the Anesthetized Cat," *Neuro. Lett.* 187(2):137-141.
Helyes, Z. et al. (1996). "Anti-Inflammatory and Antinociceptive Effect of Different Somatostatin-Analogs," *Neurobiology* 4(1-2):115-117.

(56) References Cited

OTHER PUBLICATIONS

Helyes, Z. et al. (2000). "Anti-Nociceptive Effect Induced by Somatostatin Released from Sensory Nerve Terminals and by Synthetic Somatostatin Analogues in the Rat," *Neuro. Lett.* 278(3):185-188.

Helyes, Z. et al. (2001). "Anti-Inflammatory Effect of Synthetic Somatostatin Analogues in the Rat," *British Journal of Pharmacology* 134(7):1571-1579.

Helyes, Z. et al. (May 2004). "Antiinflammatory and Analgesic Effects of Somatostatin Released from Capsaicin-Sensitive Sensory Nerve Terminals in a Freund's Adjuvant-Induced Chronic Arthritis Model in the Rat," *Arthritis and Rheumatism* 50(5):1677-1685.

Hoover, R.T. (1971). "Intranasal Oxytocin in Eighteen Hundred Patients. A Study on its Safety as Used in a Community Hospital," *Am. J. Obstet. Gynecol.* 110(6):788-794.

Hruby, V.J. et al. (Jul.-Sep. 1989). "Recent Developments in the Design of Receptor Specific Opioid Peptides," *Medicinal Research Reviews* 9(3):343-401.

Hunter, D.D. et al. (1998). "Identification and Neuropeptide Content of Trigeminal Neurons Innervating the Rat Nasal Epithelium," *Neuroscience* 83(2):591-599.

Illum, L. (Dec. 2002). "Nasal Drug Delivery: New Developments and Strategies," *Drug Discovery Today* 7(23):1184-1189.

Illum, L. (Jan. 2004). "Is Nose-To-Brain Transport of Drugs in Man a Reality?" *J. Pharm. Pharmacol.* 56(1):3-17.

International Search Report mailed on May 2, 2016, for PCT Application No. PCT/US2016/012512, internationally filed on Jan. 7, 2016, 8 pages.

Invitti, C. et al. (1996). "Effect of Chronic Treatment with Octreotide Nasal Powder on Serum Levels of Growth Hormone, Insulin-Like Growth Factor I, Insulin-Like Growth Factor Binding Proteins 1 and 3 in Acromegalic Patients," *J. Endocrino. Invest.* 19(8):548-555.

Jaeger, H. et al. (Jan. 1992). "Calcitonin in Phantom Limb Pain: a Double-Blind Study," *Pain* 48(1):21-27.

Jallad, R.S. et al. (2005). "Treatment of Acromegaly with Octreotide-LAR: Extensive Experience in a Brazilian Institution," *Clinical Endocrinology* 63(2):168-175.

Jo, Y-H. et al. (Apr. 1, 1998). "Oxytocin Modulates Glutamatergic Synaptic Transmission Between Cultured Neonatal Spinal Cord Dorsal Horn Neurons," *J. Neurosci.* 18(7):2377-2386.

Josey, W.E. et al. (Jul. 15, 1969). "Oxytocin-Induced Water Intoxication," *Am. J. Obstet. Gynecol.* 104(6):926.

Kang, Y.S. et al. (2000). "Brain Uptake and the Analgesic Effect of Oxytocin—its Usefulness as an Analgesic Agent," *Arch. Pharm. Res.* 23(4):391-395.

Kapicioglu, S. et al. (1997). "Treatment of Migraine Attacks with a Long-Acting Somatostatin Analogue (Octreotide, SMS 201-995)," *Cephalalgia* 17(1):27-30. (eight pages).

Kaplan, E. (Jan. 7, 1978). "A Generalized Epileptiform Convulsion After Intra-Amniotic Prostaglandin with Intravenous Oxytocin Infusion: A Case Report," *S. Afr. Med. J.* 53(1):27-29.

Katai, M. et al. (2005). "Octreotide as a Rapid and Effective Painkiller for Metastatic Carcinoid Tumor," *Endocrine Journal* 52(2):277-280.

Kirsch, P. et al. (Dec. 7, 2005). "Oxytocin Modulates Neural Circuitry for Social Cognition and Fear in Humans," *J. Neurosci.* 25(49):11489-11493.

Kitazawa, T. et al. (1998). "Efflux of Taurocholic Acid Across the Blood-Brain Barrier: Interaction with Cyclic Peptides," *The Journal of Pharmacology and Experimental Therapeutics* 286(2):890-895.

Kosfeld, M. et al. (Jun. 2, 2005). "Oxytocin Increases Trust in Humans," *Nature* 435:673-676.

Lamberts, S.W.J. (1988). "The Role of Somatostatin in the Regulation of Anterior Pituitary Hormone Secretion and the Use of Its Analogs in the Treatment of Human Pituitary Tumors," *Endocrine Reviews* 9(4):417-436.

Lamberts, S.W.J. et al. (Jan. 25, 1996). "Octreotide," *The New England Journal of Medicine* 334(4):246-254.

Landau R. et al. "Chronic pain after childbirth", International Journal of Obstetric Anesthesia, (2013), vol. 22, No. 2, pp. 133-145.

Landgraf, R. (1985). "Plasma Oxytocin Concentrations in Man After Different Routes of Administration of Synthetic Oxytocin," *Exp. Clin. Endocrinol.* 85(2):245-248.

Lee, H.M. et al. (Nov. 28, 2003). "Diclofenac Inhibition of Sodium Currents in Rat Dorsal Root Ganglion Neurons," *Brain Res.* 992(1):120-127.

Lerner, E.N. (Jun. 2004). "Enhanced Delivery of Octreotide to the Brain via Transnasal Iontophoretic Administration," *Journal of Drug Targeting* 12(5):273-280.

Levy, M.J. et al. (Jul.-Aug. 2003). "Acromegaly: A Unique Human Headache Model," *Headache* 43(7):794-797.

Levy, M.J. et al. (2003). "Somatostatin Infusion Withdrawal: A Study of Patients with Migraine, Cluster Headache and Healthy Volunteers," *Pain* 102(3):235-241.

Levy, M.J. et al. (2004). "Octreotide is not Effective in the Acute Treatment of Migraine," *Cephalalgia* 25(1):48-55.

Levy, M.J. et al. (Aug. 2005; e-pub. May 11, 2005). "The Clinical Characteristics of Headache in Patients with Pituitary Tumours," *Brain* 128(Pt. 8):1921-1930.

List, M.A. et al. (2000). "Evaluation of Quality of Life in Patients Definitely Treated for Squamous Carcinoma of the Head and Neck," *Curr. Opin. Oncol.* 12:215-220.

Loup, F. et al. (Oct. 23, 1989). "Localization of Oxytocin Binding Sites in the Human Brainstem and Upper Spinal Cord: an Autoradiographic Study," *Brain Res.* 500(1-2):223-230.

Loup, F. et al. (Aug. 2, 1991). "Localization of High-Affinity Binding Sites for Oxytocin and Vasopressin in the Human Brain. An Autoradiographic Study," *Brain Res.* 555(2):220-232.

Lundeberg, T. et al. (Mar. 28, 1994). "Anti-Nociceptive Effects of Oxytocin in Rats and Mice," *Neurosci. Lett.* 170(1):153-157.

Lussier, D. et al. (2004). "Adjuvant Analgesics in Cancer Pain Management," *The Oncologist* 9(5):571-591.

Lustig, R.H. et al. (2006; e-pub. Sep. 13, 2005). "A Multicenter, Randomized, Double-Blind, Placebo-Controlled, Dose-Finding Trial of a Long-Acting Formulation of Octreotide in Promoting Weight Loss in Obese Adults with Insulin Hypersecretion," *International Journal of Obesity* 30(2):331-341.

Lyritis, G.P. et al. (1997). "Pain Relief from Nasal Salmon Calcitonin in Osteoporotic Vertebral Crush Fractures. A Double Blind, Placebo-Controlled Clinical Study," *Acta Orthop. Scand.* 68(Suppl.275):112-114.

Madrazo, I. et al. (1987). "Intraventricular Somatostatin-14, Arginine Vasopressin, and Oxytocin: Analgesic Effect in a Patient with Intractable Cancer Pain," *Appl. Neurophysiol.* 50(1-6):427-431.

Maeda, Y. et al. (1994). "Inhibitory Effects of Salmon Calcitonin on the Tail-Biting and Scratching Behavior Induced by Substance P and Three Excitatory Amino Acids," *J. Neural Transm.* (Gen. Sect.) 96(2):125-133.

Martin, W. et al. (1999). "Spinal cannabinoids are anti-allodynic in rats with persistent inflammation", *Pain*, 82:199-205.

Matharu, M.S. et al. (Oct. 2004; e-pub. Sep. 30, 2004). "Subcutaneous Octreotide in Cluster Headache: Randomized Placebo-Controlled Double-Blind Crossover Study," *Ann. Neurol.* 56(4):488-494.

Matharu, M.S. et al. (Nov. 2004). "Subcutaneous Octreotide in Cluster Headache: Randomized Placebo-Controlled Double-Blind Crossover Study," *Erratum, Ann. Neurol.* 56(5):751.

McKenna, P. et al. (Nov.-Dec. 1979). "Hyponatremic Fits in Oxytocin-Augmented Labors," *Int. J. Gynaecol. Obstet.* 17(3):250-252.

Mens, W.B.J. et al. (Feb. 28, 1983). "Penetration of Neurohypophyseal Hormones from Plasma into Cerebrospinal Fluid (CSF): Half-Times of Disappearance of These Neuropeptides from CSF," *Brain Res.* 262(1):143-149.

Meunier, A. (Apr. 2005). Attenuation of Pain-Related Behaviour in a Rat Model of Trigeminal Neuropathic Pain by Viral-Driven Enkephalin Overproduction in Trigeminal Ganglion Neurons, *Molecular Therapy* 11(4):608-616.

Millan, M.J. et al. (Sep. 19, 1984). "Vasopressin and Oxytocin in the Rat Spinal Cord: Analysis of Their Role in the Control of Nociception," *Brain Res.* 309(2):384-388.

(56) References Cited

OTHER PUBLICATIONS

Miralles, F.S. et al. (Jul. 1987). "Postoperative Analgesia Induced by Subarachnoid Lidocaine Plus Calcitonin," *Anesth. Analg.* 66(7):615-618.

Musolino, N.R. et al. (1990). "Headache in Acromegaly: Dramatic Improvement with the Somatostatin Analogue SMS 201-995," *The Clinical Journal of Pain* 6(3):243-245.

Newman, C.B. et al. (Sep. 1998). "Octreotide as Primary Therapy for Acromegaly," *The Journal of Clinical Endocrinology and Metabolism* 83(9):3034-3040.

Ofluoglu, D. et al. (Jan. 2007; e-pub. Mar. 31, 2006). "The Effect of Calcitonin on β-Endorphin Levels in Postmenopausal Osteoporotic Patients with Back Pain," *Clin. Rheumatol.* 26(1):44-49.

Olesen, J. (2004). "The International Classification of Headache Disorders," *Cephalalgia* 24(Suppl. 1):1-151.

Paice, J.A. et al. (Jan. 1996). "Intrathecal Octreotide for Relief of Intractable Nonmalignant Pain: 5-Year Experience with Two Cases," *Neurosurgery* 38(1):203-207, located at <http://gateway.ut.ovid.com/gw1/ovidweb.cgi>, last visited Mar. 30, 2007, ten pages.

Parker, K.J. et al. (Oct. 2005). "Intranasal Oxytocin Administration Attenuates the ACTH Stress Response in Monkeys," *Psychoneuroendocrinology* 30(9):924-929.

Pascual, J. et al. (1991). "Analgesic Effect of Octreotide in Headache Associated with Acromegaly is not Mediated by Opioid Mechanisms. Case Report," *Pain* 47(3):341-344.

Pawlak, M. et al. (2004). "Octreotide, a Somatostatin Analogue, Attenuates Movement Evoked Discharges of Fine Afferent Units from Inflamed Knee Joints of Rats," *Neuro. Lett.* 361(1-3):180-183.

Pedlow, P.R.B. (Dec. 1970). "Syntocinon Induced Convulsion," *J. Obstet. Gynaecol. Br. Commonw.* 77(12):1113-1114.

Penn, R.D. et al. (Apr. 1992). "Octreotide: A Potent New Non-Opiate Analgesic for Intrathecal Infusion," *Pain* 49(1):13-19.

Petersson, M. et al. (Jul. 12, 1996). "Oxytocin Increases Nociceptive Thresholds in a Long-Term Perspective in Female and Male Rats," *Neurosci. Lett.* 212(2):87-90.

Petersson, M. et al. (Aug. 16, 2005). "Oxytocin Decreases Corticosterone and Nociception and Increases Motor Activity in OVX Rats," *Maturitas* 51(4):426-433.

Phillips, W.J. et al. (2006). "Relief of Acute Migraine Headache with Intravenous Oxytocin: Report of Two Cases," *J. Pain Palliat. Care Pharmacother.* 20(3):25-28.

Potter, R.R. (May 1964). "Water Retention Due to Oxytocin," *Obstet. Gynecol.* 23(5):699-702.

Randić, M. et al. (1978). "Depressant Actions of Methionine-Enkephalin and Somatostatin in Cat Dorsal Horn Neurones Activated by Noxious Stimuli," *Brain Res.* 152(1):196-202.

Reiter, M.K. et al. (Jan. 1, 1994). "Localization of Oxytocin Binding Sites in the Thoracic and Upper Lumbar Spinal Cord of the Adult and Postnatal Rat: A Histoautoradiographic Study," *Eur. J. Neurosci.* 6(1):98-104.

Robbins Headache Clinic. (2004). "Combination Therapy for Migraines," located at <http://www.headachedrugs.com/archives2/combination.html>, last visited May 1, 2007, two pages.

Robinson, D.A. et al. (Apr. 15, 2002). "Oxytocin Mediates Stress-Induced Analgesia in Adult Mice," *J. Physiol.* 540(Pt. 2):593-606.

Ross, T.M. et al. (2004). "Intranasal Administration of Interferon Beta Bypasses the Blood-Brain Barrier to Target the Central Nervous System and Cervical Lymph Nodes: A Non-Invasive Treatment Strategy for Multiple Sclerosis," *Journal of Neuroimmunology* 151:66-77.

Sahin, F. et al. (Mar. 2006; e-pub. Jun. 25, 2005). "Efficacy of Salmon Calcitonin in Complex Regional Pain Syndrome (Type 1) in Addition to Physical Therapy," *Clin. Rheumatol.* 25(2):143-148.

Sakurada, S. et al. (2002). "Recent Advances in the Search for the μ-Opioidergic System: Differential Antinociceptive Effects Induced by Intrathecally-Administered Endomorphin-1 and Endomorphin-2 in Mice," *Jpn. J. Pharmacol.* 89:221-223.

Sances, G. et al. (Apr. 2003). "Course of Migraine During Pregnancy and Postpartum: A Prospective Study," *Cephalalgia* 23(3):197-205.

Sandler, L.M. et al. (1987). "Effective Long-Term Treatment of Acromegaly with a Long-Acting Somatostatin Analogue (SMS 201-995)," *Clinical Endocrinology* 26(1):85-95.

Sayani, A.P. et al. (1996). "Systemic Delivery of Peptides and Proteins Across Absorptive Mucosae," *Critical Reviews in Therapeutic Drug Carrier Systems* 13(1&2):85-184.

Schindler, M. et al. (1997). "Immunohistochemical Localization of the Somatostatin $SST_{2(A)}$ Receptor in the Rat Brain and Spinal Cord," *Neuroscience* 76(1):225-240.

Schindler, M. et al. (1998). "Identification of Somatostatin $sst_{2(a)}$ Receptor Expressing Neurones in Central Regions Involved in Nociception," *Brain Res.* 798(1-2):25-35.

Schmidt, K. et al. (May 1993). "Analgesic Effect of the Somatostatin Analogue Octreotide in Two Acromegalic Patients: A Double-Blind Study with Long-Term Follow-up," *Pain* 53(2):223-227.

Schmidt, M. et al. (Jul. 1998). "Somatostatin Receptor Imaging in Intracranial Tumours," *European Journal of Nuclear Medicine* 25(7):675-686.

Schwartz, G. et al. (1996). "Effects of Salmon Calcitonin on Patients with Atypical (Idiopathic) Facial Pain: A Randomized Controlled Trial," *J. Orofac. Pain* 10(4):306-315.

Schwetz, I. et al. (2004). "Anti-Hyperalgesic Effect of Octreotide in Patients with Irritable Bowel Syndrome," *Alimentary Pharmacology & Therapeutics* 19(1):123-131.

Seifer, D.B. et al. (Mar. 1985). "Water Intoxication and Hyponatremic Encephalopathy from the Use of an Oxytocin Nasal Spray," *J. Repro. Med.* 30(3):225-228.

Selmer, I. et al. (2000). "Advances in Understanding Neuronal Somatostatin Receptors," *Regulatory Peptides* 90(1-3):1-18.

Selmer, I-S. et al. (2000). "First Localisation of Somatostatin ssta Receptor Protein in Selected Human Brain Areas: An Immunohistochemical Study," *Mol. Brain Res.* 82(1-2):114-125.

Sibilia, V. et al. (2000). "Amylin Compared with Calcitonin: Competitive Binding Studies in Rat Brain and Antinociceptive Activity," *Brain Res.* 854(1-2):79-84.

Sicolo, N. et al. (1990). "Analgesic Effect of Sandostatin (SMS 201-995) on Acromegaly Headache," *Minerva Endocrinol.* 15(1):37-42. (Article in Italian, Abstract in English.).

Sicuteri, F. et al. (1984). "Pain Relief by Somatostatin in Attacks of Cluster Headache," *Pain* 18(4):359-365.

Strassman, A.M. et al. (Mar. 2006). "Response Properties of Dural Nociceptors in Relation to Headache," *J. Neurophysiol.* 95(3):1298-1306.

Staszczuk P. et al. (2003), "Methods of Preparation of Magnesium Organic Compounds from Natural Dolomite", *Physicochem Problems of Mineral Processing*, 37:149-158.

Striebel, H.W. et al. (1996). "Patient-Controlled Intranasal Analgesia: A Method for Noninvasive Postoperative Pain Management," *Anesth. Analg.* 83:548-551.

Szolcsányi, J. et al. (1998). "Release of Somatostatin and Its Role in the Mediation of the Anti-Inflammatory Effect Induced by Antidromic Stimulation of Sensory Fibres of Rat Sciatic Nerve," *British Journal of Pharmacology* 123(5):936-942.

Szolcsányi, J. et al. (1998). "Systemic Anti-Inflammatory Effect Induced by Counter-Irritation Through a Local Release of Somatostatin from Nociceptors," *British Journal of Pharmacology* 125(4):916-922.

Tafazal, S.I. et al. (Feb. 2007). "Randomised Placebo-Controlled Trial on the Effectiveness of Nasal Salmon Calcitonin in the Treatment of Lumbar Spinal Stenosis," *Eur. Spine J.* 16(2):207-212.

Thán, M. et al. (Jul. 7, 2000). "Systemic Anti-Inflammatory Effect of Somatostatin Released from Capsaicin-Sensitive Vagal and Sciatic Sensory Fibres of the Rat and Guinea-Pig," *European Journal of Pharmacology* 399(2-3):251-258.

Thorne, R.G. (2004). "Delivery of Insulin-Like Growth Factor-I to the Rat Brain and Spinal Cord Along Olfactory and Trigeminal Pathways Following Intranasal Administration," *Neuroscience* 127:481-496.

Truini, A. et al. (Sep. 2005). "New Insight into Trigeminal Neuralgia," *J. Headache Pain* 6(4):237-239.

Tsavaris, N. et al. (2006). "Analgesic Activity of High-Dose Intravenous Calcitonin in Cancer Patients with Bone Metastases," *Oncol. Rep.* 16(4):871-875.

(56) References Cited

OTHER PUBLICATIONS

Tseng, L.F. (2002). "Recent Advances in the Search for the μ-Opioidergic System: The Antinociceptive Properties of Endomorphin-1 and Endomorphin-2 in the Mouse," *Jpn. J. Pharmacol.* 89:216-220.

Tzabazis, A. et al. (2005). "Differential Activation of Trigeminal C or Aσ Nociceptors by Infrared Diode Laser in Rats: Behavioral Evidence," *Brain Res.* 1037:148-156.

Uhl-Bronner, S. et al. (2005). "Sexually Dimorphic Expression of Oxytocin Binding Sites in Forebrain and Spinal Cord of the Rat," *Neuroscience* 135(1):147-154.

Uryvaev, Y.V. et al. (Nov. 1996). "Extremely Low Doses of Oxytocin Reduce Pain Sensitivity in Men," *Bulletin of Experimental Biology and Medicine* 122(5):1071-1073. (Translated from *Byulleten' Eksperimental'noi Biologii i Meditsiny*, 122(11):487-489, Nov. 1996.)

Van Rossum, D. et al. (Sep. 1997). "Neuroanatomical Localization, Pharmacological Characterization and Functions of CGRP, Related Peptides and Their Receptors," *Neurosci. Biohehav. Rev.* 21(5):649-678.

Viney, C. (Jun. 2001). "Nasal Drug Delivery: A Review," *Indian Drugs* 38(6):283-287.

Visser, E.J. et al. (Oct. 2006). "Salmon Calcitonin in the Treatment of Post Herpetic Neuralgia," *Anaesth. Intensive Care* 34(5):668-671.

Wall, G.C. et al. (Apr. 1999). "Calcitonin in Phantom Limb Pain," *Ann. Pharmacother.* 33(4):499-501.

Wang, Y-C. J. et al. (Nov.-Dec. 1980). "Review of Excipients and pH's for Parenteral Products Used in the United States," *J. Parent Drug. Assn.* 34(6):452-462.

Wang, Y-C. J. et al. (1988). "Parenteral Formulations of Proteins and Peptides: Stability and Stabilizers," *J. Parent Sci. and Tech.* 42(2S):S4-S26.

Wang, J-W. et al. (2003). "Antinociceptive Role of Oxytocin in the Nucleus Raphe Magnus of Rats, an Involvement of μ-opioid Receptor," *Regul. Pept.* 115:153-159.

Weeke, J. et al. (1992). "A Randomized Comparison of Intranasal and Injectable Octreotide Administration in Patients With Acromegaly," *The Journal of Clinical Endocrinology and Metabolism* 75(1):163-169.

Wermeling, D.P. et al. (Nov. 4, 2005). "Analgesic Effects of Intranasal Butorphanol Tartrate Administered via a Unit-Dose Device in the Dental Impaction Pain Model: A Randomized, Double-Blind, Placebo-Controlled, Parallel-Group Study," *Clinical Therapeutics* 27(4):430-440.

Whitfield, M.F. et al. (1980). "Accidental Administration of Syntometrine in Adult Dosage to the Newborn," *Arch. Dis. Child.* 55:68-70.

Wiesenfeld-Hallin, Z. et al. (Sep. 17, 1984). "Subarachnoid Injection of Salmon Calcitonin Does Not Induce Analgesia in Rats," *Eur. J. Pharmacol.* 104(3-4):375-377.

Williams, G. et al. (Oct. 30, 1986). "Improvement in Headache Associated with Prolactinoma During Treatment with a Somatostatin Analogue: an "N of 1" Study," *The New England Journal of Medicine* 315(18):1166-1167.

Williams, G. et al. (Jul. 25, 1987). "Analgesic Effect of Somatostatin Analogue (Octreotide) in Headache Associated with Pituitary Tumours," *British Medical Journal (Clinical Research Ed.)* 295(6592):247-248.

Windle, R.J. et al. (Mar. 24, 2004). "Oxytocin Attenuates Stress-Induced c-fos mRNA Expression in Specific Forebrain Regions Associated with Modulation of Hypothalamo-Pituitary-Adrenal Activity," *J. Neurosci.* 24(12):2974-2982.

Wisniewski, K. (Mar. 7, 2014), "New, Potent, and Selective Peptidic Oxytocin Receptor Agonists", *J. Med. Chem.* 57:5306-5317.

Witt, D.M. (Jan. 15, 1997). "Regulatory Mechanisms of Oxytocin-Mediated Sociosexual Behavior," *Ann. N.Y. Acad. Sci.* 807:287-301.

Woodhouse, D.R. (Jan. 12, 1980.) "Water Intoxication Associated with High Dose Syntocinon Infusion," *Med. J. Aust.* 1(1):34.

Written Opinion Mailed on May 2, 2016, for PCT Application No. PCT/US2016/012512, Internationally Filed on Jan. 7, 2016, 5 Pages.

Yang, J. (Apr. 15, 1994). "Intrathecal Administration of Oxytocin Induces Analgesia in Low Back Pain Involving the Endogenous Opiate Peptide System," *Spine* 19(8):867-871.

Yang, Q. et al. (2002). "Modulation by Oxytocin of ATP-Activated Currents in Rat Dorsal Root Ganglion Neurons," *Neuropharmacology* 43:910-916.

Yeomans et al. Cephalalgia 2013, 33(8 supplement) 1-291, p. 58-59.

Young, E.A. (2001)."Effects of Estrogen Antagonists and Agonists on the ACTH Response to Restraint Stress in Female Rats," *Neuropsychopharmacology* 25(6):881-891.

Yu, S-Q. et al. (Sep. 5, 2003). "Involvement of Oxytocin in Spinal Antinociception in Rats with Inflammation," *Brain Res.* 983:13-22.

Zadina, J.E. et al. (Apr. 3, 1997). "A Potent and Selective Endogenous Agonist for the μ-Opiate Receptor," *Nature* 386:499-502.

Zubrzycka, M. et al. (Feb. 21, 2005). "Inhibition of Trigemino-Hypoglossal Reflex in Rats by Oxytocin in Mediated by μ and κ Opioid Receptors," *Brain Res.* 1035(1):67-72.

\* cited by examiner

MAGNESIUM-CONTAINING OXYTOCIN FORMULATIONS AND METHODS OF USE

CROSS REFERENCE TO RELATED APPLICATIONS

This application claims priority to U.S. Provisional Patent Application No. 62/100,862, filed Jan. 7, 2015, the disclosure of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 623632001000SEQLIST.TXT, date recorded: Oct. 7, 2016, size: 1 KB).

FIELD OF THE INVENTION

The invention relates to compositions comprising an oxytocin peptide and a magnesium salt. Also disclosed are methods for the treatment of pain (such as migraine headache) comprising co-administration of an oxytocin peptide and a magnesium salt.

BACKGROUND OF THE INVENTION

Oxytocin is a naturally occurring nine-amino acid neuropeptide that is primarily produced in the paraventricular and supraoptic nuclei of the mammalian hypothalamus. It is released in to the central nervous system via distributed neural pathways and in to peripheral circulation via the posterior pituitary. The intramuscular injection or intravenous infusion of synthetic oxytocin (Pitocin®) is currently approved in the U.S. to produce or improve uterine contractions to facilitate vaginal delivery and to control postpartum hemorrhage. Intranasal oxytocin (Syntocinon®) had been approved in the U.S. for stimulating milk letdown to facilitate breast-feeding from 1960 until 1997. While the nasal spray of Syntocinon® was withdrawn from the U.S. market at the request of the manufacturer, intranasal oxytocin is still marketed outside of the United States in countries such as Switzerland, Portugal, or Brazil. Use of oxytocin peptides in treatment of pain such as headache pain by intranasal administration has recently been demonstrated. See WO 2007/025249 A2 and WO 2007/025286 A2, the disclosures of which are incorporated herein by reference.

Pain is a perception mediated, in part, by the activation of certain brain structures. Pain is usually initiated when specialized neurons, termed nociceptors, which innervate the skin or other peripheral tissue, are activated by mechanical, thermal, chemical or other noxious stimuli. Pain is also experienced when peripheral or central neuronal structures involved in the processing of pain become hyperactive, e.g. as a result of trauma, ischemia or inflammation. Other causes of pain include disease-specific processes, metabolic disturbances, muscle spasm, and the onset of a neuropathic event or syndrome. Despite a wide range of available medical treatments including non-opioids (such as acetaminophen and non-steroidal anti-inflammatory drugs or NSAIDs), opioids, and co-analgesics (e.g. gabapentin), pain continues to afflict millions of individuals in the US alone and remains a profound burden to patients, health care, and business.

Oxytocin has been shown to reduce pain, in particular chronic pain, associated with the trigeminal nerve, such as trigeminal neuralgia and migraine headache. Human clinical trials have demonstrated efficacy of intranasal oxytocin in treating migraine headache. However, these trials have shown that the latency to analgesia caused by nasal oxytocin is around 2 hours, with the maximal analgesic effect not occurring until about 4 hours after dosing. Thus, there exists a need for an oxytocin peptide formulation capable of faster on-set of the analgesic effect.

BRIEF SUMMARY OF THE INVENTION

Provided are methods and compositions comprising an oxytocin peptide and a magnesium salt for treating pain via craniofacial mucosal administration (e.g., intranasal administration). The methods and magnesium containing oxytocin peptide formulations described herein provide faster, stronger and longer lasting analgesic effect compared to oxytocin alone.

In one aspect, the invention provides a method for treating pain comprising administering to a subject in need thereof an effective dose of an oxytocin peptide and a magnesium salt, wherein co-administration of the oxytocin peptide and the magnesium salt produces a synergistic analgesia. The oxytocin peptide and the magnesium salt may be co-administered concurrently or sequentially. In some embodiments, the oxytocin peptide is administered concurrently with the magnesium salt either in the same unit dose or in separate unit doses or formulations. In some embodiments, the oxytocin peptide and the magnesium salt are administered sequentially. For example, the oxytocin peptide is administered at a time period after administration of the magnesium salt. In some embodiments, the subject is a human.

The oxytocin peptide and the magnesium salt may be administered via the same route or different routes to a subject in need thereof. In some embodiments, the oxytocin peptide is administered via craniofacial mucosal administration (e.g., nasal, buccal, sublingual or ocular administration). In one embodiment, the oxytocin peptide and the magnesium salt are both administered intranasally in the same formulation.

In some embodiments, the oxytocin peptide is human oxytocin consisting of Cys-Tyr-Ile-Gln-Asn-Cys-Pro-Leu-Gly (SEQ. ID NO:1). In some embodiments, the effective dose of the oxytocin peptide is about 0.5 µg to about 2000 µg, preferably about 8 µg to about 1000 µg, more preferably about 15 µg to about 120 µg. In some embodiments, the effective dose of the magnesium salt administered provides about 50 µg to about 68 mg of magnesium, preferably about 50 µg to about 34 mg of magnesium, more preferably about 1 mg to about 3 mg of magnesium. In some embodiments, the magnesium salt comprises magnesium citrate and/or magnesium chloride administered in an amount to provide about 50 µg to about 68 mg of magnesium, or about 50 µg to about 34 mg of magnesium, or about 1 mg to about 3 mg of magnesium. In some embodiments, the magnesium salt is magnesium citrate or magnesium chloride administered in an amount to provide about 50 µg to about 68 mg of magnesium, or about 50 µg to about 34 mg of magnesium, or about 1 mg to about 3 mg of magnesium. In some embodiments, the effective dose of the magnesium salt is about 0.48 mg to about 600 mg of magnesium citrate, preferably about 0.48 mg to about 300 mg of magnesium citrate, more preferably about 10 mg to about 30 mg of magnesium citrate. In some embodiments, the effective dose of the oxytocin peptide and the magnesium salt comprises about 0.5 µg to about 2000 µg, or about 15 µg to about 120 µg (e.g., about 66 µg) of the oxytocin peptide administered in an aqueous solution containing about 1% to about 25% (preferably about 10% to about 14%, e.g. about 12%) (w/v) magnesium citrate. In some embodiments, the effective dose of the oxytocin peptide and the magnesium salt comprises about 0.5 µg to about 2000 µg, or about 15 µg to about 120 µg (e.g., about 60 µg or about 66 µg) of the oxytocin peptide administered in an aqueous solution containing about 0.11% to about 2.8% (preferably about 1.1% to about 1.6%, e.g. about 1.36%) (w/v) magnesium.

In some embodiments, the pain treatable by the method includes any pain treatable by oxytocin peptide, such as orofacial and craniofacial (e.g., headache pain), neck pain (e.g. occipital neuralgia), shoulder pain, or pain in the upper extremities. In some embodiments, the pain is a chronic pain, acute pain, or episodic pain. In some embodiments, the pain is a head or facial pain. In some embodiments, the pain is a trigeminal nerve-associated pain. In some embodiments, the pain is a migraine headache. In some embodiments, the pain is a cervical nerve-associated pain.

In one embodiment, the invention provides a method for treating migraine headache comprising administering (e.g., intranasally) to a subject in need thereof an effective dose of an oxytocin peptide and a magnesium salt, wherein co-administration of the oxytocin peptide and the magnesium salt produces a synergistic analgesia.

In one aspect, the invention provides a magnesium-containing oxytocin peptide formulation and uses thereof in the treatment of pain. Thus, provided is a composition comprising an oxytocin peptide and a magnesium salt, wherein the oxytocin peptide and the magnesium salt are in an amount that produces a synergistic analgesia when used in the treatment of pain. In some embodiments, the oxytocin peptide is human oxytocin consisting of Cys-Tyr-Ile-Gln-Asn-Cys-Pro-Leu-Gly (SEQ. ID NO:1). In some embodiments, the magnesium salt comprises magnesium citrate and/or magnesium chloride. In some embodiments, the magnesium salt comprises magnesium citrate and magnesium chloride. In some embodiments, the magnesium salt is magnesium citrate or magnesium chloride. In some embodiments, the composition is a liquid formulation comprising between about 0.01 mg/mL and about 16 mg/mL (preferably between about 0.1 mg/mL and about 2 mg/mL, more preferably between about 0.15 mg/mL and about 1.5 mg/mL, or about 0.33 mg/mL) of the oxytocin peptide. In some embodiments, the composition is a liquid formulation comprising the magnesium salt in an amount to provide between about 1 mg/mL and about 30 mg/mL (or between about 5 mg/mL and about 30 mg/mL, between about 10 mg/mL and about 30 mg/mL, preferably between about 11 mg/mL and about 15 mg/mL, or about 13 mg/mL, or about 12 mg/mL) of magnesium. In some embodiments, the composition further comprises one or more excipients, vehicles, emulsifiers, stabilizers, preservatives, mucosal adhesives, antibacterial agents, buffers, and/or other additives. In some embodiments, the composition has a pH of about 2 to about 7 (preferably about 4.5). In some embodiments, the composition further comprises a pharmaceutically acceptable carrier.

In some embodiments, provided is a pharmaceutical composition comprising an oxytocin peptide and a magnesium salt, and a pharmaceutically acceptable carrier, wherein the oxytocin peptide and the magnesium salt are in an amount that produces a synergistic analgesia when used in the treatment of pain.

In some embodiments, the composition is adapted for craniofacial mucosal administration (e.g., nasal, buccal, sublingual or ocular administration). In some embodiments, the composition is adapted for intranasal administration, which may further comprise a device for intranasal administration, such as a nasal pump apparatus, e.g., a nasal pump apparatus comprising a reservoir bottle attached to an aerosolizer. In some embodiments, the nasal pump apparatus comprises one of more of the following: (i) a filter for preventing back flow, (ii) a metal-free fluid path, and (iii) a plastic material stable to gamma-radiation. In some embodiments, the nasal pump apparatus provides a metered dose (e.g., about 50 to about 150 µL per spray, or about 50 µL per spray).

Also provided is a method for treating pain in a subject in need thereof comprising intranasally administering to a subject in need thereof an effective dose of a magnesium-containing oxytocin peptide formulation described herein.

Further provided is a magnesium-containing oxytocin peptide formulation described herein for use in a method of treating pain in a subject in need thereof. Also provided is a use of a magnesium-containing oxytocin peptide formulation described herein in the manufacture of a medicament for the treatment of pain.

Also provided is a kit comprising a magnesium-containing oxytocin peptide formulation described herein contained in a device for intranasal administration such as a nasal pump apparatus and suitable packaging. The kit may further comprise instructions for administering the magnesium-containing oxytocin peptide formulation in a subject in need thereof.

DETAILED DESCRIPTION OF THE INVENTION

Figure 1:
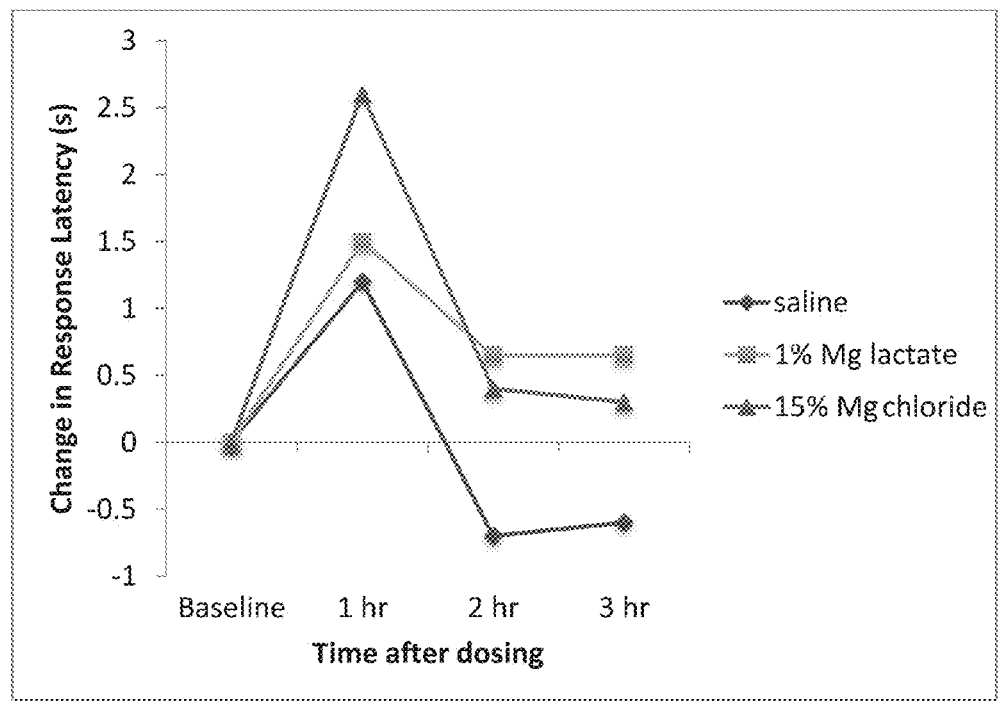
FIG. 1. Effect of magnesium chloride or magnesium lactate in a rat model of facial thermal nociception. Rats were treated with saline, 15% magnesium chloride or 1% magnesium lactate, and withdrawal response latency was measured just prior to treatment and at 1, 2 and 3 hours post-treatment.

The invention provides, inter alia, compositions comprising an oxytocin peptide and a magnesium salt and methods for treatment of pain by craniofacial administration (e.g., intranasal administration) of the magnesium-containing oxytocin peptide formulations.

DEFINITIONS

As used herein, unless otherwise specified, the term "treatment" or "treating pain" refers to administration to a subject of an agent of interest wherein the agent alleviates pain or prevents a painful pathology for which the subject is being treated.

Although analgesia in the strictest sense is an absence of pain, as used herein, "analgesia" or "analgesic effect" refers to reduction in pain perceived by a subject, including reduction of hyperalgesia and/or allodynia. "Analgesia" or "analgesic effect" also includes reduction in pain frequency.

"Analgesia agent", "analgesic agent" or "analgesic" refers to any biomolecule, drug or active agent that alleviates or prevents, or reduces the frequency of pain episodes.

"Synergism", "synergy" or "synergistic effect" refers to a joint action of two or more compounds in such a manner that one supplements or enhances the action of the other to produce an effect greater than that which would be predicted or expected by adding the effects of given doses of two or more compounds if given individually. When two or more analgesic agents, used in combination, produces an overall decrease in pain intensity or sensitivity to painful stimulation (allodynia and/or hyperalgesia) that is greater than individual analgesia or analgesic effects of any of them in equivalent quantities that would be expected or predicted by summing the effects of the individual agents, it is said that a "synergistic analgesia" or "synergistic analgesic effect" is achieved. When use of two or more analgesic agents in combination results in faster onset of analgesia or analgesic effect and/or longer lasting analgesia or analgesic effect than would occur following administration of the individual analgesic agents used alone in equivalent quantities, a "synergistic analgesia" or "synergistic analgesic effect" is considered achieved also.

"Acute pain" refers to rapid onset pain from a specific cause (injury, infection, inflammation, etc.) that has lasted for a limited period of time (as opposed to chronic pain). "Chronic pain" refers to a persistent state of pain. Chronic pain is often associated with long-term incurable or intractable medical conditions or diseases. Chronic pain can also refer to pain states that occur with high frequency. For example, people are considered to have "chronic migraine" if they experience 15 or more days with headache per month. "Episodic pain" refers to pain that occurs repeatedly but occasionally. For example, people who experience episodic migraine headaches can go weeks and months between migraine attacks.

"Craniofacial mucosal administration" refers to delivery to the mucosal surfaces of the nose, nasal passageways, nasal cavity; the mucosal surfaces of the oral cavity including the gingiva (gums), the floor of the oral cavity, the lips, the tongue, the sublingual oral surfaces, including the frenulum of tongue and the floor of the mouth, and the mucosal surfaces of or around the eye including the conjunctiva, the lacrimal gland, the nasolacrimal ducts, and the mucosa of the upper or lower eyelid and the eye.

"Intranasal administration" or "administered intranasally" refers to delivery to the nose, nasal passageways or nasal cavity by spray, drops, powder, gel, film, inhalant or other means.

The "inferior region of the nasal cavity" refers generally to the portion of the nasal cavity where the middle and inferior turbinate bones protrude and is a region of the nasal cavity that is significantly innervated by the trigeminal nerve. The "superior region of the nasal cavity" is defined by the upper third and cribriform plate region wherein olfactory innervation is located.

A "subject" or "patient" as used herein refers to a mammal, including but not limited to a human. Mammals include, but are not limited to, farm animals (such as cows), sport animals, pets (such as guinea pigs, cats, dogs, rabbits and horses), primates, mice and rats. In one embodiment, a subject is a human.

As used herein, "oxytocin peptide" refers to a substance having biological activity associated with natural oxytocin. Oxytocin peptide can be a naturally occurring endogenous peptide, fragments, analogues or derivatives thereof. Oxytocin peptide can also be a non-endogenous peptide, fragments, analogues or derivatives thereof. In one aspect, the oxytocin peptide is human oxytocin. In other aspects, the oxytocin peptide may be an analogue or derivative of human oxytocin.

As used herein, an "analogue" or "derivative" refers to any peptide analogous to naturally occurring oxytocin wherein one or more amino acids within the peptide have been substituted, deleted, or inserted. The term also refers to any peptide wherein one or more amino acids (for example one, two or three amino acids) have been modified, for example by chemical modification. In general, the term covers all peptides which exhibit oxytocin activity but which may, if desired, have a different potency or pharmacological profile.

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

Where a range of values is provided, it is intended that each intervening value between the upper and lower limit of that range and any other stated or intervening value in that stated range is encompassed within the disclosure. For example, if a range of 1 μg to 8 μg is stated, it is intended that 2 μg, 3 μg, 4 μg, 5 μg, 6 μg, and 7 μg are also explicitly disclosed, as well as the range of values greater than or equal to 1 μg and the range of values less than or equal to 8 μg. If a range of 10-14% is stated, it is intended that 10%, 11%, 12%, 13%, and 14% are also explicitly disclosed. Furthermore, each smaller range in a stated range between any stated value or intervening value and any other stated or intervening value in that stated range is encompassed within the disclosure. The upper and lower limits of these smaller ranges may independently be included or excluded in the range, and each range where either, neither, or both limits are included in the smaller ranges is also encompassed within the disclosure, subject to any specifically excluded limit in the stated range. Where the stated range includes one or both of the limits, ranges excluding either or both of those included limits are also included in the disclosure.

Oxytocin Peptide

Oxytocin was one of the first peptide hormones to be isolated and sequenced. Natural oxytocin is a nine amino acid cyclic peptide hormone with two cysteine residues that form a disulfide bridge between positions 1 and 6. The amino acid sequence for human oxytocin is Cys-Tyr-Ile-Gln-Asn-Cys-Pro-Leu-Gly (SEQ ID NO:1).

There are processes described for the production of oxytocin, see for example U.S. Pat. No. 2,938,891 and U.S. Pat. No. 3,076,797; in addition, oxytocin is commercially available. A variety of peptide analogues and derivatives are available and others can be contemplated for use within the invention and can be produced and tested for biological activity according to known methods. Oxytocin analogues may include, but are not limited to, 4-threonine-1-hydroxy-deaminooxytocin, 4-serine-8-isoleucine-oxytocin, 9-deamidooxytocin, 7-D-proline-oxytocin and its deamino analogue, (2,4-diisoleucine)-oxytocin, deamino oxytocin analogue, 1-deamino-1-monocarba-E12-Tyr(OMe)]-OT(dCOMOT), 4-threonine-7-glycine-oxytocin (TG-OT), oxypressin, deamino-6-carba-oxytoxin (dC60), L-371,257 and the related series of compounds containing an ortho-trigluoro-ethoxyphenylacetyl core such as L-374,943. Other exemplary oxytocin analogues include 4-threonine-1-hydroxy-deaminooxytocin, 9-deamidooxytocin, an analogue of oxytocin containing a glycine residue in place of the glycinamide residue, 7-D-proline-oxytocin (2,4-diisoleucine)-oxytocin, an analogue of oxytocin with natriuretic and diuretic activities, deamino oxytocin analogue; a long-acting oxytocin analogue, 1-deamino-1-monocarba-E12-[Tyr (OMe)]-OT(dCOMOT), carbetocin, (1-butanoic acid-2-(O-methyl-L-tyrosine)-1-carbaoxytocin, deamino-1 mono-carba-(2-O-methyltyrosine)-oxytocin [d(COMOT)]), [Thr4-Gly7]-oxytocin (TG-OT), oxypressin, Ile-conopressin, deamino-6-carba-oxytoxin (dC60), d[Lys(8)(5/6C-Fluorescein)]VT, d[Thr(4), Lys(8)(5/6C-Fluorescein)]VT, [HO(1)] [Lys(8)(5/6C-Fluorescein)]VT, [HO(1)][Thr(4), Lys(8)(5/6C-Fluorescein)]VT, d[Om(8)(5/6C-Fluorescein)]VT, d[Thr (4), Om(8)(5/6C-Fluorescein)]VT, [HO(1)][Om(8)(5/6C-Fluorescein)]VT, [HO(1)][Thr(4), Om(8)(5/6C-Fluorescein)]VT, and 1-deamino-oxytocin in which the disulfide bridge between residues 1 or 6 is replaced by a thioether, and desamino-oxytocin analogues in which the disulfide bond is replaced by a diselenide bond, a ditelluride bond, a telluroseleno bond, a tellurosulfide bond or a selenosulfide bond (e.g., the peptide analogues of oxytocin described in PCT patent application WO 2011/120,071, incorporated herein by reference). Peptides for use within the invention can be peptides that are obtainable by partial substitution, addition, or deletion of amino acids within a naturally occurring or native peptide sequence. Peptides can be chemically modified, for example, by amidation of the carboxyl terminus (—NH$_2$), the use of D amino acids in the peptide, incorporation of small non-peptidyl moieties, as well as the modification of the amino acids themselves (e.g. alkylation or esterification of side chain R-groups). Such analogues, derivatives and fragments should substantially retain the desired biological activity of the native oxytocin peptide. In some embodiments, the oxytocin analogue is 4-serine-8-isoleucine-oxytocin or 9-deamidooxytocin. In some embodiments, the oxytocin analogue is carbetocin. The present disclosure also embrace other known oxytocin analogs, for example, the peptidic oxytocin receptor agonists described in PCT patent application WO 2012/042371 and Wiśniewski, et al. *J Med Chem.* 2014, 57:5306-5317, the entire content of which is incorporated herein by reference. In some embodiments, the oxytocin analogue is a compound selected from Compound Nos. 1-65 described in Tables 1-3 in Wiśniewski, et al. *J Med Chem.* 2014, 57:5306-5317. In some embodiments, the oxytocin analogue is a selected from the group consisting of Compound No. 31 ([2-ThiMeGly7] dOT), Compound No. 47 (carba-6-[Phe2,BuGly7]dOT), Compound No. 55 (carba-6-[3-MeBzlGly7]dOT) and Compound No. 57 (carba-1-[4-FBzlGly7]dOT, also referred to as merotocin).

In some embodiments, oxytocin or an oxytocin analogue is isotopically labeled by having one or more atoms replaced by an isotope having a different atomic mass. Examples of isotopes that may be incorporated into the disclosed compounds include isotopes of hydrogen (e.g., $^2$H and $^3$H), carbon (e.g., $^{13}$C and $^{14}$C), nitrogen (e.g., $^{15}$N), oxygen (e.g., $^{18}$O and $^{17}$O), phosphorus (e.g., $^{31}$P and $^{32}$P), fluorine (e.g., $^{18}$F), chlorine (e.g., $^{36}$Cl) and sulfur (e.g. $^{35}$S). The isotopically labeled compound may be administered to a subject or other subject and subsequently detected, yielding useful diagnostic and/or therapeutic management data, according to conventional techniques. Further, the isotopically labeled compound may be administered to a subject or other subject in need thereof, yielding therapeutically advantageous absorption, distribution, metabolism and/or elimination profiles. All isotopic variations of the oxytocin peptide, e.g. human oxytocin or an analogue or derivative thereof, whether radioactive or not, are contemplated.

In some embodiments, the oxytocin peptide is human oxytocin consisting of Cys-Tyr-Ile-Gln-Asn-Cys-Pro-Leu-Gly (SEQ. ID NO:1).

An "international unit" (IU, UI or IE) is an internationally accepted unit of activity used to quantify vitamins, hormones and vaccines. It defines the amount of a substance that gives a unit of activity as determined using a defined biological assay in order to standardize preparations from multiple source materials. Similarly, a USP unit is a defined dosage unit established by the United States Pharmacopeia in cooperation with the Food and Drug Administration in order to ensure the identity, strength, quality, purity and consistency of a drug product. In general, USP units are equal to International Units, due to harmonization efforts. By convention, for oxytocin, 1 unit of activity is generally defined as equal to approximately 2 micrograms of synthetic oxytocin peptide; or 1 mg is equal to 500 units (Stedman's Medical Dictionary). Therefore, as used herein, one "IU" or "International Unit" of an oxytocin peptide is the amount of the oxytocin peptide that has the same biological activity or produces the same level of a biological effect (e.g. contractile response of rat uterine strips) as approximately 2 micrograms of the synthetic peptide. An analogue with weaker activity would require more material to achieve the same level of biological effect. Determinations of drug potency are well known to those skilled in the art and may include either in vitro or in vivo assays using synthetic oxytocin as a reference. Atke and Vilhardt *Acta Endocrinol* 1987: 115(1):155-60; Engstrom et al. *Eur J Pharmacol* 1998: 355(2-3):203-10.

Magnesium-Containing Oxytocin Peptide Formulations

In one aspect, the invention provides a magnesium-containing oxytocin peptide formulation and uses thereof in the treatment of pain.

Magnesium is involved in many aspects of life and health such as energy production, oxygen uptake, central nervous system function, electrolyte balance, glucose metabolism and muscle activity. Magnesium has also been found clinically effective in decreasing pain, such as muscle pain and nerve pain. Magnesium salts have been found to be analgesic when given intravenously and when applied directly onto the spinal cord of rats and humans. The mechanisms underlying these effects are unclear, but are likely to involve either noncompetitive blockade of the N-methyl D-aspartate (NMDA) neurotransmitter receptor, or an increase in affinity of the oxytocin receptor action as an allosteric modulator, or both.

Oxytocin has been known to treat head and craniofacial pain in humans and rats, and in the upper extremities of rats when administered intranasally, being particularly effective in the treatment of chronic pain where oxytocin receptors are overexpressed. However, it has been observed that the analgesic effect of oxytocin in treating head pain, for example, migraine headache pain in human patients, does not occur immediately after administration. Rather an initial period of up to 2 hours is required before onset of significant analgesia and 4 hours to maximal analgesic effect, while the patient continues to suffer from the pain during this initial period. The inventor has found by surprise that co-administration of oxytocin and a magnesium salt can result in an unexpected synergistic reduction in pain intensity as well as a faster onset and longer duration of the analgesic effect.

Thus, provided is a composition comprising an oxytocin peptide and a magnesium salt, wherein the oxytocin peptide and the magnesium salt are in an amount that produces a synergistic analgesia when used in the treatment of pain. The composition is capable of producing one or more of the following results when used for treating pain in a subject in need thereof: (i) an overall analgesia or analgesic effect (reduction of pain intensity and/or sensitivity to painful stimulation (allodynia and/or hyperalgesia)) that is greater than the sum of analgesia or analgesic effects of the equivalent amounts of the oxytocin peptide and the magnesium salt given individually; (ii) reduction of the frequency of the pain experienced by the subject that is greater than the sum of the reduction of the pain frequency by the equivalent amounts of the oxytocin peptide and the magnesium salt given individually; (iii) faster onset of analgesia or analgesic effect than any of the equivalent amounts of the analgesic agents given alone; and/or (iv) longer lasting analgesia or analgesic effect than any of the equivalent amounts of the analgesic agents given alone. In some embodiments, the composition comprises an oxytocin peptide and a magnesium salt, wherein the oxytocin peptide and the magnesium salt are in an amount that produces one or more of results (i)-(iv).

The relative proportion of the oxytocin peptide and the magnesium in the magnesium-containing oxytocin peptide formulation is important in achieving optimal synergistic analgesia. The optimal amounts of the oxytocin peptide and the magnesium salt may depend on the specific pain-type, the type of synergistic effect desired, and other factors such as the route of administration. For example, the amount of magnesium may be important to achieve a faster onset of analgesia; the amount of oxytocin may be important to achieve a longer-lasting analgesia and the relative ratio between oxytocin and magnesium may be important to achieve maximum reduction in pain intensity.

In some embodiments, the magnesium-containing oxytocin peptide formulation or composition is a liquid formulation comprising between about 0.01 mg/mL and about 16 mg/mL of the oxytocin peptide. In some embodiments, the magnesium-containing oxytocin peptide formulation or composition comprises between about 0.01 mg/mL and about 12 mg/mL, between about 0.05 mg/mL and about 16 mg/mL, between about 0.1 mg/mL and about 12 mg/mL, between about 0.1 mg/mL and about 8 mg/mL, between about 0.1 mg/mL and about 4 mg/mL, between about 0.1 mg/mL and about 2 mg/mL, between about 0.1 mg/mL and about 1.6 mg/mL, between about 0.1 mg/mL and about 1.2 mg/mL, between about 0.1 mg/mL and about 1 mg/mL, between about 0.1 mg/mL and about 0.8 mg/mL, between about 0.1 mg/mL and about 0.4 mg/mL, between about 0.1 mg/mL and about 0.3 mg/mL, between about 0.2 mg/mL and about 16 mg/mL, between about 0.2 mg/mL and about 12 mg/mL, between about 0.2 mg/mL and about 10 mg/mL, between about 0.2 mg/mL and about 8 mg/mL, between about 0.2 mg/mL and about 6 mg/mL, between about 0.2 mg/mL and about 4 mg/mL, between about 0.2 mg/mL and about 2 mg/mL, between about 0.2 mg/mL and about 1.6 mg/mL, between about 0.2 mg/mL and about 1.2 mg/mL, between about 0.2 mg/mL and about 1 mg/mL, between about 0.2 mg/mL and about 0.8 mg/mL, between about 0.2 mg/mL and about 0.6 mg/mL, between about 0.2 mg/mL and about 0.4 mg/mL, between about 0.2 mg/mL and about 0.3 mg/mL, between about 0.3 mg/mL and about 16 mg/mL, between about 0.3 mg/mL and about 12 mg/mL, between about 0.3 mg/mL and about 10 mg/mL, between about 0.3 mg/mL and about 8 mg/mL, between about 0.3 mg/mL and about 4 mg/mL, between about 0.3 mg/mL and about 3 mg/mL, between about 0.3 mg/mL and about 1 mg/mL, between about 0.3 mg/mL and about 0.5 mg/mL, between about 0.5 mg/mL and about 16 mg/mL, between about 0.5 mg/mL and about 10 mg/mL, between about 0.5 mg/mL and about 5 mg/mL, between about 0.5 mg/mL and about 1 mg/mL, between about 1 mg/mL and about 16 mg/mL, between about 1 mg/mL and about 10 mg/mL, or between about 1 mg/mL and about 5 mg/mL of the oxytocin peptide. In a preferred embodiment, the magnesium-containing oxytocin peptide formulation or composition comprises between about 0.1 mg/mL and about 2 mg/mL, between about 0.15 mg/mL and about 1.5 mg/mL, or between about 0.2 mg/mL and about 1.2 mg/mL of the oxytocin peptide. In one embodiment, the oxytocin peptide is human oxytocin consisting of Cys-Tyr-Ile-Gln-Asn-Cys-Pro-Leu-Gly (SEQ. ID NO:1).

In some embodiments, the magnesium-containing oxytocin peptide formulation or composition is a liquid formulation comprising between about 5 IU/mL and about 8000 IU/mL of the oxytocin peptide. In some embodiments, the magnesium-containing oxytocin peptide formulation or composition comprises between about 500 IU/mL and about 6000 IU/mL, between about 25 IU/mL and about 8000 IU/mL, between about 50 IU/mL and about 6000 IU/mL, between about 50 IU/mL and about 4000 IU/mL, between about 50 IU/mL and about 2000 IU/mL, between about 50 IU/mL and about 1000 IU/mL, between about 50 IU/mL and about 800 IU/mL, between about 50 IU/mL and about 600 IU/mL, between about 50 IU/mL and about 500 IU/mL, between about 50 IU/mL and about 400 IU/mL, between about 50 IU/mL and about 200 IU/mL, between about 50 IU/mL and about 150 IU/mL, between about 100 IU/mL and about 8000 IU/mL, between about 100 IU/mL and about 6000 IU/mL, between about 100 IU/mL and about 5000 IU/mL, between about 100 IU/mL and about 4000 IU/mL, between about 100 IU/mL and about 3000 IU/mL, between about 100 IU/mL and about 2000 IU/mL, between about 100 IU/mL and about 1000 IU/mL, between about 100 IU/mL and about 800 IU/mL, between about 100 IU/mL and about 600 IU/mL, between about 100 IU/mL and about 500 IU/mL, between about 100 IU/mL and about 400 IU/mL, between about 100 IU/mL and about 300 IU/mL, between about 100 IU/mL and about 200 IU/mL, between about 100 IU/mL and about 150 IU/mL, between about 150 IU/mL and about 8000 IU/mL, between about 150 IU/mL and about 6000 IU/mL, between about 150 IU/mL and about 5000 IU/mL, between about 150 IU/mL and about 4000 IU/mL, between about 150 IU/mL and about 2000 IU/mL, between about 150 IU/mL and about 1500 IU/mL, between about 150 IU/mL and about 500 IU/mL, between about 150 IU/mL and about 250 IU/mL, between about 250 IU/mL and about 8000 IU/mL, between about 250 IU/mL and about 5000 IU/mL, between about 250 IU/mL and about 2500 IU/mL, between about 250 IU/mL and about 500 IU/mL, between about 500 IU/mL and about 8000 IU/mL, between about 500 IU/mL and about 5000 IU/mL, or between about 500 IU/mL and about 2500 IU/mL of the oxytocin peptide. In a preferred embodiment, the magnesium-containing oxytocin peptide formulation or composition comprises between about 50 IU/mL and about 1000 IU/mL, between about 75 IU/mL and about 750 IU/mL, or between about 100 IU/mL and about 600 IU/mL of the oxytocin peptide. In one embodiment, the oxytocin peptide is human oxytocin consisting of Cys-Tyr-Ile-Gln-Asn-Cys-Pro-Leu-Gly (SEQ. ID NO:1).

Any magnesium salt (such as a water-soluble magnesium salt) may be used to provide magnesium in the magnesium-containing oxytocin peptide formulation of this invention provided that when used in treating pain, a synergistic analgesia is produced. The magnesium salt used in the magnesium-containing oxytocin peptide formulation may be selected based on a number of factors such as the amount of free magnesium ion that can be delivered when the formulation is administered, the solubility of the magnesium salt in the media for a liquid formulation, the acidity/basicity of the counter ion, and/or the dissociation constant of the salt. For example, in a liquid formulation, the magnesium salt needs to be sufficiently soluble in the liquid media to deliver the magnesium ion concentration required for producing synergistic analgesia with the oxytocin peptide. Other factors may also be considered when selecting the magnesium salt, such as compatibility with other substances in the formulation and ability of the counter ion to perform other functions in the formulation. For example, magnesium citrate is sufficiently soluble in an aqueous solution to provide the desirable amount of magnesium or desirable magnesium ion concentration; citrate salts are pharmaceutically acceptable; the citrate can be part of the buffering agents; and magnesium citrate may add a pleasant flavor for the formulation. The magnesium ions in the magnesium-containing oxytocin peptide formulation may be provided by using one or more magnesium salts. A magnesium salt in the magnesium-containing oxytocin peptide formulation may be a magnesium salt used initially in preparing of the magnesium-containing oxytocin peptide formulation, or formed in situ during preparation of the magnesium-containing oxytocin peptide formulation. For example, magnesium chloride may be used initially in preparing the formulation; and upon addition of citric acid to the formulation, magnesium citrate may be formed in situ. In such instance, the magnesium ions in the magnesium-containing oxytocin peptide formulation are provided by both magnesium chloride and magnesium citrate.

The magnesium salt used in the magnesium-containing oxytocin peptide formulation described herein can be obtained from commercial sources or prepared following methods known in the art. For example, magnesium citrate may be prepared following procedures described in Staszczuk P, et al. Physicochem Probl Mineral Proc 37: 149-158 (2003), U.S. Pat. No. 1,936,364 and U.S. Pat. No. 2,260,004).

Thus, in some embodiments, the magnesium-containing oxytocin peptide formulation or composition comprises magnesium citrate. The concentration of the magnesium salt may be measured by the concentration or percentage by weight of the salt or by the concentration of the equivalent concentration or amount of Mg or $Mg^{2+}$ provided by the salt. For a liquid formulation, percentage by weight (w/v) means the amount in grams of the magnesium salt in 100 mL of solution. For example, a 10% (w/v) magnesium citrate solution contains 10 g of magnesium citrate in 100 mL of the solution. If other magnesium salts are substituted for magnesium citrate the magnesium concentrations contemplated for use in the methods and formulations described herein are equivalent to those resulting from use of magnesium citrate at the amounts recited herein.

The amount of magnesium present in the formulation may also be expressed in percentage by weight (w/v) (grams of magnesium or $Mg^{2+}$ per 100 mL of solution), in mg/mL (milligrams of magnesium or $Mg^{2+}$ per milliliter of solution), or in molarity ("M"—defined as moles of magnesium or $Mg^{2+}$ per liter of the solution; or "mM"—defined as millimoles of magnesium or $Mg^{2+}$ per liter of the solution). The equivalent amount of magnesium or $Mg^{2+}$ (Atomic weight: 24.3) provided by a solution of magnesium citrate (anhydrous magnesium citrate dibasic, Molecular weight: 214.4) can be calculated as following:

$$[\% \ Mg^{2+}(w/v)] = (24.3/214.4) * [\% \ Mg \ Citrate \ (w/v)] = 0.113 * [\% \ Mg \ Citrate \ (w/v)]$$

$$mM \ Mg^{2+} = 411.5 * [\% \ Mg^{2+}(w/v)] = 46.6 * [\% \ Mg \ Citrate \ (w/v)]$$

$$mg/mL \ Mg^{2+} = 10 * [\% \ Mg^{2+}(w/v)] = 0.0243 * [mM \ Mg^{2+}] = 1.13 * [\% \ Mg \ Citrate \ (w/v)]$$

Table A provides correspondence of exemplary concentrations of magnesium citrate in percentage by weight (w/v) with the amount of magnesium or $Mg^{2+}$ in percentage by weight (w/v), mg/mL, and mM.

TABLE A

| % (w/v) of Mg Citrate | % (w/v) of Mg$^{2+}$ | mM of Mg$^{2+}$ | mg/mL of Mg$^{2+}$ |
|---|---|---|---|
| 1% | 0.11% | 47 mM | 1.1 mg/mL |
| 2% | 0.23% | 93 mM | 2.3 mg/mL |
| 3% | 0.34% | 140 mM | 3.4 mg/mL |
| 4% | 0.45% | 187 mM | 4.5 mg/mL |
| 5% | 0.57% | 233 mM | 5.7 mg/mL |
| 6% | 0.68% | 280 mM | 6.8 mg/mL |
| 7% | 0.79% | 326 mM | 7.9 mg/mL |
| 8% | 0.90% | 373 mM | 9.0 mg/mL |
| 9% | 1.02% | 420 mM | 10.2 mg/mL |
| 10% | 1.13% | 466 mM | 11.3 mg/mL |
| 11% | 1.24% | 513 mM | 12.4 mg/mL |
| 12% | 1.36% | 560 mM | 13.6 mg/mL |
| 13% | 1.47% | 606 mM | 14.7 mg/mL |
| 14% | 1.58% | 653 mM | 15.8 mg/mL |
| 15% | 1.70% | 700 mM | 17.0 mg/mL |
| 16% | 1.81% | 746 mM | 18.1 mg/mL |
| 17% | 1.92% | 793 mM | 19.2 mg/mL |
| 18% | 2.03% | 840 mM | 20.3 mg/mL |
| 19% | 2.15% | 886 mM | 21.5 mg/mL |
| 20% | 2.26% | 933 mM | 22.6 mg/mL |
| 21% | 2.37% | 979 mM | 23.7 mg/mL |
| 22% | 2.49% | 1026 mM | 24.9 mg/mL |
| 23% | 2.60% | 1073 mM | 26.0 mg/mL |
| 24% | 2.71% | 1119 mM | 27.1 mg/mL |
| 25% | 2.83% | 1166 mM | 28.3 mg/mL |

In some embodiments, the magnesium-containing oxytocin peptide formulation or composition is a liquid formulation comprising magnesium citrate in an amount to provide between about 1 mg/mL and about 30 mg/mL of magnesium. In some embodiments, the composition comprises magnesium citrate in an amount to provide between about 1 mg/mL and about 30 mg/mL of magnesium ions (Mg$^{2+}$). The amount of magnesium ions may include magnesium ions in any forms, for example, as magnesium ions in a solvate or in a coordination complex in a liquid formulation, or as magnesium ions in crystal lattice in a solid formulation. In some embodiments, the composition comprises one or more magnesium salts selected from the group consisting of magnesium chloride, magnesium citrate, magnesium sulfate and magnesium acetate in an amount to provide between about 11 mg/mL and about 15 mg/mL, or between about 400 mM and about 600 mM, of magnesium or magnesium ion. In some embodiments, the composition comprises magnesium chloride and/or magnesium citrate in an amount to provide between about 11 mg/mL and about 15 mg/mL, or between about 400 mM and about 600 mM, of magnesium or magnesium ion. In some embodiments, the composition comprises magnesium citrate in an amount to provide between about 11 mg/mL and about 15 mg/mL of magnesium or magnesium ion. In some embodiments, the composition comprises about 10 mg/mL to about 250 mg/mL of magnesium citrate (e.g., anhydrous magnesium citrate dibasic, MW 214.4). In some embodiments, the composition comprises about 1% to about 25% (w/v) of magnesium citrate (e.g., anhydrous magnesium citrate dibasic, MW 214.4). In some embodiments, the composition comprises about 1% to about 15%, about 1% to about 15%, about 1% to about 12%, about 1% to about 10%, about 1% to about 8%, about 1% to about 5%, about 2% to about 15%, about 3% to about 15%, about 4% to about 15%, about 4% to about 14%, about 4% to about 12%, about 4% to about 10%, about 4% to about 8%, about 5% to about 15%, about 5% to about 12%, about 5% to about 10%, about 8% to about 12%, about 8% to about 10%, about 10% to about 15%, about 10% to about 14%, about 10% to about 12%, about 11% to about 15%, or about 11% to about 13% (w/v) of magnesium citrate. In some embodiments, the composition comprises about 1%, about 2%, about 3%, about 4%, about 5%, about 6%, about 7%, about 8%, about 9%, about 10%, about 11%, about 12%, about 13%, about 14%, or about 15% (w/v) of magnesium citrate. In some embodiments, the magnesium-containing oxytocin peptide formulation or composition is a liquid formulation comprising between about 0.01 mg/mL and about 16 mg/mL (preferably between about 0.1 mg/mL and about 2 mg/mL, more preferably between about 0.15 mg/mL and about 1.5 mg/mL, or about 0.33 mg/mL) of the oxytocin peptide and about 1% to about 25% (preferably about 10% to about 14%, or about 12%) (w/v) of magnesium citrate. In some embodiments, the magnesium-containing oxytocin peptide formulation or composition is a liquid formulation comprising between about 0.5 IU/mL and about 8000 IU/mL (preferably between about 50 IU/mL and about 1000 IU/mL, more preferably between about 75 IU/mL and about 225 IU/mL, or about 150 IU/mL) of the oxytocin peptide and about 1% to about 25% (preferably about 10% to about 14%, or about 12%) (w/v) of magnesium citrate.

In some embodiments, the composition comprises magnesium chloride in an amount to provide between about 11 mg/mL and about 15 mg/mL of magnesium or magnesium ion. In some embodiments, the composition comprises about 10 mg/mL to about 250 mg/mL of magnesium chloride (e.g., magnesium chloride hexahydrate, MW 203.3). In some embodiments, the composition comprises about 1% to about 25% (w/v) of magnesium chloride hexahydrate (MgCl$_2$.6H$_2$O, MW 203.3). In some embodiments, the composition comprises about 1% to about 15%, about 1% to about 15%, about 1% to about 12%, about 1% to about 10%, about 1% to about 8%, about 1% to about 5%, about 2% to about 15%, about 3% to about 15%, about 4% to about 15%, about 4% to about 14%, about 4% to about 12%, about 4% to about 10%, about 4% to about 8%, about 5% to about 15%, about 5% to about 12%, about 5% to about 10%, about 8% to about 15%, about 8% to about 12%, about 8% to about 10%, about 10% to about 15%, about 10% to about 14%, about 10% to about 12%, about 11% to about 15%, or about 11% to about 13% (w/v) of magnesium chloride hexahydrate. In some embodiments, the composition comprises about 1%, about 2%, about 3%, about 4%, about 5%, about 6%, about 7%, about 8%, about 9%, about 10%, about 11%, about 12%, about 13%, about 14%, or about 15% (w/v) of magnesium chloride hexahydrate. In some embodiments, the magnesium-containing oxytocin peptide formulation or composition is a liquid formulation comprising between about 0.01 mg/mL and about 16 mg/mL (preferably between about 0.1 mg/mL and about 2 mg/mL, more preferably between about 0.15 mg/mL and about 1.5 mg/mL, or about 0.33 mg/mL) of the oxytocin peptide and about 1% to about 25% (preferably about 8% to about 12%, or about 10%) (w/v) of magnesium chloride hexahydrate. In some embodiments, the magnesium-containing oxytocin peptide formulation or composition is a liquid formulation comprising between about 0.5 IU/mL and about 8000 IU/mL (preferably between about 50 IU/mL and about 1000 IU/mL, more preferably between about 75 IU/mL and about 225 IU/mL, or about 150 IU/mL) of the oxytocin peptide and about 1% to about 25% (preferably about 8% to about 12%, or about 10%) (w/v) of magnesium chloride hexahydrate.

In some embodiments, the magnesium-containing oxytocin peptide formulation or composition comprises one or more magnesium salts selected from the group consisting of magnesium citrate, magnesium chloride, magnesium sulfate, magnesium acetate, magnesium lactate, magnesium stearate, magnesium oxide, magnesium carbonate, magnesium glycinate, magnesium maltate, magnesium taurate, magnesium gluconate, magnesium succinate, and magnesium pyrophosphate. In some embodiments, the magnesium-containing oxytocin peptide formulation or composition is a liquid formulation comprising a magnesium salt (e.g., magnesium citrate or magnesium chloride) in an amount to provide between about 1 mg/mL and about 30 mg/mL of magnesium. In some embodiments, the composition comprises a magnesium salt in an amount to provide between about 1 mg/mL and about 30 mg/mL of magnesium ion ($Mg^{2+}$). In some embodiments, the magnesium-containing oxytocin peptide formulation or composition is a liquid formulation comprising one or more magnesium salts (e.g., magnesium citrate and/or magnesium chloride) in an amount to provide between about 1 mg/mL and about 30 mg/mL of magnesium or magnesium ion ($Mg^{2+}$). In some embodiments, the composition comprises one or more magnesium salts in an amount to provide between about 11 mg/mL and about 15 mg/mL of magnesium or magnesium ion. In some embodiments, the magnesium-containing oxytocin peptide formulation or composition is a liquid formulation comprising between about 0.01 mg/mL and about 16 mg/mL (preferably between about 0.1 mg/mL and about 2 mg/mL, more preferably between about 0.15 mg/mL and about 1.5 mg/mL, or about 0.33 mg/mL) of the oxytocin peptide and a magnesium salt (e.g., magnesium citrate or magnesium chloride) in an amount to provide between about 1 mg/mL and about 30 mg/mL (or between about 3 mg/mL and about 30 mg/mL, between about 4 mg/mL and about 30 mg/mL, between about 5 mg/mL and about 30 mg/mL, between about 8 mg/mL and about 30 mg/mL, between about 10 mg/mL and about 30 mg/mL, preferably between about 11 mg/mL and about 15 mg/mL, or about 13 mg/mL, or about 12 mg/mL) of magnesium or $Mg^{2+}$. In some embodiments, the magnesium-containing oxytocin peptide formulation or composition is a liquid formulation comprising between about 5 IU/mL and about 8000 IU/mL (preferably between about 50 IU/mL and about 1000 IU/mL, more preferably between about 75 IU/mL and about 750 IU/mL, or about 150 IU/mL) of the oxytocin peptide and one or more magnesium salts (e.g., magnesium citrate and/or magnesium chloride) in an amount to provide between about 1 mg/mL and about 30 mg/mL (preferably between about 11 mg/mL and about 15 mg/mL, or about 13 mg/mL, or about 12 mg/mL) of magnesium or $Mg^{2+}$. In some embodiments, the magnesium-containing oxytocin peptide formulation or composition is a liquid formulation comprising between about 5 IU/mL and about 8000 IU/mL (preferably between about 50 IU/mL and about 1000 IU/mL, more preferably between about 75 IU/mL and about 750 IU/mL, or about 150 IU/mL) of the oxytocin peptide and one or more magnesium salts (e.g., magnesium citrate and/or magnesium chloride) in an amount to provide between about 50 mM and about 1200 mM (or between about 100 mM and about 1200 mM, between about 150 mM and about 1200 mM, between about 200 mM and about 1200 mM, between about 300 mM and about 1200 mM, between about 400 mM and about 1200 mM, preferably between about 400 mM and about 600 mM, or about 500 mM) of magnesium or $Mg^{2+}$.

The relative amount of the oxytocin peptide and the magnesium or magnesium ions in the magnesium-containing oxytocin peptide formulation or composition detailed herein may be defined by a weight ratio or a molar ratio. The weight ratio between the amount of the oxytocin peptide and the amount of magnesium or magnesium ions provided by the magnesium salt in the formulation or composition is referred to as the "OT/Mg (w) ratio". For example, in a magnesium-containing oxytocin peptide formulation or composition having an OT/Mg (w) ratio of about 1:40, for each 1 mg of the oxytocin peptide present in the formulation or composition, the magnesium salt present in the formulation or composition provides about 40 mg of magnesium or magnesium ions. The molar ratio between the amount of the oxytocin peptide and the amount of magnesium or magnesium ions provided by the magnesium salt in the formulation or composition is referred to as the "OT/Mg (m) ratio". For example, in a magnesium-containing oxytocin peptide formulation or composition having an OT/Mg (m) ratio of about 1:1600, for each 1 µmol of the oxytocin peptide present in the formulation or composition, the magnesium salt present in the formulation or composition provides about 1600 µmol of magnesium or magnesium ions.

In some embodiments, provided is a magnesium-containing oxytocin peptide formulation or composition comprising an oxytocin peptide and a magnesium salt, wherein the formulation or composition having an OT/Mg (w) ratio between about 1:1 and about 1:1000. In some embodiments, the formulation or composition has an OT/Mg (w) ratio between about 1:2 and about 1:200. In some preferred embodiments, the formulation or composition has an OT/Mg (w) ratio of about 1:30, about 1:35, about 1:40, about 1:45, or about 1:50. In some embodiments, the formulation or composition has an OT/Mg (w) ratio between about 1:2 and about 1:1000, between about 1:2 and about 1:800, between about 1:2 and about 1:500, between about 1:2 and about 1:250, between about 1:2 and about 1:150, between about 1:2 and about 1:100, between about 1:2 and about 1:80, between about 1:2 and about 1:60, between about 1:2 and about 1:50, between about 1:2 and about 1:40, between about 1:2 and about 1:30, between about 1:2 and about 1:20, between about 1:2 and about 1:10, between about 1:2 and about 1:5, between about 1:5 and about 1:1000, between about 1:5 and about 1:800, between about 1:5 and about 1:500, between about 1:5 and about 1:200, between about 1:5 and about 1:100, between about 1:5 and about 1:80, between about 1:5 and about 1:60, between about 1:5 and about 1:50, between about 1:5 and about 1:40, between about 1:5 and about 1:30, between about 1:5 and about 1:20, between about 1:5 and about 1:10, between about 1:10 and about 1:1000, between about 1:10 and about 1:800, between about 1:10 and about 1:500, between about 1:10 and about 1:200, between about 1:10 and about 1:100, between about 1:10 and about 1:80, between about 1:10 and about 1:60, between about 1:10 and about 1:50, between about 1:10 and about 1:40, between about 1:10 and about 1:30, between about 1:10 and about 1:20, between about 1:20 and about 1:1000, between about 1:20 and about 1:800, between about 1:20 and about 1:500, between about 1:20 and about 1:200, between about 1:20 and about 1:100, between about 1:20 and about 1:80, between about 1:20 and about 1:70, between about 1:20 and about 1:60, between about 1:20 and about 1:50, between about 1:20 and about 1:40, between about 1:20 and about 1:30, between about 1:30 and about 1:1000, between about 1:30 and about 1:800, between about 1:30 and about 1:500, between about 1:30 and about 1:200, between about 1:30 and about 1:100, between about 1:30 and about 1:80, between about 1:30 and about 1:70, between about 1:30 and about 1:60, between about 1:30 and about 1:50, between about 1:30 and about 1:40, between about 1:35 and about 1:45, between about 1:40 and about 1:1000, between about 1:40 and about 1:800, between about 1:40 and about 1:500, between about 1:40 and about 1:200, between about 1:40 and about 1:100, between about 1:40 and about 1:80, between about 1:40 and about 1:70, between about 1:40 and about 1:60, between about 1:40 and about 1:50, between about 1:50 and about 1:1000, between about 1:50 and about 1:800, between about 1:50 and about 1:500, between about 1:50 and about 1:200, between about 1:50 and about 1:100, between about 1:50 and about 1:90, between about 1:50 and about 1:80, between about 1:50 and about 1:70, between about 1:50 and about 1:60, between about 1:60 and about 1:1000, between about 1:60 and about 1:800, between about 1:60 and about 1:500, between about 1:60 and about 1:200, between about 1:60 and about 1:100, between about 1:60 and about 1:90, between about 1:60 and about 1:80, between about 1:60 and about 1:70, between about 1:80 and about 1:1000, between about 1:80 and about 1:800, between about 1:80 and about 1:500, between about 1:80 and about 1:200, between about 1:80 and about 1:100, between about 1:100 and about 1:1000, between about 1:100 and about 1:800, between about 1:100 and about 1:500, between about 1:100 and about 1:200, between about 1:200 and about 1:1000, between about 1:200 and about 1:800, between about 1:200 and about 1:500, or between about 1:500 and about 1:1000. In one embodiment, the oxytocin peptide is human oxytocin consisting of Cys-Tyr-Ile-Gln-Asn-Cys-Pro-Leu-Gly (SEQ. ID NO:1) and/or the magnesium salt is magnesium citrate.

In some embodiments, provided is a magnesium-containing oxytocin peptide formulation or composition comprising an oxytocin peptide and a magnesium salt, wherein the formulation or composition having an OT/Mg (m) ratio between about 1:40 and about 1:40,000. In some embodiments, the formulation or composition has an OT/Mg (m) ratio between about 1:80 and about 1:8000. In some preferred embodiments, the formulation or composition has an OT/Mg (m) ratio of about 1:1200, about 1:1400, about 1:1600, about 1:1800, or about 1:2000. In some embodiments, the formulation or composition has an OT/Mg (m) ratio between about 1:80 and about 1:40000, between about 1:80 and about 1:30000, between about 1:80 and about 1:20000, between about 1:80 and about 1:10000, between about 1:80 and about 1:7500, between about 1:80 and about 1:5000, between about 1:80 and about 1:3000, between about 1:80 and about 1:2000, between about 1:80 and about 1:1600, between about 1:80 and about 1:1200, between about 1:80 and about 1:800, between about 1:80 and about 1:400, between about 1:80 and about 1:200, between about 1:200 and about 1:40000, between about 1:200 and about 1:30000, between about 1:200 and about 1:20000, between about 1:200 and about 1:10000, between about 1:200 and about 1:5000, between about 1:200 and about 1:3000, between about 1:200 and about 1:2400, between about 1:200 and about 1:2000, between about 1:200 and about 1:1600, between about 1:200 and about 1:1200, between about 1:200 and about 1:800, between about 1:200 and about 1:400, between about 1:400 and about 1:40000, between about 1:400 and about 1:30000, between about 1:400 and about 1:20000, between about 1:400 and about 1:8000, between about 1:400 and about 1:4000, between about 1:400 and about 1:3000, between about 1:400 and about 1:2400, between about 1:400 and about 1:2000, between about 1:400 and about 1:1600, between about 1:400 and about 1:1200, between about 1:400 and about 1:800, between about 1:800 and about 1:40000, between about 1:800 and about 1:30000, between about 1:800 and about 1:20000, between about 1:800 and about 1:10000, between about 1:800 and about 1:5000, between about 1:800 and about 1:3000, between about 1:800 and about 1:2400, between about 1:800 and about 1:2000, between about 1:800 and about 1:1600, between about 1:800 and about 1:1200, between about 1:1200 and about 1:40000, between about 1:1200 and about 1:30000, between about 1:1200 and about 1:20000, between about 1:1200 and about 1:10000, between about 1:1200 and about 1:5000, between about 1:1200 and about 1:4000, between about 1:1200 and about 1:3000, between about 1:1200 and about 1:2400, between about 1:1200 and about 1:2000, between about 1:1200 and about 1:1600, between about 1:1400 and about 1:1800, between about 1:1600 and about 1:40000, between about 1:1600 and about 1:30000, between about 1:1600 and about 1:20000, between about 1:1600 and about 1:10000, between about 1:1600 and about 1:5000, between about 1:1600 and about 1:3000, between about 1:1600 and about 1:2400, between about 1:1600 and about 1:2000, between about 1:2000 and about 1:40000, between about 1:2000 and about 1:30000, between about 1:2000 and about 1:20000, between about 1:2000 and about 1:10000, between about 1:2000 and about 1:5000, between about 1:2000 and about 1:4000, between about 1:2000 and about 1:3000, between about 1:2000 and about 1:2400, between about 1:2400 and about 1:40000, between about 1:2400 and about 1:30000, between about 1:2400 and about 1:20000, between about 1:2400 and about 1:10000, between about 1:2400 and about 1:5000, between about 1:2400 and about 1:4000, between about 1:2400 and about 1:3000, between about 1:3000 and about 1:40000, between about 1:3000 and about 1:30000, between about 1:3000 and about 1:20000, between about 1:3000 and about 1:10000, between about 1:3000 and about 1:4000, between about 1:4000 and about 1:40000, between about 1:4000 and about 1:30000, between about 1:4000 and about 1:20000, between about 1:4000 and about 1:10000, between about 1:8000 and about 1:40000, between about 1:8000 and about 1:30000, between about 1:8000 and about 1:20000, or between about 1:10000 and about 1:40000. In one embodiment, the oxytocin peptide is human oxytocin consisting of Cys-Tyr-Ile-Gln-Asn-Cys-Pro-Leu-Gly (SEQ. ID NO:1) and/or the magnesium salt is magnesium citrate.

In some embodiments, the magnesium-containing oxytocin peptide formulation or composition comprising an oxytocin peptide and a magnesium salt further comprises one or more pharmaceutically acceptable carriers (thus constituting a pharmaceutical composition) and optionally other ingredients, such as excipients, vehicles, emulsifiers, stabilizers, preservatives, buffers, and/or other additives that may enhance stability, delivery, absorption, half-life, efficacy, pharmacokinetics, and/or pharmacodynamics, reduce adverse side effects, or provide other advantages for pharmaceutical use. Exemplary excipients include solubilizers, surfactants and chelators. For example, formulations may include, methyl-β-cyclodextrin (Me-β-CD), edetate disodium, arginine, sorbitol, NaCl, methylparaben sodium (MP), propylparaben sodium (PP), chlorobutanol (CB), benzyl alcohol, zinc chloride, ethyl alcohol, didecanoyl L-α-phosphatidylcholine (DDPC), polysorbate, lactose, citrate, tartrate, acetate, and/or phosphate.

Liquid carriers include, but are not limited to, water, saline, aqueous dextrose, and glycols particularly (when isotonic) for solutions. The carrier can also be selected from various oils, including those of petroleum, animal, vegetable or synthetic origin (e.g. peanut oil, olive oil, soybean oil, mineral oil, sesame oil, and the like). Suitable pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, anti-oxidants, chelating agents, wetting agents, emulsifying agents, dispersing agents, jelling agents, salts for adjusting osmotic pressure, buffers, and the like. A liquid carrier may be hypotonic or isotonic with body fluids and may have a pH within the range of 3.5-8.5. The use of additives in the preparation of peptide and/or protein-based compositions, particularly pharmaceutical compositions, is well-known in the art. In some embodiments, the composition has a pH of about 2 to about 7. In some embodiments, the composition has a pH of about 4 to about 7. In a preferred embodiment, the pH of the formulation/composition is about 4.5.

In some embodiments, the magnesium-containing oxytocin peptide formulation or composition may further comprise one or more mucosal delivery-enhancing agents selected from (A)-(K): (A) solubilization agents; (B) charge modifying agents; (C) pH control agents; (D) degradative enzyme inhibitors; (E) mucolytic or mucus clearing agents; (F) ciliostatic agents; (G) membrane penetration-enhancing agents; (H) modulatory agents of epithelial junction physiology, such as nitric oxide (NO) stimulators, chitosan, and chitosan derivatives; (I) vasodilator agents; (J) selective transport-enhancing agents; and (K) stabilizing delivery vehicles, carriers, supports or complex-forming species with which the oxytocin peptide is effectively combined, associated, contained, encapsulated or bound to stabilize the active agent for enhanced mucosal delivery. Membrane penetration-enhancing agents in Group (G) may be (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule, (viii) a small hydrophobic penetration enhancer; (ix) sodium or a salicylic acid derivative; (x) a glycerol ester of acetoacetic acid, (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)-(xviii). In various embodiments of the invention, an oxytocin peptide may be combined with one, two, three, four or more of the mucosal delivery-enhancing agents recited in (A)-(K). These mucosal delivery-enhancing agents may be admixed, alone or together, with the oxytocin peptide, or otherwise combined therewith in a pharmaceutically acceptable formulation or delivery vehicle. The magnesium-containing oxytocin peptide formulation or composition described herein may provide increased bioavailability of the oxytocin peptide following delivery thereof to a mucosal surface (e.g., in the nasal cavities) of a mammalian subject.

The lists of carriers and additives discussed herein are by no means complete and a worker skilled in the art can choose carriers and excipients from the GRAS (generally regarded as safe) list of chemicals allowed in pharmaceutical preparations and those that are currently allowed by the U.S. Food and Drug Administration in topical and parenteral formulations, and those that become allowed in the future. (See also Wang et al., (1980) *J. Parent. Drug Assn.*, 34:452-462; Wang et al., (1988) *J. Parent. Sci. and Tech.*, 42:S4-S26.)

In some embodiments, the magnesium-containing oxytocin peptide formulation or composition, comprising an oxytocin peptide and a magnesium salt, wherein the oxytocin peptide and the magnesium salt are in an amount that produces a synergistic analgesia when used in the treatment of pain, further comprises one or more solvent or excipient selected from the group consisting of chlorobutanol, benzalkonium, methyl 4-hydroxybenzoate, propyl 4-hydroxybenzoate, acetic acid, citric acid, glycerol, sodium chloride, sodium monohydrogen phosphate, sorbitol and water. In some embodiments, the magnesium-containing oxytocin peptide formulation or composition further comprises chlorobutanol, acetic acid and water.

In some embodiments, the magnesium-containing oxytocin peptide formulation or composition, comprising an oxytocin peptide and a magnesium salt, further comprises a chitosan-containing excipient (e.g., ChiSys®, http://www.archimedespharma.com/productArchiDevChiSys.html).

In some embodiments, the magnesium-containing oxytocin peptide formulation or composition further comprises about 1% of the chitosan-containing excipient. In some embodiments, a chitosan glutamate salt may be preferred for nasal delivery for its superior absorption enhancing ability. In some embodiments, chitosan co-polymer nanoparticles may be used, such as nanoparticles containing chitosan glutamate and a negatively charged polymer (e.g., tripolyphosphate pentasodium). Thiolated chitosans (e.g. chitosan covalently modified with 2-iminothiolane), which have been used in microparticles containing insulin and reduced glutathione, may also be useful as an excipient in the magnesium-containing oxytocin peptide formulation or composition described herein.

In some embodiments, the magnesium-containing oxytocin peptide formulation or composition, comprising an oxytocin peptide and a magnesium salt, further comprises one or more gelling agents, such that the oxytocin peptide formulation forms a gel in the nasal cavity, thus enhancing nasal absorption of the oxytocin peptide. Gelling systems useful in the formulations and methods described herein may include any known gelling system, such as a chemically reactive pectin-based gelling system (e.g., PecSys™, Archimedes Pharma) and a thermoreactive polymer gelling system (e.g., Pluronic® F127, BASF). PecSys™ is a low viscosity aqueous pectin based solution, delivered as a fine mist in which each droplet gels on contact with calcium ions in the nasal mucosa. Other low methoxy pectin could also be employed, e.g., at about 1% concentration. Pluronic® F127 contains ethylene oxide/propylene oxide block copolymers. The gelling temperatures vary depending on the ratios of components and the amount of co-polymer employed in the final formulation. Gelling in the human nasal cavity has been demonstrated for Pluronic® F127 at approximately 18-20% wt/vol, for examples, as used in a vitamin B12 gel supplement (EnerB, Nature's Bounty, NY) and in a gelling sumatriptan, which contains 18% wt/vol Pluronic® F127 and 0.3% wt/vol Carbopol (anionic bioadhesive polymer C934P). The monomer ratios and concentrations may be adjusted for the intended oxytocin formulations to ensure gelling at 25-37° C., around the typical temperature of 34° C. in nasal cavity. If the gelation temperature is lower than 25° C., the formulation could gel at room temperature; if the gelation temperature is above 37° C., the formulation would not fully gel on contact with the nasal mucosa. In some embodiments, the magnesium-containing oxytocin peptide formulation or composition may further comprise a mucoadhesive agent such as Carbopol. Addition of a mucoadhesive, e.g., addition of up to 0.5% Carbopol, may further lower the gelation temperature.

In some embodiments, the magnesium-containing oxytocin peptide formulation or composition, comprising an oxytocin peptide and a magnesium salt, further comprises a surface active agent, such as a nonionic surfactant (e.g., polysorbate-80), and one or more buffers, stabilizers, or tonicifiers. In some embodiments, the magnesium-containing oxytocin peptide formulation or composition further comprises a propellant. The pH of the nasal spray solution is optionally between about pH 3.0 and 8.5, but when desired the pH is adjusted to optimize delivery of a charged macromolecular species (e.g., a therapeutic protein or peptide) in a substantially unionized state. The pharmaceutical solvents employed can also be a slightly acidic aqueous buffer (pH 3-6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzalkonium chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid (EDTA), and the like. Suitable gases include, but are not limited to, nitrogen, helium, chlorofluorocarbons (CFCs), hydrofluorocarbons (HFCs), carbon dioxide, air, and the like. Suitable stabilizers and tonicifying agents include sugars and other polyols, amino acids, and organic and inorganic salts. In some embodiments, the magnesium-containing oxytocin peptide formulation or composition further comprises a citrate salt, a succinate salt or a pyrophosphate salt.

To further enhance the mucosal delivery of the oxytocin peptide, an enzyme inhibitor, particularly proteases inhibitors, can be included further in the formulation. Protease inhibitors may include, but are not limited to, antipain, arphamenine A and B, benzamidine HCl, AEBSF, CA-074, calpain inhibitor I and II, calpeptin, pepstatin A, actinonin, amastatin, bestatin, boroleucine, captopril, chloroacetyl-HOLeu-Ala-Gly-NH$_2$, DAPT, diprotin A and B, ebelactone A and B, foroxymithine, leupeptin, phosphoramidon, aprotinin, puromycin, BBI, soybean trypsin inhibitor, phenylmethylsulfonyl fluoride, E-64, chymostatin, 1,10-phenanthroline, EDTA and EGTA. Other enzyme inhibitors such as bacitracin may also be included in the formulation.

To enhance delivery into or across a mucosal surface and/or absorption of the oxytocin peptide and the magnesium salt, an absorption-enhancing agent can be included in the formulation. These enhancing agents may enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery) of the composition. Enhancement of mucosal delivery can thus occur by any of a variety of mechanisms, for example by increasing the diffusion, transport, persistence or stability of the oxytocin peptide, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

Mucosal absorption enhancing compounds may include, but are not limited to, surfactants, bile salts, dihydrofusidates, bioadhesive/mucoadhesive agents, phospholipid additives, mixed micelles, liposomes, or carriers, alcohols, enamines, cationic polymers, NO donor compounds, long-chain amphipathic molecules, small hydrophobic penetration enhancers; sodium or a salicylic acid derivatives, glycerol esters of acetoacetic acid, cyclodextrin or beta-cyclodextrin derivatives, medium-chain fatty acids, chelating agents, amino acids or salts thereof, N-acetylamino acids or salts thereof, mucolytic agents, enzymes specifically targeted to a selected membrane component, inhibitors of fatty acid synthesis and inhibitors of cholesterol synthesis.

All peptides described and/or contemplated herein can be prepared by chemical synthesis using either automated or manual solid phase synthetic technologies, generally known in the art. The peptides can also be prepared using molecular recombinant techniques known in the art.

Delivery Systems

The magnesium-containing oxytocin peptide formulation or composition may be adapted for craniofacial mucosal administration (e.g., nasal, buccal, sublingual or ocular administration). In some embodiments, the composition may further comprise a device for mucosal delivery. In some embodiments, the composition is adapted for buccal and/or sublingual mucosal delivery, which may further comprise a device for buccal and/or sublingual mucosal administration, such as unit dose containers, pump sprays, droppers, squeeze bottles, airless and preservative-free sprays, nebulizers, dose inhalers and pressurized dose inhalers. In some embodiments, the composition is adapted for ocular delivery, which may further comprise a device for conjunctival administration, such as a dropper or a squeeze bottle. In some embodiments, the composition is adapted for intranasal administration, which may further comprise a device for intranasal administration, such as a dropper, pump spray, squeeze bottle, airless and preservative-free sprays, or a nasal pump apparatus, e.g., a nasal pump apparatus comprising a reservoir bottle attached to an aerosolizer.

Intranasal drug delivery has been a topic of research and development for many years, although it has been only within the past decade that carrier systems have been devised which make delivery of substances effective. (Sayani and Chien, *Critical Reviews in Therapeutic Drug Carrier Systems* 1996, 13:85-184.) Intranasal delivery has a number of advantageous features including comparatively high bioavailability, rapid kinetics of absorption and avoidance of a first-pass effect in the liver. In some aspects, intranasal administration can allow for delivery of an oxytocin peptide to the nasal cavity and in other aspects, intranasal administration can allow for targeted delivery to the cranial nerves of the nose and/or the brain. Without wishing to be bound by any particular theories, intranasal administration of an oxytocin peptide can target either the olfactory nerve systems or the trigeminal nerve systems or both. The oxytocin peptide may be delivered intranasally in any applicable forms, including but is not limited to a liquid formulation, a solid formulation (e.g., a dry powder formulation), a gel formulation or an emulsion formulation.

In embodiments where the combination of oxytocin and a magnesium salt are administered intranasally, the composition can be prepared as a liquid aerosol formulation combined with a dispersing agent and/or a physiologically acceptable diluent. Alternatively, dry powder aerosol formulations are contemplated, and may contain a finely divided solid form of the subject compound and a dispersing agent allowing for the ready dispersal of the dry powder particles. With either liquid or dry powder aerosol formulations, the formulation is aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter for nasal (in a range of from about 10 microns) or pulmonary (in a range of from about 2-5 microns) distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

In some embodiments, provided is a magnesium-containing oxytocin peptide formulation or composition, comprising an oxytocin peptide and a magnesium salt, wherein the oxytocin peptide and the magnesium salt are in an amount that produces a synergistic analgesia when used in the treatment of pain, further comprises a device for intranasal delivery. The device may be any device suitable for intranasal administration of the magnesium-containing oxytocin peptide formulation. In some embodiments, the device is suitable for delivery of the oxytocin peptide and the magnesium salt to specific region within the nasal cavity. In some embodiments, the device is suitable for delivery of the oxytocin peptide and the magnesium salt to the inferior two-thirds of the nasal cavity. In some embodiments, the device is suitable for delivery of the oxytocin peptide and the magnesium salt to the upper third of the nasal cavity. In some embodiments, the device is suitable for delivery of the oxytocin peptide to the entire nasal passage.

In some embodiments, the device for intranasal delivery is a nasal pump apparatus. In some embodiments, the nasal pump apparatus comprises a reservoir bottle attached to a pump actuator. In some embodiments, the pump actuator is metered to deliver a specified volume (e.g. about 50 to about 150 μL, preferably about 50 μL or about 100 μL) in a specified distribution of droplet sizes. In some embodiments, the nasal pump apparatus comprises a reservoir bottle attached to an aerosolizer, e.g. an Equadel pump marketed by Aptar Pharma. In some embodiments, the device for nasal administration functions irrespective of the pressure applied to the pump once a threshold value is reached. For administration in large mammals, the nasal pump apparatus may comprise a reservoir bottle attached to a pump actuator that is metered to deliver larger volumes (e.g., about 100 μL to about 600 μL, or higher).

In some embodiments, the device for intranasal delivery is designed for delivery of multiple doses of the drug formulations. For example, a nasal pump apparatus may comprise a reservoir bottle attached to a pump actuator where the reservoir bottle holds multiple dose of the liquid formulation and the pump actuator is metered to deliver a specified volume that is a fraction of the liquid formulation held in the reservoir bottle. In some embodiments, the pump actuator is metered to deliver about 50 μL of the liquid formulation per spray. The nasal pump apparatus may comprise a filter for preventing back flow in order to reduce contaminant (e.g., bacterial) ingress into the reservoir bottle. In some embodiments, the nasal pump apparatus comprises a metal-free path for delivery of the liquid formulation (e.g., a plastic path). In some embodiments, the pump apparatus uses plastic material that is stable to gamma radiation (used for sterilizing the nasal apparatus). In some embodiments, the device for intranasal delivery is equipped with a multi-dose pump comprising a microbial filter and an auto-blocking mechanism in the pump actuator, for example, a spray device described in U.S. Pat. No. 5,988,449.

In some embodiments, the device for intranasal delivery is a breath-actuated nasal delivery device, such as the devices described in U.S. Pat. Nos. 7,784,460 and 7,854,227. Such devices may improve delivery to a target site deep into the nasal cavity. In some embodiments, a standard metered dose spray device is incorporated into a housing that allows the patient to blow into a mouthpiece to actuate the device. In some embodiments, the device is comprised of a conical sealing nosepiece and a mouthpiece that incorporate a traditional mechanical spray pump (e.g. an Equadel pump marketed by Aptar Pharma), a chargeable spring and a breath actuation mechanism. The system can be used for single or multi-dose delivery. One example of such a liquid delivery device is the OptiMist™ device marketed by Opti-Nose. When in use, the nasal piece of the device is inserted into the nostril and the mouth piece is blown into. This closes the soft palate, transfers pressure to the nostril, opens passages providing airflow behind the nasal septum and allows air to exit the other nostril (bidirectional flow). Since the device is breath actuated, small particles cannot enter the lungs. Modifications to flow rate and particle size allows for targeting of specific nasal regions.

In some embodiments, the device for intranasal delivery is a unit-dose metering spray device suited for single administration of the magnesium-containing oxytocin peptide formulation or composition. In some embodiments, the device for intranasal delivery is a multi-dose metering spray pump apparatus suited for repeated administrations of an oxytocin peptide.

Drop size, plume volume and flow rate can be modified to target specific nasal regions. The liquid spray may provide droplet size between 5 and 50 microns in order to target olfactory and/or respiratory epithelium. Larger droplets primarily travel down the nasopharynx and are swallowed, while smaller droplets are targeted to the pulmonary tissue. The Mass Median Equivalent Aerodynamic Diameter (MMAD) is used to specify the drop size. The pH of the nasal spray is optimized to deliver charged peptide in mostly an unionized state. The nose will generally tolerate solutions having a pH of about 3-8. The nasal mucosa can generally absorb volumes of approximately 100 μL before saturation occurs and liquid begins to drip out of the nose. Therefore, plume volume may be up to (and including) 100 μL. For use in large mammals, plume volume may be up to (and including) 150 μL or higher (e.g., 600 μL or higher). For infant and pediatric use, or for veterinary use in smaller animals (e.g., rodents, cats), smaller plume volumes (5-50 μL) could be used.

In some embodiments, the device for intranasal delivery is an ergonomically designed to facilitate patient compliance, such as a pump apparatus with a side-actuation triggering mechanism. In some embodiments, the device for intranasal delivery comprises a metering spray pump working as a closed system, which does not allow air to enter into the pump apparatus thus preventing contamination from airborne germs. In some embodiment, the device for intranasal delivery comprises a metering spray pump working with a filter. The venting air is sucked through a filter assembled inside the pump, keeping airborne germs out of the pump apparatus. In some embodiments, the intranasal delivery device comprising a nasal pump apparatus may further comprise micro-electronic devices that may facilitate data transmission and treatment monitoring.

In some embodiments, the magnesium-containing oxytocin peptide formulation or composition comprises an oxytocin peptide and a magnesium salt wherein the oxytocin peptide and the magnesium salt are contained in any one of the devices for intranasal delivery described herein, and wherein the concentrations of the oxytocin peptide and the magnesium salt are within any of the concentration ranges described herein, as if each and every combination of device and concentration is described individually.

Methods

In one aspect, the invention provides a method for treating pain comprising administering to a subject in need thereof an effective dose of an oxytocin peptide and a magnesium salt, wherein co-administration of the oxytocin peptide and the magnesium salt produces a synergistic analgesia. In some embodiments, the oxytocin peptide and the magnesium salt are administered at a dose that produces an overall analgesia or analgesic effect that is greater than the sum of the analgesia or analgesic effects of equivalent doses of the oxytocin peptide and the magnesium salt administered individually. In some embodiments, co-administration of the oxytocin peptide and the magnesium salt results in a reduction of the intensity of the pain or sensitivity to painful stimulation (allodynia and/or hyperalgesia) experienced by the subject that is greater than the sum of the reduction of the pain intensity or sensitivity to painful stimulation (allodynia and/or hyperalgesia) by equivalent doses of the oxytocin peptide and the magnesium salt administered individually. In some embodiments, co-administration of the oxytocin peptide and the magnesium salt results in a reduction of the frequency of the pain experienced by the subject that is greater than the sum of the reduction of the pain frequency by equivalent doses of the oxytocin peptide and the magnesium salt administered individually. In some embodiments, co-administration of the oxytocin peptide and the magnesium salt results in a faster onset of analgesia or analgesic effect than any of the equivalent doses of the analgesic agents administered individually. In some embodiments, co-administration of the oxytocin peptide and the magnesium salt results in a longer lasting analgesia or analgesic effect than any of the equivalent doses of the analgesic agents administered individually.

The oxytocin peptide and the magnesium salt may be administered concurrently or sequentially. In some embodiments, the oxytocin peptide is administered concurrently with the magnesium salt in the same unit dose. In some embodiments, the oxytocin peptide is administered concurrently with the magnesium salt but in separate unit doses or formulations. In some embodiments, oxytocin peptide and the magnesium salt are administered sequentially. In some embodiments, the magnesium salt is administered to the subject in a first administration and then the oxytocin peptide is administered to the subject in a second administration. In some of these embodiments, the oxytocin peptide is administered between about 10 minutes and about 2 hours after administration of the magnesium salt. In some of these embodiments, the oxytocin peptide is administered between about 10 minutes and about 2 hours, between about 10 minutes and about 1 hour, between about 10 minutes and about 30 minutes, between about 20 minutes and about 2 hours, between about 20 minutes and about 1 hour, between about 30 minutes and about 2 hours or between about 30 minutes and about 1 hour after administration of the magnesium salt. In some of these embodiments, the oxytocin peptide is administered about 10 minutes, about 15 minutes, about 20 minutes, about 30 minutes, about 45 minutes, about 60 minutes, about 90 minutes or about 120 minutes after administration of the magnesium salt. In some of these embodiments, the oxytocin peptide is administered about 10 minutes, about 15 minutes, about 20 minutes, about 30 minutes after administration of the magnesium salt. In one embodiment, the oxytocin peptide is administered to the subject first and then the magnesium salt is administered to the subject. In some embodiments, the subject is a human.

The oxytocin peptide and the magnesium salt may be administered via the same route or different routes to a subject in need thereof. In some embodiments, the oxytocin peptide is administered via craniofacial mucosal administration (e.g., nasal, buccal, sublingual or ocular administration). In one embodiment, the oxytocin peptide and the magnesium salt are both administered intranasally in the same formulation. In one embodiment, the oxytocin peptide is administered via craniofacial mucosa and the magnesium salt is administered systemically, e.g., intravenously, intramuscularly, orally, subcutaneously, or intrathecally.

In some embodiments, the oxytocin peptide is administered via intranasal administration. In some embodiments, the oxytocin peptide and the magnesium salt are administered via intranasal administration. The oxytocin peptide and/or the magnesium salt can be administered to the mucosa tissue within the nasal cavity using a suitable device for intranasal delivery such as a nasal delivery device described herein. Suitable regions within the nasal cavity include, but are not limited to, the inferior two-thirds of the nasal cavity, or the upper third, or the entire nasal passage. In some embodiments, the oxytocin peptide and/or the magnesium salt are administered to the upper third of the nasal cavity. In some embodiments, the oxytocin peptide and/or the magnesium salt are administered to the lower two thirds of the nasal cavity. In some embodiments, the oxytocin peptide and/or the magnesium salt are administered specifically to reach both the lower two thirds and the upper third of the nasal cavity. In some embodiments, a method is provided for treating pain comprising intranasally administering to a subject in need thereof an effective dose of an oxytocin peptide and a magnesium salt, wherein co-administration of the oxytocin peptide and the magnesium salt produces a synergistic analgesia.

In some embodiments, the oxytocin peptide is human oxytocin consisting of Cys-Tyr-Ile-Gln-Asn-Cys-Pro-Leu-Gly (SEQ. ID NO:1). In some embodiments, the effective dose of the oxytocin peptide is about 0.5 µg to about 2000 µg. In some embodiments, the effective dose of the oxytocin peptide is about 0.5 µg to about 1000 µg, about 1 µg to about 1000 µg or about 1 µg to about 2000 µg. In some embodiments, the effective dose of the oxytocin peptide is about 4 µg to about 1000 µg, about 8 µg to about 1000 µg, about 8 µg to about 800 µg, about 8 µg to about 500 µg, about 8 µg to about 400 µg, about 8 µg to about 300 µg, about 8 µg to about 200 µg, about 8 µg to about 100 µg, about 8 µg to about 80 µg, about 8 µg to about 50 µg, about 10 µg to about 1000 µg, about 10 µg to about 500 µg, about 10 µg to about 200 µg, about 10 µg to about 100 µg, about 16 µg to about 1000 µg, about 16 µg to about 800 µg, about 16 µg to about 500 µg, about 16 µg to about 400 µg, about 16 µg to about 200 µg, about 16 µg to about 160 µg, about 16 µg to about 120 µg, about 16 µg to about 80 µg, about 20 µg to about 1000 µg, about 20 µg to about 800 µg, about 20 µg to about 500 µg, about 20 µg to about 200 µg, about 20 µg to about 100 µg, about 30 µg to about 1000 µg, about 30 µg to about 500

µg, about 30 µg to about 300 µg, about 30 µg to about 120 µg, about 30 µg to about 90 µg, about 50 µg to about 1000 µg, about 50 µg to about 500 µg, about 50 µg to about 250 µg, about 50 µg to about 100 µg, or about 50 µg to about 80 µg. In some embodiments, the effective dose of the oxytocin peptide is about 8 µg, about 16 µg, about 32 µg, about 48 µg, about 64 µg, about 80 µg, about 96 µg, about 128 µg, about 256 µg, about 10 µg, about 20 µg, about 30 µg, about 40 µg, about 50 µg, about 60 µg, about 70 µg, about 80 µg, about 90 µg, about 100 µg, about 120 µg, about 150 µg, about 200 µg, about 400 µg, about 600 µg, about 800 µg or about 100 µg. In a preferred embodiment, the effective dose of the oxytocin peptide is about 8 µg to about 120 µg, about 15 µg to about 120 µg, about 30 µg to about 120 µg, or about 66 µg.

In some embodiments, the effective dose of the oxytocin peptide is about 0.25 IU to about 1000 IU. In some embodiments, the effective dose of the oxytocin peptide is about 0.25 IU to about 500 IU, about 0.5 IU to about 500 IU or about 0.5 IU to about 1000 IU. In some embodiments, the effective dose of the oxytocin peptide is about 2 IU to about 500 IU, about 4 IU to about 500 IU, about 4 IU to about 400 IU, about 4 IU to about 250 IU, about 4 IU to about 200 IU, about 4 IU to about 150 IU, about 4 IU to about 100 IU, about 4 IU to about 50 IU, about 4 IU to about 40 IU, about 4 IU to about 25 IU, about 5 IU to about 500 IU, about 5 IU to about 250 IU, about 5 IU to about 100 IU, about 5 IU to about 50 IU, about 8 IU to about 500 IU, about 8 IU to about 400 IU, about 8 IU to about 250 IU, about 8 IU to about 200 IU, about 8 IU to about 100 IU, about 8 IU to about 80 IU, about 8 IU to about 60 IU, about 8 IU to about 40 IU, about 10 IU to about 500 IU, about 10 IU to about 400 IU, about 10 IU to about 250 IU, about 10 IU to about 100 IU, about 10 IU to about 50 IU, about 15 IU to about 500 IU, about 15 IU to about 250 IU, about 15 IU to about 150 IU, about 15 IU to about 60 IU, about 15 IU to about 45 IU, about 25 IU to about 500 IU, about 25 IU to about 250 IU, about 25 IU to about 125 IU, about 25 IU to about 50 IU, or about 25 IU to about 40 IU. In some embodiments, the effective dose of the oxytocin peptide is about 4 IU, about 8 IU, about 16 IU, about 24 IU, about 32 IU, about 40 IU, about 48 IU, about 64 IU, about 128 IU, about 5 IU, about 10 IU, about 15 IU, about 20 IU, about 25 IU, about 30 IU, about 35 IU, about 40 IU, about 45 IU, about 50 IU, about 60 IU, about 75 IU, about 100 IU, about 200 IU, about 300 IU, about 400 IU or about 50 IU. In a preferred embodiment, the effective dose of the oxytocin peptide is about 4 IU to about 60 IU, about 7.5 IU to about 60 IU, about 15 IU to about 60 IU, or about 30 IU.

The dose or amount of oxytocin in the combination is, in one embodiment, effective to provide a clinically measurable improvement in a symptom of the pain disorder. As will be illustrated in the examples below, the combination of oxytocin and the magnesium salt provides a synergistic effect to improve the pain disorder. In some embodiments, oxytocin is administered at a sub-therapeutically effective dose relative to a dose of oxytocin administered as a single agent. The dose of oxytocin as a single agent depends, in part, on the route of administration. Accordingly, the dose of oxytocin in the combination therapy described herein will also depend, in part, on the route of administration.

The optimal dosage of the magnesium salt may depend on the specific pain-type, the type of synergistic effect desired, and other factors such as the route of administration. The optimal dose may be measured in the total amount of the magnesium salt administered, the amount of magnesium in the magnesium salt administered, the amount magnesium ions ($Mg^{2+}$) provided by the magnesium salt administered, or the concentration of the magnesium ions in the formulation administered. In some embodiments, the effective dose of the magnesium salt administered provides about 50 µg to about 68 mg of magnesium. In some embodiments, the effective dose of the magnesium salt administered provides about 50 µg to about 34 mg, or about 1 mg to about 3 mg of magnesium. In some embodiments, the effective dose of the magnesium salt administered provides about 50 µg to about 68 mg of magnesium ions ($Mg^{2+}$). In some embodiments, the effective dose of the magnesium salt administered provides about 50 µg to about 34 mg, or about 1 mg to about 3 mg of magnesium ions ($Mg^{2+}$). In some embodiments, the effective dose of the magnesium salt administered provides about 1.3 mg, or about 2.6 mg of magnesium or $Mg^{2+}$. In some embodiments, the effective dose of the magnesium salt administered provides about 1.2 mg, or about 2.4 mg of magnesium or $Mg^{2+}$. In some embodiments, the effective dose of the magnesium salt administered provides about 50 µg to about 17 mg, about 50 µg to about 8 mg, about 50 µg to about 4 mg, about 50 µg to about 2 mg, about 50 µg to about 1 mg, about 50 µg to about 500 µg, about 100 µg to about 68 mg, about 100 µg to about 34 mg, about 100 µg to about 17 mg, about 100 µg to about 8 mg, about 100 µg to about 4 mg, about 100 µg to about 2 mg, about 100 µg to about 1 mg, about 100 µg to about 500 µg, about 200 µg to about 68 mg, about 200 µg to about 34 mg, about 200 µg to about 17 mg, about 200 µg to about 8 mg, about 200 µg to about 4 mg, about 200 µg to about 2 mg, about 200 µg to about 1 mg, about 200 µg to about 500 µg, about 500 µg to about 68 mg, about 500 µg to about 34 mg, about 500 µg to about 17 mg, about 500 µg to about 8 mg, about 500 µg to about 5 mg, about 500 µg to about 4 mg, about 500 µg to about 3 mg, about 500 µg to about 2 mg, about 500 µg to about 1 mg, about 1 mg to about 68 mg, about 1 mg to about 34 mg, about 1 mg to about 17 mg, about 1 mg to about 8 mg, about 1 mg to about 6 mg, about 1 mg to about 5 mg, about 1 mg to about 4 mg, about 1 mg to about 3 mg, about 1 mg to about 2 mg, about 1.5 mg to about 8 mg, about 1.5 mg to about 6 mg, about 1.5 mg to about 5 mg, about 1.5 mg to about 4 mg, about 1.5 mg to about 3 mg, about 1.5 mg to about 2 mg, about 1.3 mg to about 2.6 mg, or about 1.2 mg to about 2.4 mg of magnesium or magnesium ions ($Mg^{2\pm}$). In some embodiments, the magnesium salt is magnesium citrate and/or magnesium chloride administered in an amount to provide about 50 µg to about 68 mg, about 50 µg to about 34 mg, or about 1 mg to about 3 mg of magnesium or $Mg^{2+}$. In some embodiments, the magnesium salt comprises magnesium citrate and/or magnesium chloride administered in an amount to provide about 50 µg to about 68 mg, about 50 µg to about 34 mg, or about 1 mg to about 3 mg of magnesium or $Mg^{2+}$.

In some embodiments, the magnesium salt administered comprises magnesium chloride and the effective dose of the magnesium salt is about 0.48 mg to about 600 mg of magnesium chloride hexahydrate ($MgCl_2.6H_2O$, MW 203.3). In some embodiments, the effective dose of magnesium chloride hexahydrate is about 0.48 mg to about 300 mg, about 0.5 mg to about 150 mg, about 0.5 mg to about 75 mg, about 5 mg to about 150 mg, about 5 mg to about 75 mg, about 5 mg to about 50 mg, about 10 mg to about 600 mg, about 10 mg to about 300 mg, about 10 mg to about 150 mg, about 10 mg to about 75 mg, about 10 mg to about 50 mg, about 10 mg to about 30 mg, or about 12 mg to about 24 mg. In some preferred embodiments, the effective dose of magnesium chloride hexahydrate is about 6 mg, about 12 mg, about 18 mg, about 24 mg or about 30 mg. In some embodiments, the effective dose of magnesium citrate is about 0.48 mg to about 12 mg, about 0.5 mg to about 10 mg, about 0.5 mg to about 8 mg, about 0.5 mg to about 5 mg, about 0.5 mg to about 2.5 mg, about 0.5 mg to about 1 mg, about 1 mg to about 10 mg, about 1 mg to about 8 mg, about 1 mg to about 5 mg, about 1 mg to about 2 mg, about 2 mg to about 10 mg, about 2 mg to about 8 mg, about 2 mg to about 6 mg, about 2 mg to about 4 mg, about 3 mg to about 10 mg, about 4 mg to about 10 mg, about 4 mg to about 8 mg, about 4 mg to about 6 mg, about 5 mg to about 10 mg, about 5 mg to about 8 mg, about 5 mg to about 7 mg, about 5 mg to about 6 mg, about 6 mg to about 10 mg, about 6 mg to about 8 mg, or about 6 mg to about 7 mg.

In some embodiments, the magnesium salt administered is magnesium citrate and the effective dose of the magnesium salt is about 0.48 mg to about 600 mg of magnesium citrate. In some embodiments, the effective dose of magnesium citrate (e.g., anhydrous magnesium citrate dibasic, MW. 214.4) is about 0.48 mg to about 300 mg, about 0.5 mg to about 150 mg, about 0.5 mg to about 75 mg, about 5 mg to about 150 mg, about 5 mg to about 75 mg, about 5 mg to about 50 mg, about 10 mg to about 600 mg, about 10 mg to about 300 mg, about 10 mg to about 150 mg, about 10 mg to about 75 mg, about 10 mg to about 50 mg, about 10 mg to about 30 mg, or about 12 mg to about 24 mg. In some preferred embodiments, the effective dose of magnesium citrate (e.g., anhydrous magnesium citrate dibasic, MW. 214.4) is about 6 mg, about 12 mg, about 18 mg, about 24 mg or about 30 mg. In some embodiments, the effective dose of magnesium citrate is about 0.48 mg to about 12 mg, about 0.5 mg to about 10 mg, about 0.5 mg to about 8 mg, about 0.5 mg to about 5 mg, about 0.5 mg to about 2.5 mg, about 0.5 mg to about 1 mg, about 1 mg to about 10 mg, about 1 mg to about 8 mg, about 1 mg to about 5 mg, about 1 mg to about 2 mg, about 2 mg to about 10 mg, about 2 mg to about 8 mg, about 2 mg to about 6 mg, about 2 mg to about 4 mg, about 3 mg to about 10 mg, about 4 mg to about 10 mg, about 4 mg to about 8 mg, about 4 mg to about 6 mg, about 5 mg to about 10 mg, about 5 mg to about 8 mg, about 5 mg to about 7 mg, about 5 mg to about 6 mg, about 6 mg to about 10 mg, about 6 mg to about 8 mg, or about 6 mg to about 7 mg. If other magnesium salts are substituted for magnesium citrate, the effective dose of the magnesium salt provides amount magnesium ions equivalent to that of the magnesium citrate salt.

It is intended and understood that each and every dosage of the magnesium salt described herein may be combined with each and every dosage of the oxytocin peptide described herein as if each and every combination is individually stated. For example, in some embodiments, the effective dose of the oxytocin peptide is about 0.5 µg to about 2000 µg and the effective dose of the magnesium salt administered provides about 50 µg to about 68 mg of magnesium. In some embodiments, the effective dose of the oxytocin peptide is about 15 µg to about 120 µg (e.g., about 60 µg or about 66 µg) and the effective dose of the magnesium salt administered provided is about 10 mg to about 30 mg (e.g., about 12 mg or about 24 mg) of magnesium citrate.

In some embodiments, provided is a method for treating pain comprising administering (for example by intranasal administration) to a subject in need thereof an effective dose of an oxytocin peptide and a magnesium salt, wherein the weight ratio between the dose of the oxytocin peptide administered and the dose of the magnesium or magnesium ions administered is between about 1:1 to about 1:1000, preferably between about 1:2 to about 1:200, more preferably about 1:20, about 1:30, about 1:35, about 1:40, about 1:45, about 1:50, about 1:60, or any of the OT/Mg (w) ratios described herein for the magnesium-containing oxytocin peptide formulation or composition. In some embodiments, a method is provided for treating pain comprising administering (for example by intranasal administration) to a subject in need thereof an effective dose of an oxytocin peptide and a magnesium salt, wherein the molar ratio between the dose of the oxytocin peptide administered and the dose of the magnesium or magnesium ions administered is between about 1:40 to about 1:40000, preferably between about 1:80 to about 1:8000, more preferably about 1:500, about 1:800, about 1:1000, about 1:1200, about 1:1400, about 1:1600, about 1:1800, about 1:2000, about 1:2400, about 1:3000, or any of the OT/Mg (m) ratios described herein for the magnesium-containing oxytocin peptide formulation or composition. In some of these embodiments, the oxytocin peptide is human oxytocin consisting of Cys-Tyr-Ile-Gln-Asn-Cys-Pro-Leu-Gly (SEQ. ID NO:1). In some of this embodiment, the magnesium salt is magnesium citrate. In some of these embodiments, the pain is migraine headache.

In one embodiment, a method is provided for treating pain comprises intranasally administering to a subject in need thereof a dose of about 0.5 µg to about 2000 µg (e.g., about 8 µg to about 300 µg, about 15 µg to about 120 µg or about 66 µg) of an oxytocin peptide and a dose of a magnesium salt which provides about 50 µg to about 68 mg, about 50 µg to about 34 mg, about 1 mg to about 3 mg, about 1.3 mg, or about 2.6 mg of magnesium. In one embodiment, the method comprises intranasally administering to a subject in need thereof an effective amount of a magnesium-containing oxytocin peptide formulation or composition described herein. In one embodiment, the method comprises intranasally administering to a subject in need thereof an effective amount of a magnesium-containing oxytocin peptide formulation or composition comprising between about 0.01 mg/mL and about 16 mg/mL (e.g., about 0.1 mg/mL and about 16 mg/mL) of oxytocin and between about 1 mg/mL and about 30 mg/mL of magnesium or magnesium ion. In one embodiment, the method comprises intranasally administering to a subject in need thereof an effective amount of a magnesium-containing oxytocin peptide formulation comprising between about 0.01 mg/mL and about 16 mg/mL (e.g., about 0.1 mg/mL and about 16 mg/mL or about 0.15 mg/mL and about 1.5 mg/mL) of oxytocin and between about 1% and about 25% (by weight) (e.g., about 1% to about 15% or about 10% to about 14%) of magnesium citrate. In one embodiment, the method comprises intranasally administering to a subject in need thereof an effective amount of a magnesium-containing oxytocin peptide formulation comprising between about 5 IU/mL and about 8000 IU/mL (e.g., about 50 IU/mL and about 8000 IU/mL or about 75 IU/mL and about 750 IU/mL) of oxytocin and between about 1% and about 25% (by weight) (e.g., about 1% to about 15%, about 10% to about 14%, or about 12%) of magnesium citrate. In one embodiment, the method comprises intranasally administering to a subject in need thereof an effective amount of a magnesium-containing oxytocin peptide formulation comprising between about 0.01 mg/mL and about 16 mg/mL (e.g., about 0.1 mg/mL and about 16 mg/mL or about 0.15 mg/mL and about 1.5 mg/mL) of oxytocin and between about 1% and about 25% (by weight) (e.g., about 1% to about 15%, about 8% to about 12%, or about 10%) of magnesium chloride hexahydrate. In one embodiment, the method comprises intranasally administering to a subject in need thereof an effective amount of a magnesium-containing oxytocin peptide formulation comprising between about 5 IU/mL and about 8000 IU/mL (e.g., about 50 IU/mL and about 8000 IU/mL or about 75 IU/mL and about 750 IU/mL) of oxytocin and between about 1% and about 25% (by weight) (e.g., about 1% to about 15%, about 8% to about 12%, or about 10%) of magnesium chloride hexahydrate.

In some embodiments, the effective dose of the oxytocin peptide and the magnesium salt comprises about 0.5 µg (or 0.25 IU) to about 2000 µg (or 1000 IU) of the oxytocin peptide administered in an aqueous solution containing about 0.1% to about 2.8% (w/v) of magnesium. In some embodiments, the effective dose of the oxytocin peptide and the magnesium salt comprises about 8 µg (or 4 IU) to about 1000 µg (or 500 IU) of the oxytocin peptide administered in an aqueous solution containing about 0.11% to about 1.65% (w/v) of magnesium. In some embodiments, the effective dose of the oxytocin peptide and the magnesium salt comprises about 15 µg (or 7.5 IU) to about 120 µg (or about 60 IU) (e.g., about 60 µg or 30 IU) of the oxytocin peptide administered in an aqueous solution containing about 1.1% to about 1.6% (e.g., about 1.2% or about 1.35%) magnesium. In one embodiment, the effective dose of the oxytocin peptide and the magnesium salt comprises about 60 µg (or 30 IU) of the oxytocin peptide administered in an aqueous solution containing about 1.2% or about 1.35% of magnesium.

In some embodiments, the effective dose of the oxytocin peptide and the magnesium salt comprises about 0.5 µg to about 2000 µg of the oxytocin peptide administered in an aqueous solution containing about 1% to about 25% (by weight) of magnesium citrate. In some embodiments, the effective dose of the oxytocin peptide and the magnesium salt comprises about 8 µg to about 1000 µg of the oxytocin peptide administered in an aqueous solution containing about 1% to about 15% (by weight) of magnesium citrate. In some embodiments, the effective dose of the oxytocin peptide and the magnesium salt comprises about 15 µg to about 120 µg (e.g., about 66 µg) of the oxytocin peptide administered in an aqueous solution containing about 10% to about 14% (e.g., about 12%) magnesium citrate. In one embodiment, the effective dose of the oxytocin peptide and the magnesium salt comprises about 66 µg of the oxytocin peptide administered in an aqueous solution containing about 12% of magnesium citrate.

The synergistic combination of an oxytocin peptide and a magnesium salt may be used for the treatment of any pain treatable by oxytocin, such as orofacial and craniofacial (e.g., headache pain), neck pain (e.g. occipital neuralgia) or pain in the upper extremities. Thus, provided is a method for treating pain comprising administering to a subject in need thereof an effective dose of an oxytocin peptide and a magnesium salt, wherein the pain is orofacial and craniofacial, neck pain or pain in the upper extremities, and wherein co-administration of the oxytocin peptide and the magnesium salt produces a synergistic analgesia. In one embodiment, the method comprises intranasally administering to a subject in need thereof an effective dose of an oxytocin peptide and a magnesium salt.

In some embodiments, the pain is a somatic pain. In some embodiments, the pain is a superficial somatic pain. In some embodiments, the pain is a deep somatic pain. In some embodiments, the pain is a musculoskeletal pain. In some embodiments, the pain is a visceral pain. In some embodiments, the pain is a neuropathic pain. In some embodiments, the pain is a head pain or a craniofacial pain. In some embodiments, the pain is in parts of the body other than the head and/or orofacial region. In some embodiments, the pain is a chronic pain such as a chronic pain described herein. In some embodiments, the pain is an acute pain such as an acute pain described herein. In some embodiments, the pain is a combination of one or more of the pain described herein. In some embodiment, the pain is a sharp and shooting pain associated with movement. In some embodiments, the pain is a neuropathic pain is caused by nerve injury, such as surgery related nerve injury.

In some embodiments, the pain is a head pain. In some embodiments, the pain is a facial pain. In some embodiments, the pain is a neck pain. In some embodiments, the pain is an occipital neuralgia. In some embodiments, the pain is a pain in the upper extremities. Neck and upper extremity pain includes but is not limited to examples such as nerve compression disorders (spinal stenosis), disc and vertebral diseases, diabetic neuropathy, carpal tunnel syndrome, arthritic disease, post-trauma, facet disorders, and post-herpetic neuralgia. In some embodiments, the pain is exacerbated by a psychiatric disorder, such as depression, anxiety or stress. In some embodiments, the pain is induced or exacerbated by food (e.g., caffeine, chocolate, alcohol) or by medication overuse (e.g., opiates).

Some aspects of the invention include methods for treating a trigeminal nerve-associated pain comprising administering to a subject in need thereof an effective dose of an oxytocin peptide and a magnesium salt, wherein co-administration of the oxytocin peptide and the magnesium salt produces a synergistic analgesia. In some embodiments, a method is provided for treating a trigeminal nerve-associated pain comprising administering (e.g., via intranasal administration) to a subject in need thereof an effective dose of a magnesium-containing oxytocin peptide formulation or composition described herein. The trigeminal nerve-associated pain may be selected from the group consisting of chronic, acute and procedural-related pain and combinations thereof. In some examples, the chronic pain is selected from the group consisting of trigeminal neuralgia, atypical facial pain, anesthesia dolorosa, post-herpetic neuralgia, cancer of the head and neck, migraine headaches, and temporomandibular joint pain (TMJ). In some examples, the procedural-related pain is pain arising from dental, medical, surgical or cosmetic procedures. In yet other examples, the acute pain is pain arising from a laceration, a burn, a broken bone, an injury, a headache, an abscessed tooth, dental disease, a bacterial infection or a sinus infection. Chronic, acute or procedural pain associated with the trigeminal nerve system is experienced in many syndromes and diseases including, but not limited to, trigeminal neuralgia, atypical facial pain, anesthesia dolorosa, post-herpetic neuralgia, cancer of the head and neck, migraine headaches, other types of headaches, TMJ, injuries to the face and/or head, injuries or infections of the teeth, common dental procedures and facial surgeries such as cosmetic plastic surgery.

Chronic pain in the face and head region can arise from a variety of medical conditions including but not limited to neuropathic pain, headache pain, TMJ, pain from cancer and/or cancer treatment. These pain syndromes are often not effectively treated with current medications or invasive interventions and new methods for localized pain relief in the face and head regions are needed. Accordingly, some aspects of the present invention include methods for treating a subject for trigeminal nerve-associated chronic pain by administration of an effective amount of a magnesium-containing oxytocin peptide formulation or composition described herein, wherein the administration is targeted to the trigeminal nerve system and results predominantly in analgesia to the facial, head or neck region, particularly as compared to analgesic effects in other parts of the body. The magnesium-containing oxytocin peptide formulation or composition can be administered to a patient with neuropathic pain, including but not limited to, trigeminal neuralgia, atypical facial neuralgia and post herpetic neuralgia. The magnesium-containing oxytocin peptide formulation or composition can be administered to a subject with headache pain, for example, migraine headaches or cluster headaches. The magnesium-containing oxytocin peptide formulation or composition can be administered to a subject with chronic pain arising from head or facial cancer or arising from previous treatment of head or facial cancer.

In some embodiments, the invention provides a method for treating a subject for trigeminal nerve-associated pain arising from medical, dental or cosmetic procedures comprising administration of an effective amount of a magnesium-containing oxytocin peptide formulation or composition described herein, wherein the administration is targeted to the trigeminal nerve system and results predominantly in analgesia of the facial or head regions. The methods can include a magnesium-containing oxytocin peptide formulation or composition administered to a subject undergoing a procedure selected from the group comprising medical, dental and cosmetic. The methods can include medical, dental or cosmetic procedures selected from the group comprising microdermabrasion, Botox injection, photodynamic therapy or other skin tumor ablations, hair removal (including electrolysis, laser, waxing, etc.), general facial laser treatments (including pigment removal, vascular lesions), dermal and subdermal injectable fillers (including collagen, hyaluronic acid, methylmethacrylate, hydroxyapetite, etc.), facial peels by chemical or laser applications, photofacials, collagen shrinkage procedures (including radiofrequency, HIFU, high intensity light, laser, etc.), dental procedures, tattooing, tattoo removal, piercing and treatment of scars and keloids by steroid injection. The magnesium-containing oxytocin peptide formulation or composition can be administered to a patient undergoing a procedure wherein the analgesic effect lasts the length of the procedure. The magnesium-containing oxytocin peptide formulation or composition can be administered to a patient undergoing a procedure wherein the time requirement for the procedure and for analgesia is more than 90 minutes. Administering of the magnesium-containing oxytocin peptide formulation or composition described herein can result in immediate analgesia in the patient undergoing a procedure and/or the analgesia lasts through the entire period of the procedure.

Some aspects of the present invention include methods for treating a subject for trigeminal nerve-associated pain arising from medical, dental or cosmetic procedures comprising administration of an effective amount of a magnesium-containing oxytocin peptide formulation or composition described herein, wherein the administration is targeted to the trigeminal nerve system and results in localized analgesia of the face, head or teeth. The methods can include an effective dosage amount wherein the localized analgesia lasts for the length of the procedure and continues into a post-operative period. The methods can include medical, dental or cosmetic procedures selected from the group comprising periodontal surgery, reconstructive tooth surgery, palatal surgery, tooth extraction, root canal surgery, facelifts, blepharoplasties, browlifts, rhinoplasties, cheek implants, chin implants, fat injections, lesion removal, excisional biopsies, Mohs surgery, flap reconstruction, orthognathic surgery, ophthalmic surgery, oculoplastic surgery, hair replacement surgery, extensive laser resurfacing, laceration repair, nasal fracture repair, facial bone fracture repair, burn debridement and wound cleaning. The magnesium-containing oxytocin peptide formulation or composition can be administered to a patient undergoing a medical procedure prior to injection of a vasoconstrictor into the facial or head region. The magnesium-containing oxytocin peptide formulation or composition can be administered to a patient undergoing a medical procedure wherein the analgesia lasts beyond the length of the procedure and into a post-operative time period. The magnesium-containing oxytocin peptide formulation or composition can be administered to a patient undergoing a medical procedure wherein the analgesia lasts for hours to days after the medical procedure is finished.

In a particular embodiment, the invention provides a method for treating migraine headache comprising administering (e.g., intranasally) to a human or veterinary subject in need thereof an effective dose of an oxytocin peptide and a magnesium salt, wherein co-administration of the oxytocin peptide and the magnesium salt produces a synergistic analgesia. In some embodiments, the oxytocin peptide and the magnesium salt are administered at a dose that produces an overall efficacy that is greater than the sum of the efficacies of equivalent doses of the oxytocin peptide and the magnesium salt administered individually. In some embodiments, the oxytocin peptide and the magnesium salt are administered at a dose that produces an overall analgesia or analgesic effect that is greater than the sum of the analgesia or analgesic effects of equivalent doses of the oxytocin peptide and the magnesium salt administered individually. In some embodiments, co-administration of the oxytocin peptide and the magnesium salt results in a reduction of the intensity and/or pain sensitivity (allodynia and/or hyperalgesia) of the migraine headache pain experienced by the subject that is greater than the sum of the reduction of the pain intensity and/or pain sensitivity (allodynia and/or hyperalgesia) by equivalent doses of the oxytocin peptide and the magnesium salt administered individually. In some embodiments, co-administration of the oxytocin peptide and the magnesium salt results in a reduction of the frequency of the migraine attacks experienced by the subject that is greater than the sum of the reduction of the frequency of the migraine attacks by equivalent doses of the oxytocin peptide and the magnesium salt administered individually. In some embodiments, co-administration of the oxytocin peptide and the magnesium salt results in a faster onset of analgesia or analgesic effect (e.g., reduction or alleviation of migraine headache) than any of the equivalent doses of the analgesic agents administered individually. In some embodiments, co-administration of the oxytocin peptide and the magnesium salt results in a longer lasting analgesia or analgesic effect (e.g., reduction or alleviation of migraine headache) than any of the equivalent doses of the analgesic agents administered individually.

In one embodiment, a method is provided for treating migraine headache comprising intranasally administering to a subject in need thereof (e.g., a human or veterinary patient) an effective dose of an oxytocin peptide and a magnesium salt, wherein co-administration of the oxytocin peptide and the magnesium salt produces a synergistic analgesia. In some embodiments, the oxytocin peptide is human oxytocin consisting of Cys-Tyr-Ile-Gln-Asn-Cys-Pro-Leu-Gly (SEQ. ID NO:1). In some embodiments, the effective dose of the oxytocin peptide is about 0.5 µg (or 0.25 IU) to about 2000 µg (or 1000 IU), preferably about 8 µg (or 4 IU) to about 1000 µg (or 500 IU), more preferably about 15 µg (or 7.5 IU) to about 120 µg (or 60 IU). In some embodiments, the effective dose of the magnesium salt administered provides about 50 µg to about 68 mg of magnesium. In some embodiments, the magnesium salt is magnesium chloride and/or magnesium citrate administered in an amount to provide about 50 µg to about 68 mg of magnesium. In some embodiments, the effective dose of the magnesium salt is about 0.48 mg to about 600 mg of magnesium citrate. In some embodiments, the effective dose of the magnesium salt is about 0.42 mg to about 540 mg of magnesium chloride hexahydrate. In some embodiments, the effective dose of the oxytocin peptide and the magnesium salt comprises about 15 µg (or 7.5 IU) to about 120 µg (or 60 IU) (e.g., about 60 µg or 30 IU) of the oxytocin peptide administered in an aqueous solution containing about 1.1% to about 1.54% (e.g., about 1.2% or about 1.35%) (w/v) magnesium. In some embodiments, the effective dose of the oxytocin peptide and the magnesium salt comprises about 15 µg to about 120 µg (e.g., about 66 µg) of the oxytocin peptide administered in an aqueous solution containing about 10% to about 14% (e.g., about 12%) (w/v) magnesium citrate. In one embodiment, the method for treating migraine headache comprises intranasally administering to a subject in need thereof a dose of about 0.5 µg to about 2000 µg (e.g., about 15 µg to about 120 µg or about 66 µg) of an oxytocin peptide and a dose of a magnesium salt which provides about 50 µg to about 68 mg (e.g., about 50 µg to about 34 mg of magnesium or about 1 mg to about 3 mg) of magnesium. In one embodiment, the method for treating migraine headache comprises intranasally administering to a subject in need thereof a dose of about 0.25 IU to about 1000 IU (e.g., about 7.5 IU to about 60 IU or about 30 IU) of an oxytocin peptide and a dose of a magnesium salt which provides about 50 µg to about 68 mg (e.g., about 50 µg to about 34 mg of magnesium or about 1 mg to about 3 mg) of magnesium. In one embodiment, the method comprises intranasally administering to a subject in need thereof an effective amount of a magnesium-containing oxytocin peptide formulation or composition described herein (e.g., a magnesium-containing oxytocin peptide formulation or composition comprising between about 0.01 mg/mL and about 16 mg/mL of oxytocin and between about 1 mg/mL and about 30 mg/mL of magnesium or magnesium ion). In one embodiment, the method comprises intranasally administering to a subject in need thereof an effective amount of a magnesium-containing oxytocin peptide formulation comprising between about 0.01 mg/mL and about 16 mg/mL (preferably between about 0.1 mg/mL and about 2 mg/mL, more preferably about 0.15 mg/mL and about 1.5 mg/mL, or about 0.33 mg/mL) of oxytocin and between about 1% to about 25% (by weight) (e.g., about 10% to about 14%) of magnesium citrate. In one embodiment, the method comprises intranasally administering to a subject in need thereof an effective amount of a magnesium-containing oxytocin peptide formulation comprising between about 5 IU/mL and about 8000 IU/mL (preferably between about 50 IU/mL and about 1000 IU/mL, more preferably about 75 IU/mL and about 750 IU/mL, or about 150 IU/mL) of oxytocin and between about 0.1% to about 2.8% (by weight) (e.g., about 1.1% to about 1.54%) of magnesium.

Some aspects of the invention include methods for treating a cervical nerve-associated pain comprising administering to a subject in need thereof an effective dose of an oxytocin peptide and a magnesium salt. In some embodiments, co-administration of the oxytocin peptide and the magnesium salt produces a synergistic analgesia. In some embodiments, the method is for treating an upper cervical nerve-associated pain. There are eight cervical nerves (C1-C8) on either side of the body. The upper cervical nerves (C1-C4) provide innervation and carry pain information from the back of the head, the neck, and the upper shoulders. The lower cervical nerves (C5-C8) carry pain information from the lower shoulders, the arms, and the hands, including the fingers. "Cervical nerve-associated pain" as used herein, unless otherwise specified, refers to pain which arises in a tissue innervated by the cervical nerve and/or is associated with damage or trauma to the cervical nerve. In some embodiments, a cervical nerve-associated pain is associated with an upper cervical nerve such as the C1, C2, C3 and/or C4 nerves. "Upper cervical nerve-associated pain" as used herein refers to pain which arises in a tissue innervated by one or more of the upper cervical nerves and/or is associated with damage or trauma to one or more of the upper cervical nerves.

In some embodiments, a method is provided for treating a cervical nerve-associated pain comprising administering (e.g., via intranasal administration) to a subject in need thereof an effective dose of a magnesium-containing oxytocin peptide formulation or composition described herein. In some embodiments, the method comprises treatment of a chronic or on-going pain in the neck, shoulder and/or upper extremities. In some embodiments, the method comprises treatment of a cervical nerve-associated pain. In some embodiments, the method comprises treatment of an upper cervical nerve-associated pain (e.g. a neck pain). In some embodiments, the method comprises treatment of a lower cervical nerve-associated pain (e.g., a pain in the shoulder, the lower arm or the hands). In some embodiments, the method comprises treatment of occipital or neck pain. In some embodiments, the method comprises treatment of occipital neuralgia. In some embodiments, the method comprises treatment of shoulder pain. In some embodiments, the method comprises treatment of pain in the lower arm or the upper arm. In some embodiments, the effective dose of the oxytocin peptide administered is about 50 to about 8000 IU, about 50 to about 2000 IU, about 50 IU to 150 IU, or about 150 to 2000 IU. In some embodiments, the effective dose is about 50 IU to about 150 IU, about 50 IU to about 100 IU, about 60 IU to about 90 IU, about 100 IU to about 150 IU, about 120 IU to about 150 IU, or about 75 IU to about 150 IU. In some embodiments, the effective dose is about 150 IU to about 2000 IU, about 150 IU to about 1000 IU, about 150 IU to about 500 IU, about 200 IU to about 2000 IU, about 200 IU to about 1000 IU, about 200 IU to about 500 IU, about 250 IU to about 2000 IU, about 250 IU to about 1000 IU, about 250 IU to about 500 IU, about 500 IU to about 2000 IU, or about 500 IU to about 1000 IU. In some embodiments, the effective dose is about 100 IU to about 1000 IU. In some embodiments, the effective dose of the magnesium salt administered provides about 50 µg to about 34 mg, or about 1 mg to about 3 mg of magnesium or magnesium ions ($Mg^{2+}$). In some embodiments, the effective dose of the magnesium salt administered provides about 50 µg to about 1 mg, about 0.5 mg to about 5 mg, about 3 mg to about 15 mg, or about 5 mg to about 30 mg of magnesium or $Mg^{2+}$. In some embodiments, the effective dose of the magnesium salt administered provides about 1.2 mg, or about 2.4 mg of magnesium or $Mg^{2+}$. In general, a higher dose of oxytocin peptide formulation is required for the treatment of a cervical-nerve associated pain than that for the treatment of a trigeminal nerve-associated pain; and a higher dose of oxytocin peptide formulation is required for the treatment of a lower cervical-nerve associated pain than that for the treatment of a higher cervical nerve-associated pain.

Kits

Provided herein are kits for carrying out any of the methods described herein. Kits are provided for use in treatment and/or prevention of pain. In some embodiments, the kit comprises an oxytocin peptide and a magnesium salt, wherein the oxytocin peptide and the magnesium salt are in an amount that produces a synergistic analgesia when used in the treatment of pain, and a device for craniofacial mucosal administration (e.g., intranasal administration) in suitable packaging. Kits may further comprise a protease inhibitor and/or at least one absorption enhancer. Other kits may further comprise instructions providing information to the user and/or health care provider for carrying out any one of the methods described herein.

Also provided is a kit comprising a magnesium-containing oxytocin peptide formulation described herein contained in a device for craniofacial mucosal administration (e.g., a device for intranasal administration such as a nasal pump apparatus) and suitable packaging. The kit may further comprise instructions for administering the magnesium-containing oxytocin peptide formulation in a subject in need thereof.

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

EXAMPLES

The invention can be further understood by reference to the following examples, which are provided by way of illustration and are not meant to be limiting.

Example 1

Effect of Magnesium Chloride or Magnesium Lactate in a Rat Model of Facial Thermal Nociception The heat from a projector lamp was focused on the pre-shaved cheek of rats and the intensity was varied to obtain a withdrawal response with a latency of between 6.5 and 8.5 seconds. The intensity applied to achieve such latencies was recorded for each animal. Once stable/acceptable baseline values were obtained, the average latencies for each rat were calculated. After baseline cheek withdrawal latencies were determined for all rats, each rat received a single nasal administration of either normal saline, 15% magnesium chloride in water, or 1% magnesium lactate in water according to the method developed by Frey (Thorne, et al. *Neuroscience.*, 127: 481-496 (2004)). Briefly, rats (under urethane anesthesia) were placed in a supine position with a rolled pad (2×2 gauze) inserted under the dorsal neck to extend the head back toward the supporting surface. The upper surface of the neck was kept horizontal throughout the dosing procedure to maintain the drug solution in the nasal cavity and minimize dripping down the nasopharynx. A 6 μL drop of the respective drug solution was delivered off the tip of a small pipette and presented to the nares on the left side of the rat while occluding the opposite nares. One drop was administered every 2 minutes, alternating between each nares (thus amounting to a four minute interval between doses to the same nares). Each nostril received 4 drops, totaling a combined volume of 48 μL (8 drops of 6 μL each). Drug solutions were coded in order to keep the experimenter blinded as to the substances delivered. Left cheek withdrawal latencies in response to radiant heat stimulation were then measured over the next 3 hours. Withdrawal latencies were measured prior to nasal administration and at 1, 2, and 3 hours post-treatment.

Withdrawal latencies in response to thermal stimuli (noxious heat) were recorded as an index of thermal sensitivity. Increased latencies were considered indicative of analgesia/anti-nociception. Nasal application of saline transiently raised response latencies of rats by approximately 1.2 s, suggesting a mild analgesic effect—an effect that was gone by the 2 hour testing point where latencies were actually below baseline responsiveness (FIG. 1). Application of 1% magnesium lactate also produced a mild analgesic effect, raising response latencies by approximately 1.5 s. Unlike saline application, however, latencies after magnesium lactate application were still substantially elevated at both the 2 and 3 hour time points. Application of 15% magnesium chloride in water produced a strong analgesic effect when compared to nasal saline treated rats at 1 hour after testing, with analgesia continuing at 2 and 3 hours after dosing.

To our knowledge, this surprising result is the first such finding that nasal application of magnesium salts is analgesic.

Example 2

Dose-Dependence of Analgesic Effect of Nasal Application of Magnesium Citrate in a Rat Model of Facial Thermal Nociception One of 4 concentrations of dibasic magnesium citrate (1:1 Mg/citrate) was applied to rats and the effects of these applications on responses to noxious thermal stimulation of the face were assessed as described above. Each rat received a single nasal administration of 3, 6, 10, or 12% magnesium citrate in water (6 rats/group) according to the method described above. Left cheek withdrawal latencies in response to radiant heat stimulation were then measured over the following 300 minutes. Withdrawal latencies were measured prior to nasal administration and at 15, 30, 45, 60, 120, 180, 240, and 300 min post-treatment.

The magnesium citrate was prepared by adding USP anhydrous magnesium carbonate ($MgCO_3$, Acros Organics, 9.5 g) to citric acid solution (22 g of citric acid monohydrate in 80 ml $dH_2O$) heated to 60° C. and stirring until the mixture completely clarifies. The mixture was then filtered. Absolute anhydrous ethanol was used to precipitate and wash the magnesium citrate product, which was dried on a hot plate at 60° C.

Figure 2:
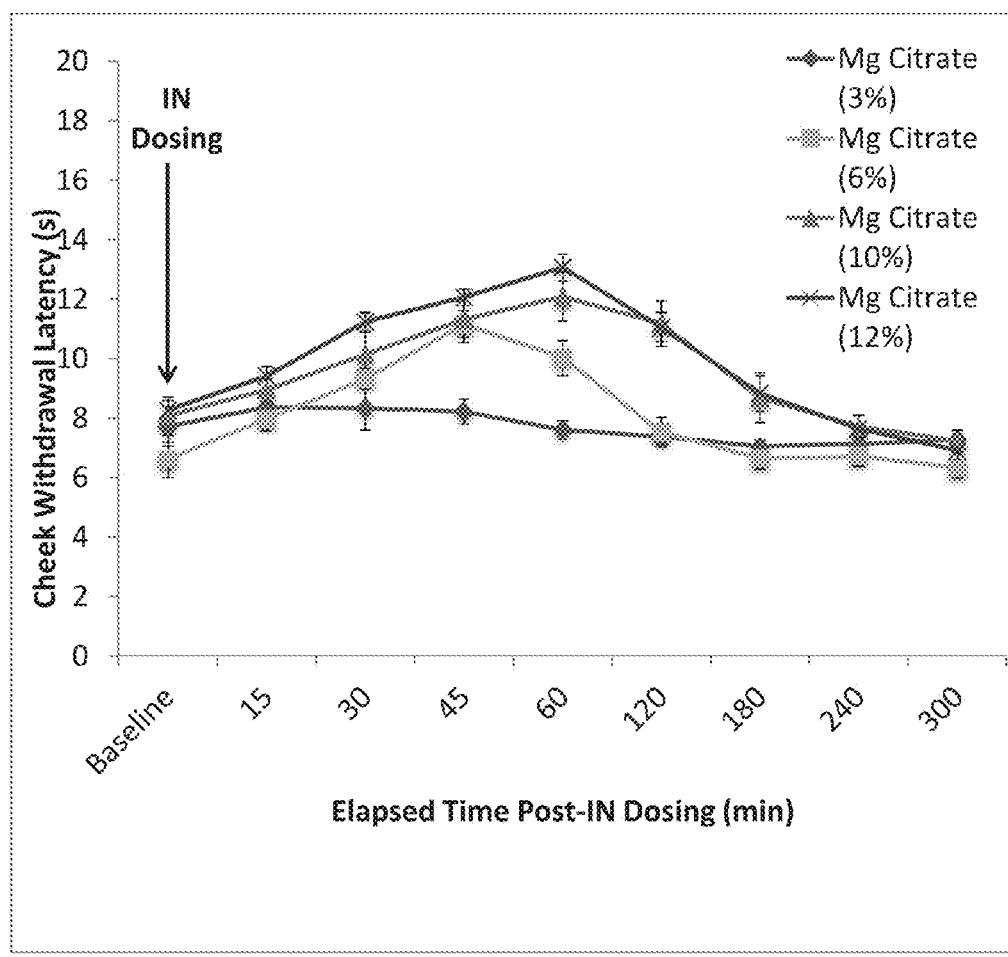
FIG. 2. Dose-dependence of analgesic effect of nasal application of magnesium citrate in a rat model of facial thermal nociception. Rats were treated with 3, 6, 10, or 12% magnesium citrate, and withdrawal response latency was measured just prior to treatment and at 15, 30, 45, 60, 120, 180, 240, and 300 min post-treatment.

Nasal application of aqueous solutions of magnesium citrate produced a clear dose-dependent analgesic effect in rats as indicated by an elevation in latency to withdrawal in response to noxious heating of the cheek (FIG. 2). Thus, with positive findings for 3 out of 3 magnesium salts, these experiments have provided evidence for a general principle that nasal application of salts that provide magnesium ions in aqueous solution are analgesic.

Example 3

Dose-dependence of Analgesic Effect of Nasal Application of Oxytocin in a Rat Model of Facial Thermal Nociception One of 3 doses of oxytocin in buffered saline was applied to rats and the effects of these applications on responses to noxious thermal stimulation of the face were assessed as described above. Each rat received a single nasal administration of 1, 4, or 8 µg oxytocin in aqueous solution (6 rats/group) according to the method described above. Left cheek withdrawal latencies in response to radiant heat stimulation were then measured over the following 300 minutes. Withdrawal latencies were measured prior to nasal administration and at 15, 30, 45, 60, 120, 180, 240, and 300 min post-treatment.

Figure 3:
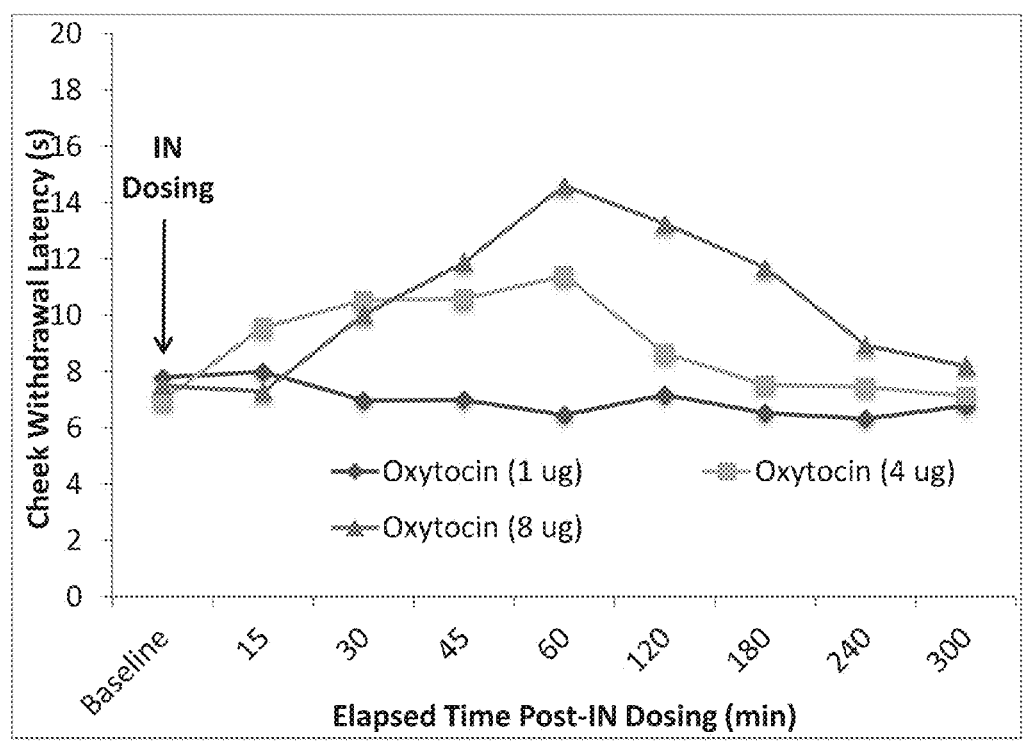
FIG. 3. Dose-dependence of analgesic effect of nasal application of oxytocin in a rat model of facial thermal nociception. Rats were treated with 1, 4, or 8 µg oxytocin, and withdrawal response latency was measured just prior to treatment and at 15, 30, 45, 60, 120, 180, 240, and 300 min post-treatment.

Nasal application of aqueous solutions of oxytocin produced a clear dose-dependent analgesic effect in rats as indicated by an elevation in latency to withdrawal in response to noxious heating of the cheek (FIG. 3). Both 4 and 8 µg of nasally applied oxytocin produced a robust increase in latency to withdrawal in response to noxious cheek heating. However, 1 µg of nasally-applied oxytocin was analgesically sub-therapeutic, exhibiting no increase (and, in fact, a slight decrease) in withdrawal latency. This dose-dependent analgesic effect of nasal oxytocin peptide is consistent with the analgesic effect we have previously described for oxytocin.

Example 4

Analgesic Effects of Drug Combination Solutions with Varying Ratios of Magnesium Salt to Oxytocin Example 4A Magnesium Citrate/Oxytocin Combination Aqueous solutions containing a combination of magnesium citrate at one of 3 concentrations with oxytocin at one of 3 doses were applied nasally in rats and changes in withdrawal response latency were measured as above. Each rat received a single nasal administration of 1, 4, or 8 µg of oxytocin in aqueous solution containing 3, 6, or 12% magnesium citrate according to the method described above. Left cheek withdrawal latencies in response to radiant heat stimulation were then measured over the following 300 minutes. Withdrawal latencies were measured prior to nasal administration and at 15, 30, 45, 60, 120, 180, 240, and 300 min post-treatment.

Difference scores were generated for each time point after dosing by comparing the respective withdrawal response latency to pre-dosing (baseline) values. As a standard means of assessing combination effects, difference scores were also calculated for effects of nasal magnesium citrate alone (from Experiment 2 above) and for effects of nasal oxytocin alone (from Experiment 3 above). The predicted additive effects of a combination of oxytocin dose plus magnesium citrate concentration were then calculated and compared to the measured difference score determined by actual dosing of these combinations. If the measured combination effects exceeded the predicted additive effects, this is, by definition, demonstrative of pharmacologic synergy. This synergy can be evidenced either by an unexpected, supra-additive increase in latency, earlier than expected onset of analgesia, or longer than expected duration of effect.

Figure 4A:
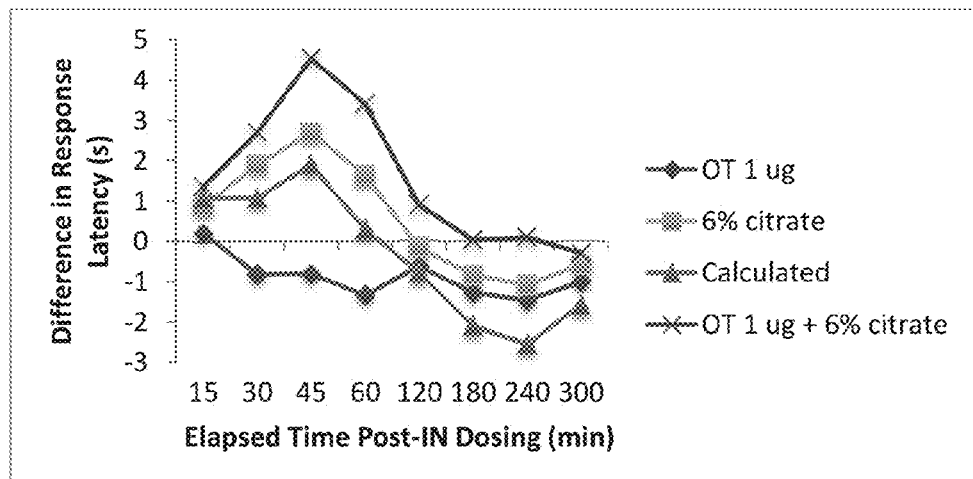
FIG. 4A. Analgesic effects of nasal application of 1 µg oxytocin in a 6% magnesium citrate solution. Difference in response latency at 15, 30, 45, 60, 120, 180, 240, and 300 min post-treatment was determined for 1 µg oxytocin alone, 6% magnesium citrate alone, calculated additive effect of 1 µg oxytocin in 6% magnesium citrate solution, and actual application of 1 µg oxytocin in 6% magnesium citrate solution.
Figure 4B:
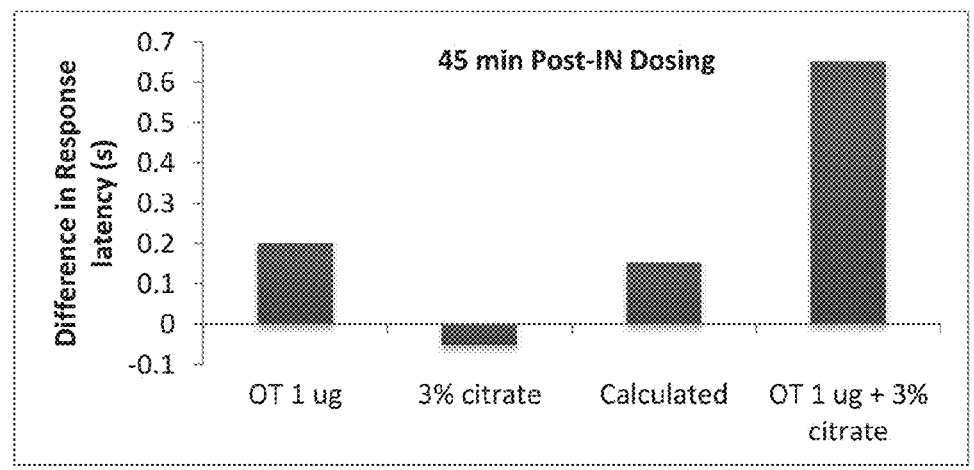
FIGS. 4B, 4C, and 4D. Analgesic effects of nasal application of 1 µg oxytocin in a 3, 6, or 12% magnesium citrate solution. Difference in response latency at 45 min post-treatment was determined for oxytocin alone, magnesium citrate alone, calculated additive effect of oxytocin in magnesium citrate solution, and actual application of oxytocin in magnesium citrate solution.
Figure 4C:
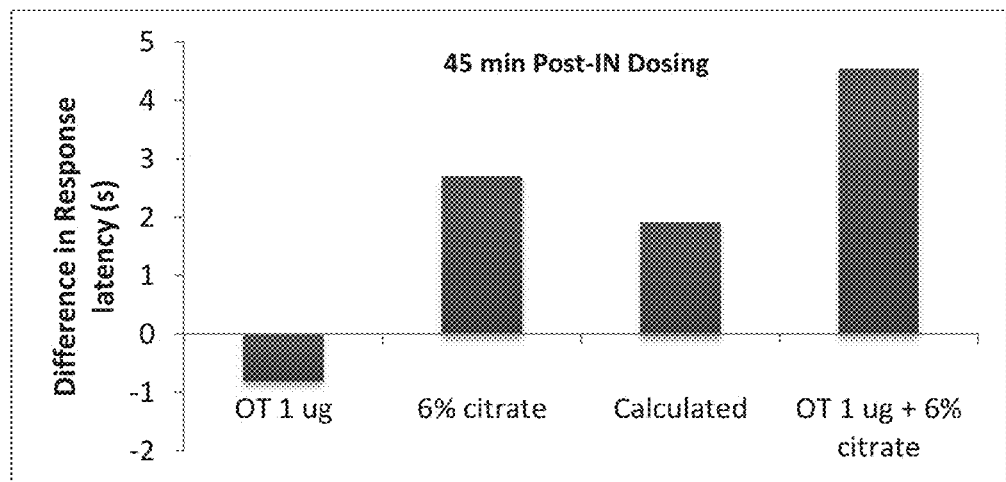
Figure 4D:
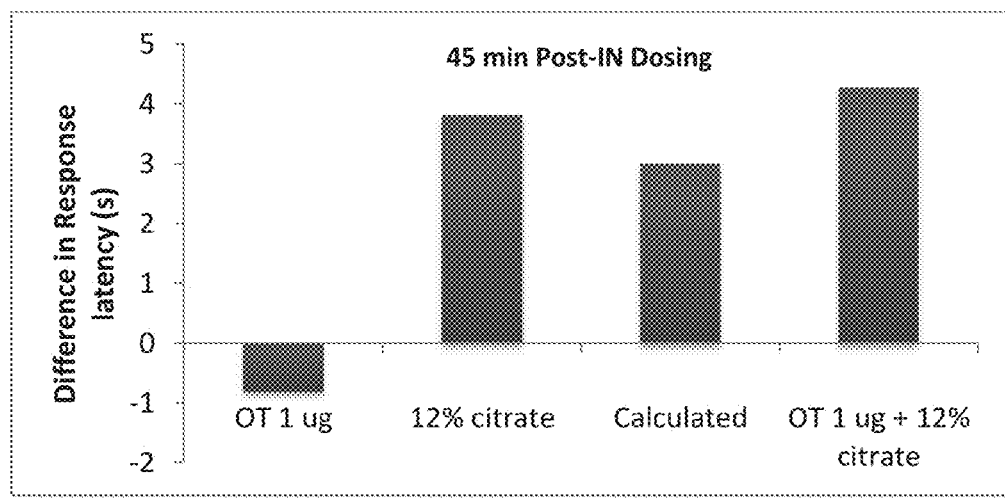

The nasal application of combinations of various doses of oxytocin and various concentrations of magnesium citrate demonstrated surprising levels of analgesia that, in many cases, far exceeded that which would be expected based on the effects of oxytocin or magnesium citrate alone. For a dose of oxytocin which was ineffective or subtherapeutic on its own (1 µg), the addition of 3, 6, or 12% magnesium citrate resulted in substantial analgesia. For all time points after dosing, the observed increase in response latency over baseline after dosing with 1 µg oxytocin in 6% magnesium citrate exceeded the effects that would be predicted or expected from adding the effects of 1 µg oxytocin alone plus that of 6% magnesium citrate alone (FIGS. 4A and 4C). Similar supra-additive effects were seen at 45 minutes after dosing for 1 µg oxytocin in 3 or 12% magnesium citrate (FIGS. 4B and 4D).

Figure 5:
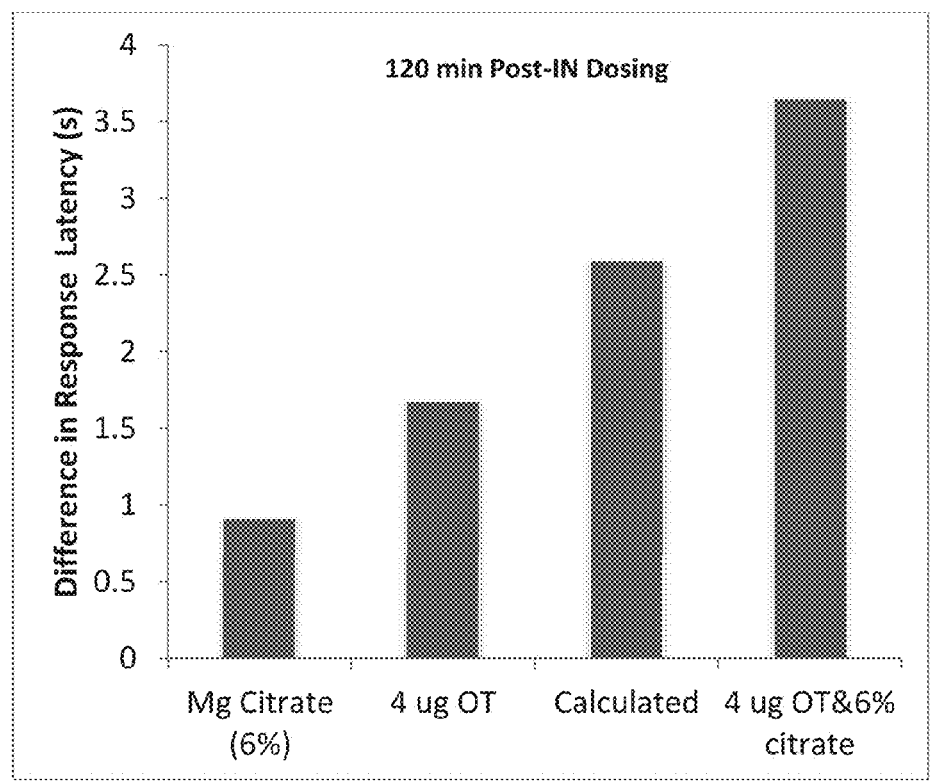
FIG. 5. Analgesic effects of nasal application of 4 µg oxytocin in a 6% magnesium citrate solution. Difference in response latency at 120 min post-treatment was determined for 4 µg oxytocin alone, 6% magnesium citrate alone, calculated additive effect of 4 µg oxytocin in 6% magnesium citrate solution, and actual application of 4 µg oxytocin in 6% magnesium citrate solution.
Figure 6A:
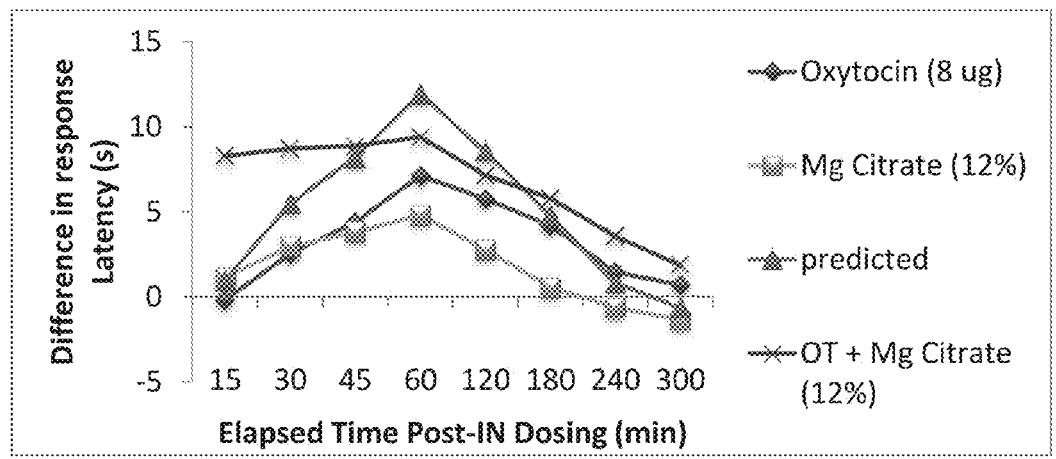
FIG. 6A. Analgesic effects of nasal application of 8 µg oxytocin in a 12% magnesium citrate solution. Difference in response latency at 15, 30, 45, 60, 120, 180, 240, and 300 min post-treatment was determined for 8 µg oxytocin alone, 12% magnesium citrate alone, calculated additive effect of 8 µg oxytocin in 12% magnesium citrate solution, and actual application of 8 µg oxytocin in 12% magnesium citrate solution.
Figure 6B:
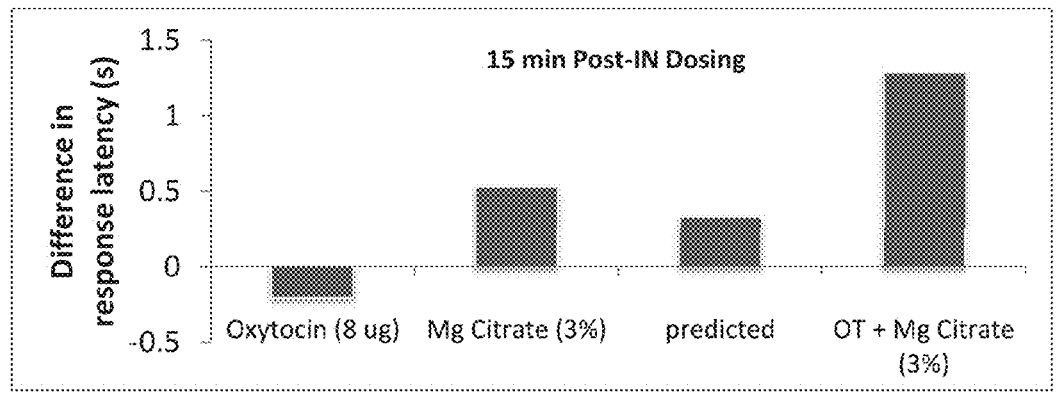
FIGS. 6B, 6C, and 6D. Analgesic effects of nasal application of 8 µg oxytocin in a 3, 6, or 12% magnesium citrate solution. Difference in response latency at 15 min post-treatment was determined for oxytocin alone, magnesium citrate alone, calculated additive effect of oxytocin in magnesium citrate solution, and actual application of oxytocin in magnesium citrate solution.
Figure 6C:
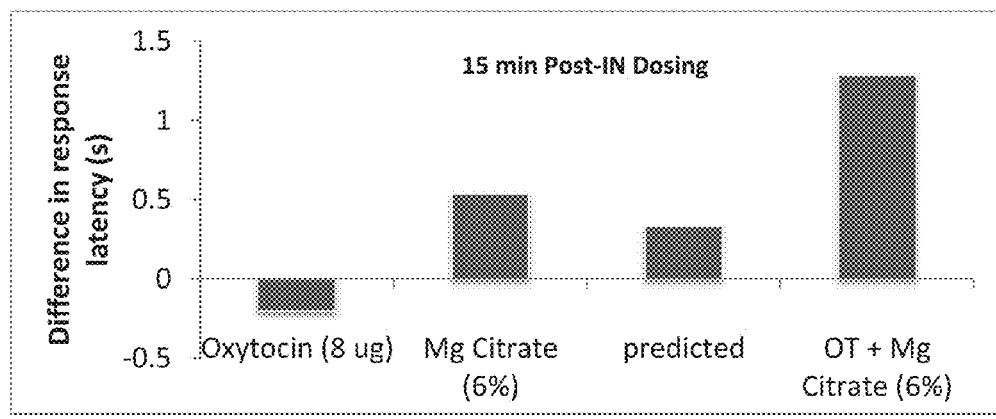
Figure 6D:
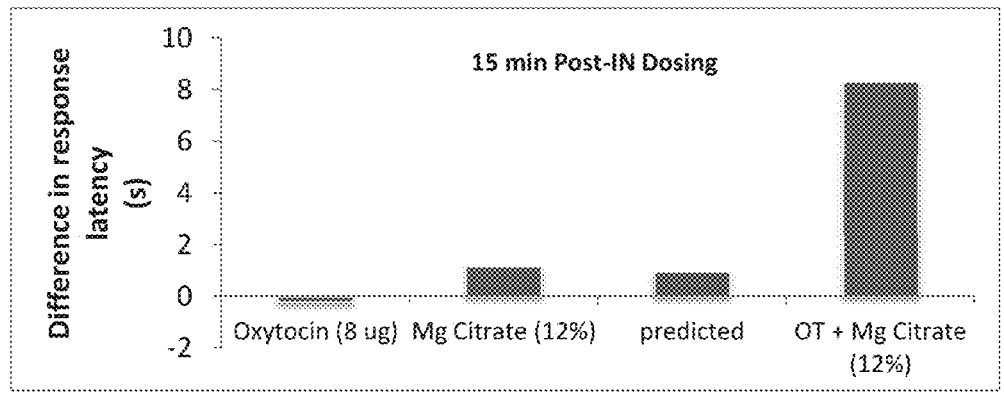

For at least some time points, supra-additive effects were also seen for a moderately analgesic dose of oxytocin (4 µg) when applied in a magnesium citrate formulation. For example, FIG. 5 demonstrates that, at 120 min after dosing, the observed analgesic effect substantially exceeded that expected or predicted by adding the effects of the two components. For a dose of oxytocin which is strongly analgesic in this model (8 µg), nasal application in a magnesium citrate solution substantially increased the efficacy of that dose. At most time points, the observed analgesia after administration of 8 µg of oxytocin in a 12% magnesium citrate solution exceeded that predicted by the addition of the effects of the two components individually (FIGS. 6A and 6D). Another key finding is that the combination shows not only a greater amplitude of effect (i.e., difference in latency from baseline), but also earlier onset of effect and longer duration of analgesia. Similar supra-additive effects were observed at some time points after nasal application of 8 µg oxytocin in 3 or 6% magnesium citrate. For example, FIGS. 6B and 6C demonstrate that, at 15 min after dosing, the observed analgesic effect substantially exceeded that expected or predicted by adding the effects of the two components.

Example 4B

Magnesium Sulfate/Oxytocin Combination

Aqueous solutions containing a combination of magnesium sulfate with oxytocin were applied nasally in rats and changes in withdrawal response latency were measured as above. Each rat received a single nasal administration of 8 µg of oxytocin in aqueous solution containing 20% magnesium sulfate heptahydrate ($MgSO_4 \cdot 7H_2O$, MW 246.5) according to the method described above. Left cheek withdrawal latencies in response to radiant heat stimulation were then measured over the following 300 minutes. Withdrawal latencies were measured prior to nasal administration and at 15, 30, 45, 60, 120, 180, 240, and 300 min post-treatment.

Figure 7:
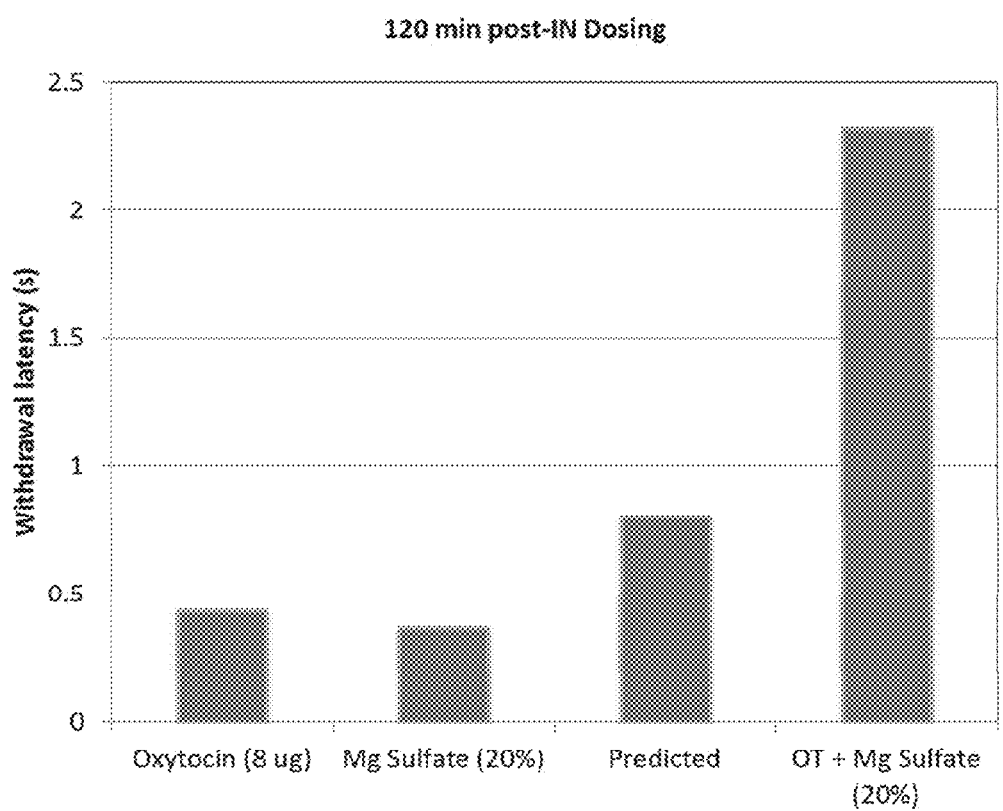
FIG. 7. Analgesic effects of nasal application of oxytocin (8 µg) in a 20% magnesium sulfate heptahydrate solution at 120 min post intranasal dosing.

The observed increase in response latency over baseline after dosing with 8 µg oxytocin in 20% magnesium sulfate heptahydrate exceeded the effects that would be predicted or expected from adding the effects of 8 µg oxytocin alone plus that of 20% magnesium sulfate heptahydrate alone. FIG. 7 demonstrates that, at 120 min after dosing, the observed analgesic effect substantially exceeded that expected or predicted by adding the effects of the two components.

The results of these experiments clearly indicate that: 1) nasal application of various concentrations of magnesium salts surprisingly produce analgesia; 2) as expected, nasal application of an oxytocin peptide is strongly and dose-dependently analgesic, and 3) addition of magnesium salts in various concentrations to subtherapeutic, moderately analgesic, and strongly analgesic doses of oxytocin surprisingly and unpredictably produce supra-additive (synergistic) analgesia.

Example 5

Exemplary Preparation of a Magnesium-Containing Oxytocin Peptide Formulation

Example 5A

The drug product formulation, which is hypertonic and targeted at pH 4.5, consists of Oxytocin USP (150 IU/mL); Magnesium Chloride USP (as the hexahydrate or anhydrous salt); Citric Acid USP (as the anhydrous or monohydrate form); Sodium Hydroxide NF; and Sterile Water for Injection USP. The quantitative composition is provided in Table 1. All ingredients meet the compendial (USP/NF) requirements from the corresponding monographs.

TABLE 1

| Component | Composition mg/mL | wt % | Function |
|---|---|---|---|
| Oxytocin USP[1] | 150 IU | Footnote 1 | Active ingredient |
| Magnesium Chloride USP[2] | 101.7 | 10.2 | Chelating system |
| Citric Acid USP[3] | 9.6 | 0.96 | |
| Sodium Hydroxide NF | qs pH 4.5 | qs pH 4.5 | pH adjustment |
| Sterile Water for Injection USP | qs | qs | Solvent |
| Total | ca. 1000 | 100 | |

[1]The exact amount of oxytocin to be used is based on its oxytocic activity from the supplier certificate of analysis.
[2]The composition values for magnesium chloride represent those of the hexahydrate; the anhydrous salt may be used as well, with corresponding adjustment of composition.
[3]The composition values for citric acid represent those of the anhydrous form; the monohydrate may be used as well, with corresponding adjustment of composition.

The drug product is manufactured by dissolving the ingredients in Sterile Water for Injection, sterile filtering and filling into a vial with a snap on preservative free pump, and is tested in general accordance with the July 2002 FDA nasal spray guidance.

In one example, a 10-L batch of the magnesium-containing oxytocin formulation according to the composition provided in Table 1 was prepared as following: Filled the formulation vessel with water to about 60% of the required batch volume. While stirring at ambient temperature, added in the following order the required quantities of: Sodium Chloride, Citric Acid and Magnesium Chloride hexahydrate. The materials dissolved readily. No heat was required, just gentle stirring. Adjusted the pH of the solution to 4.5 with the addition of 1N NaOH. (If over-titrated, 10% HCl could be used to back-titrate to pH 4.5.) Added the required amount of oxytocin and stirred until dissolved. Added water to bring the batch to the final weight/volume. Stirred until the solution was homogenous.

Example 5B

The drug product formulation, which is isotonic and targeted at pH 4.5, consists of Oxytocin USP (150 IU/mL); Magnesium Citrate, Sodium Chloride USP; Sodium Acetate Trihydrate USP; Glacial Acetic Acid USP; and Sterile Water for Injection USP. Quantitative compositions are provided in Table 2. The target pH of 4.5 is selected based on the optimal formulation stability at or near this pH (Hawe, et al. Pharmaceut. Res. 26:1679-1688 (2009)). All ingredients meet the compendial (USP/NF) requirements from the corresponding monographs.

To prepare a stock oxytocin solution, lyophilized oxytocin (2 mg) is added to 1 mL of water (USP), 0.9% physiological saline or phosphate buffered saline in a 5 mL glass vessel. The solution is stirred until all the oxytocin is dissolved, and the pH is adjusted to between 3.5 and 8.5, producing 1 mL of a 2 mg/mL (about 1000 IU/mL) liquid oxytocin formulation.

For use as clinical material oxytocin and the excipients are manufactured under current Good Manufacturing Practice and undergo terminal sterilization (aseptic filtration through a 0.2 micron membrane filter) prior to filling within a glass reservoir bottle and sealing with a pump actuator. Various formulation concentrations can be produced from this example by increasing or decreasing the oxytocin amount. Approximately, 10 doses of oxytocin are obtained from this 1 mL batch volume.

TABLE 2

| Ingredient | Concentration (mg/mL) |
|---|---|
| Oxytocin USP | 0.283 |
| Magnesium Citrate | 120 |
| Sodium Chloride USP | 4.675 |
| Sodium Acetate Trihydrate USP | 6.805 |
| Citric Acid USP | pH 4.5 |
| Sterile Water for Injection USP | qs |

Example 6

Treatment of Chronic and High Frequency Episodic Migraine Headache Using a Magnesium-Containing Oxytocin Peptide Formulation

Example 6A

Several patients with high frequency migraine headache were seen by a headache specialist in a clinic at a major hospital in Southern California, USA. The specialist gave the patients three nasal sprays, marked A, B, and C to take home. The patients were to take one of the vials each time when they experienced their next 3 migraine headaches and assess the extent of pain relief experienced as a result of the spray. The three vials contained liquid sufficient to deliver 48 milligrams of magnesium citrate adjuvant in a 12% solution (vial A), 66 micrograms of oxytocin (vial B), or 48 mg of magnesium citrate adjuvant in a 12% solution plus 66 micrograms of oxytocin (vial C). The patients reported no benefit from vial A in terms of pain relief, some benefit from vial B, and much stronger pain relief from vial C. These results demonstrate a synergistic effect of oxytocin and magnesium containing adjuvant in relieving craniofacial pain.

Example 6B

Ninety human patients suffering from migraine with or without aura are enrolled in a double-blinded, randomized, parallel study. Each subject participates for 90 days. Stage 1 involves 28 days of baseline (screening) during which patients record headache occurrence and taking of their standard medication. Stage 2 will be 56 days during which patients take the nasal oxytocin/magnesium citrate formulation when they have a headache. Sixty patients are assigned to the active (oxytocin/magnesium formulation), 30 are assigned to the placebo group.

Eligibility for the study is determined by telephone interview and during a first visit at the study center. During the first visit of potential participants at the study center a medical history is taken and a medical exam is performed. In particular, the diagnosis of chronic or high frequency episodic migraine headache with or without aura is established by one skilled in the art. If participants meet inclusion criteria and no exclusion criteria apply written informed consent is obtained. Demographic and medical data are recorded.

The pain assessment tool is a VRS-4. This tool is self-reported and requires subjects to rate their pain level on a 4-category scale (severe, moderate, mild, none). Subjects use a secure mobile ePRO device to enter their pain scores. Subjects are trained on completing the VRS-4, using the mobile device, during their screening visit.

During the 28-day Stage 1 screening period (after a subject signs informed consent), subjects enter headache (migraine or tension-type) pain scores once daily. If a subject does not experience a headache on a given day, no pain scores are entered. The number of migraine and/or tension-type headaches recorded during the screening period will be used to determine eligibility for the study. Patients recording 15 or more headache days/28 day period are included as chronic migraineurs; subjects recording between 8 and 14 headache days/28 day period are enrolled as high frequency episodic migraineurs.

During Stage 1 and Stage 2: On days that a headache occurs, subjects nasally administer the magnesium-containing oxytocin peptide formulation. Subjects record their pain scores at headache onset, and then 30 minutes and 1, 2, 3, 4, 5, and 6 hours after initial study drug administration. On days that headaches do not occur, subjects do not take study drug and don't record any pain scores.

The analgesic efficacy of the oxytocin/magnesium citrate formulation is assessed by comparing post-dosing effects on pain intensity, latency to onset of analgesia, duration of analgesia, and headache frequency reduction when compared to nasal placebo treatment.

Example 7

Treatment of Neck and Shoulder Pain Using a High Dose Oxytocin Formulation

A patient with chronic tension-type headache reported having intense pain in their head, neck and shoulders. The patient took 4 sprays of 7.5 IU/spray oxytocin for a dose of 30 units, at which point their headache pain was gone, but the neck and shoulder pain remained. The patient continued to dose and eventually took additional 8-10 sprays, or a total of 60-75 IU, at which point the neck and shoulder pain receded and ceased. Thus, a higher dose was necessary to affect neck and shoulder pain than was necessary to inhibit head pain in the same patient.

Example 8

Figure 8:
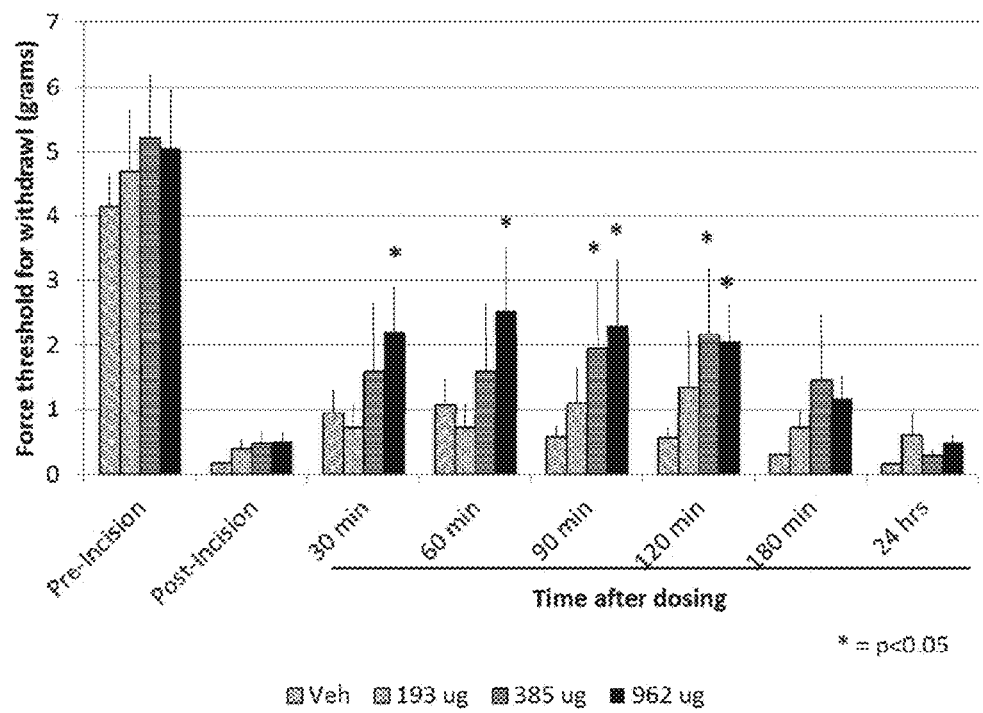
FIG. 8. Analgesic effects of nasal oxytocin at 0 (vehicle), 193, 385 and 768 µg doses in a rat paw inflammation model observed at 30 min, 60 min, 90 min, 120 min, 180 min, and 24 hours post intranasal dosing.

Analgesic Effects of Nasal Oxytocin on Cervical Nerve-Associated Pain in a Rat Paw Inflammation Model The analgesic effect of nasally administered oxytocin on cervical nerve-associated inflammatory pain was assessed in a rat paw inflammation model (Martin et al., *Pain* 1999, 82:199-205). Oxytocin was nasally administered at one of three doses (193, 385 or 768 micrograms in 48 microliters) and force withdrawal thresholds in grams were determined following mechanical stimulation of the inflamed area (forepaw), at regular intervals over the next three hours, and compared against those of vehicle (phosphate buffered saline) treated rats. Injection of complete Freund's adjuvant into the left forepaw of rats produced a robust inflammation of that paw as well as a substantial decrease in the force necessary to elicit a withdrawal response (mechanical allodynia). The results are presented in FIG. 8. The lowest dose of oxytocin was ineffective in increasing pain thresholds, whereas the higher 2 doses produced a statistically significant partial reversal of the mechanical allodynia resulting from inflammation. These results are consistent with nasal oxytocin being analgesic for pain associated with cervical nerves.

Analgesic effect of a magnesium-containing oxytocin peptide formulation on cervical nerve-associated inflammatory pain is tested in the rat paw inflammation model. A series of dosages is administered following the same procedure as above. The force withdrawal threshold in grams is determined at regular intervals over a 24-hour period post intranasal dosing of the formulation.

Example 9

Treatment of Neck Pain Using a Magnesium-Containing Oxytocin Peptide Formulation A 20-year-old female patient who had been in a recent auto accident suffered from severe neck pain. The patient was treated with the magnesium-containing oxytocin formulation of Example 5A. The neck pain was measured on an 11-point numerical pain rating scale. The patient was asked to assign a number to her pain relative to her own internal perception—a "1" is threshold level pain, or just barely painful, and a "10" is the worst pain the patient can imagine (A zero on this scale means that there is no pain). When 60 IU of oxytocin (contained in 400 µL of the formulation) was applied to the patient's nose in 4 sprays of 100 µL per spray, the patient's neck pain was reduced from a rating of "9" to a rating of "4" on the 11 point numerical pain rating scale. The patient's pain relief occurred within 10 minutes of treatment.

The analgesic effect with the magnesium-containing oxytocin formulation occurred earlier than was expected, in comparison to that of an oxytocin formulation that does not contain a magnesium salt, where analgesic effects usually occur much later. For example, in a study with a commercial oxytocin formulation (Syntocinon®), the onset to substantive analgesia in chronic migraine headache was not until 2-4 hours after dosing (Yeomans, et al. *Cephalalgia* 2013, 33(8 Supplement) 1-291, p 59).

Exemplary Embodiments

The invention is further described by the following embodiments. The features of each of the embodiments are combinable with any of the other embodiments where appropriate and practical.

Embodiment 1

In one embodiment, the invention provides a method for treating pain comprising administering to a subject in need thereof an effective dose of an oxytocin peptide and a magnesium salt, wherein co-administration of the oxytocin peptide and the magnesium salt produces a synergistic analgesia.

Embodiment 2

In a further embodiment of embodiment 1, the oxytocin peptide is administered concurrently with the magnesium salt.

Embodiment 3

In a further embodiment of embodiment 1, the oxytocin peptide is administered before or after administration of the magnesium salt.

Embodiment 4

In a further embodiment of any one of embodiments 1 to 3, the oxytocin peptide is administered via craniofacial mucosal administration.

Embodiment 5

In a further embodiment of embodiment 4, the oxytocin peptide is administered via intranasal administration.

Embodiment 6

In a further embodiment of embodiment 5, the oxytocin peptide and the magnesium salt are administered via intranasal administration.

Embodiment 7

In a further embodiment of any one of embodiments 1 to 6, the magnesium salt comprises magnesium chloride.

Embodiment 8

In a further embodiment of any one of embodiments 1 to 7, the magnesium salt comprises magnesium citrate.

Embodiment 9

In a further embodiment of embodiment 8, the effective dose of the oxytocin peptide is about 0.5 µg to about 2000 µg.

Embodiment 10

In a further embodiment of embodiment 8, the effective dose of the magnesium salt provides about 50 µg to about 68 mg of magnesium.

Embodiment 11

In a further embodiment of embodiment 8, the effective dose of the oxytocin peptide and the magnesium salt comprises about 15 µg to about 120 µg of the oxytocin peptide administered in an aqueous solution containing about 1.1% to about 1.6% (w/v) of magnesium (or containing about 10% to about 14% (w/v) of magnesium citrate).

Embodiment 12

In a further embodiment of embodiment 8, the effective dose of the oxytocin peptide and the magnesium salt comprises about 66 µg (or about 60 µg) of the oxytocin peptide administered in an aqueous solution containing about 1.36% magnesium (or about 12% magnesium citrate).

Embodiment 13

In a further embodiment of any one of embodiments 1 to 12, the pain is a chronic pain.

Embodiment 14

In a further embodiment of any one of embodiments 1 to 12, the pain is an acute pain.

Embodiment 15

In a further embodiment of any one of embodiments 1 to 12, the pain is an episodic pain.

Embodiment 16

In a further embodiment of any one of embodiments 1 to 12, the pain is a head or facial pain.

Embodiment 17

In a further embodiment of any one of embodiments 1 to 12, the pain is a trigeminal nerve-associated pain.

Embodiment 18

In a further embodiment of any one of embodiments 1 to 12, the pain is a migraine headache.

Embodiment 19

In a further embodiment of any one of embodiments 1 to 12, the pain is a neck pain (or occipital neuralgia), shoulder pain, or a pain in the upper extremities.

Embodiment 20

In a further embodiment of any one of embodiments 1 to 12, the pain is a cervical nerve-associated pain (or an upper cervical nerve-associated pain).

Embodiment 21

In a further embodiment of any one of embodiments 1 to 20, the oxytocin peptide is human oxytocin (SEQ. ID NO:1).

Embodiment 22

In one embodiment, the invention provides a composition comprising an oxytocin peptide and a magnesium salt, wherein the oxytocin peptide and the magnesium salt are in an amount that produces a synergistic analgesia when used in the treatment of pain.

Embodiment 23

In a further embodiment of embodiment 22, the oxytocin peptide is human oxytocin (SEQ. ID NO:1).

Embodiment 24

In a further embodiment of embodiment 22 or 23, the magnesium salt comprises magnesium citrate and/or magnesium chloride.

Embodiment 25

In a further embodiment of embodiment 24, the magnesium salt comprises magnesium chloride and magnesium citrate.

Embodiment 26

In a further embodiment of any one of embodiments 22 to 25, the composition is a liquid formulation comprising between about 0.01 mg/mL and about 16 mg/mL (or between about 5 IU/mL and about 8000 IU/mL) of the oxytocin peptide.

Embodiment 27

In a further embodiment of embodiment 26, the liquid formulation comprising between about 0.15 mg/mL and about 1.5 mg/mL (or between about 75 IU/mL and about 750 IU/mL) of the oxytocin peptide.

Embodiment 28

In a further embodiment of any one of embodiments 22 to 27, the composition is a liquid formulation comprising the magnesium salt in an amount to provide between about 3 mg/mL and about 30 mg/mL of magnesium or between about 125 mM and about 1200 mM of magnesium.

Embodiment 29

In a further embodiment of embodiment 28, the liquid formulation comprising between about 11 mg/mL and about 15 mg/mL of magnesium or between about 250 mM and about 600 mM of magnesium.

Embodiment 30

In a further embodiment of any one of embodiments 22 to 29, the composition further comprises one or more excipients, vehicles, emulsifiers, stabilizers, preservatives, mucosal adhesives, antibacterial agents, buffers, and/or other additives.

Embodiment 31

In a further embodiment of any one of embodiments 22 to 29, the composition has a pH of about 4.5.

Embodiment 32

In a further embodiment of any one of embodiments 22 to 31, the composition is suitable for nasal administration.

Embodiment 33

In a further embodiment of embodiment 32, the composition further comprises a device for intranasal administration.

Embodiment 34

In a further embodiment of embodiment 33, the device for intranasal administration is a nasal pump apparatus.

Embodiment 35

In a further embodiment of embodiment 34, the nasal pump apparatus comprises a reservoir bottle attached to a pump actuator.

Embodiment 36

In a further embodiment of embodiment 35, the pump actuator is metered to deliver a specified volume of about 50 µL.

Embodiment 37

In a further embodiment of embodiment 34, the nasal pump apparatus comprises a reservoir bottle attached to an aerosolizer.

Embodiment 38

In a further embodiment of any one of embodiments 34 to 37, the nasal pump apparatus comprises one of more of the following: (i) a filter for preventing back flow, (ii) a metal-free fluid path, and (iii) a plastic material stable to gamma-radiation.

Embodiment 39

In one embodiment, the invention provides a method for treating pain comprising administering to a subject in need thereof an effective dose of the composition of any one of embodiments 22 to 32 and a pharmaceutically acceptable carrier.

Embodiment 40

In one embodiment, the invention provides a kit comprising the composition of any one of embodiments 22 to 38 and a packaging.

Embodiment 41

In a further embodiment of embodiment 40, the kit further comprises instructions for administering the composition according to the method of embodiment 39.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

All patents, patent applications, documents, and articles cited herein are incorporated by reference in their entireties.

What is claimed is:

1. A method for treating pain, wherein the pain is a head or facial pain, a neck pain, a shoulder pain, or a pain in the upper extremities, comprising administering to a subject in need thereof an effective dose of an oxytocin peptide and a magnesium salt, wherein the oxytocin peptide is administered via craniofacial mucosal administration, and wherein the molar ratio between the dose of the oxytocin peptide administered and the dose of magnesium ions administered is between about 1:800 and about 1:30000.

2. The method of claim 1, wherein the oxytocin peptide is administered via intranasal administration.

3. The method of claim 1, wherein the effective dose of the oxytocin peptide is about 0.5 μg to about 2000 μg.

4. The method of claim 1, wherein the effective dose of the magnesium salt provides about 50 μg to about 68 mg of magnesium.

5. The method of claim 1, wherein the effective dose of the oxytocin peptide and the magnesium salt comprises about 15 μg to about 120 μg of the oxytocin peptide administered in an aqueous solution containing about 1.1% to about 1.6% (w/v) of magnesium.

6. The method of claim 1, wherein the effective dose of the oxytocin peptide and the magnesium salt comprises about 66 μg of the oxytocin peptide administered in an aqueous solution containing about 1.36% magnesium.

7. The method of claim 1, wherein the pain is a chronic pain, an acute pain, or an episodic pain.

8. The method of claim 1, wherein the pain is a trigeminal nerve-associated pain or a cervical nerve-associated pain.

9. The method of claim 1, wherein the pain is a migraine headache.

10. The method of claim 1, wherein the oxytocin peptide is human oxytocin (SEQ. ID NO:1).

11. A composition comprising an oxytocin peptide and a magnesium salt, wherein the composition is contained in a device for craniofacial mucosal administration, and wherein the molar ratio between the oxytocin peptide in the composition and the magnesium ions in the composition is between about 1:800 and about 1:30000.

12. The composition of claim 11, wherein the oxytocin peptide is human oxytocin (SEQ. ID NO:1).

13. The composition of claim 11, wherein the composition is a liquid formulation comprising between about 0.01 mg/mL and about 16 mg/mL of the oxytocin peptide.

14. The composition of claim 13, wherein the liquid formulation comprising between about 0.15 mg/mL and about 1.5 mg/mL of the oxytocin peptide.

15. The composition of claim 11, wherein the composition is a liquid formulation comprising the magnesium salt in an amount to provide between about 3 mg/mL and about 30 mg/mL of magnesium.

16. The composition of claim 15, wherein the liquid formulation comprising between about 11 mg/mL and about 15 mg/mL of magnesium.

17. The composition of claim 11, further comprises one or more excipients, vehicles, emulsifiers, stabilizers, preservatives, mucosal adhesives, antibacterial agents, buffers, and/or other additives.

18. The composition of claim 11, wherein the composition has a pH of about 4.5.

19. The composition of claim 11, wherein the composition is contained in a device for intranasal administration.

20. The composition of claim 19, wherein the device for intranasal administration is a nasal pump apparatus comprising a reservoir bottle attached to a pump actuator or a reservoir bottle attached to an aerosolizer.

21. A method for treating pain comprising administering to a subject in need thereof an effective dose of the composition of claim 11 and a pharmaceutically acceptable carrier.

22. A kit comprising the composition of claim 11 and a packaging.

23. The method of claim 1, wherein the molar ratio between the dose of the oxytocin peptide administered and the dose of magnesium ions administered is between about 1:800 and about 1:20000.

24. The composition of claim 11, wherein the molar ratio between the oxytocin peptide in the composition and the magnesium ions in the composition is between about 1:800 and about 1:20000.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5
```